US012564456B2

(12) United States Patent
Scheib et al.

(10) Patent No.: US 12,564,456 B2
(45) Date of Patent: Mar. 3, 2026

(54) MODULAR COLPOTOMY CUP COMPONENT FOR ROBOTICALLY CONTROLLED UTERINE MANIPULATOR

(71) Applicant: Cilag GmbH International, Zug (CH)

(72) Inventors: Charles J. Scheib, Loveland, OH (US); Matthew Vargas, San Francisco, CA (US); Clinton Denlinger, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 934 days.

(21) Appl. No.: 17/468,762

(22) Filed: Sep. 8, 2021

(65) Prior Publication Data

US 2023/0076663 A1 Mar. 9, 2023

(51) Int. Cl.
*A61B 34/30* (2016.01)
*A61B 17/42* (2006.01)
*A61B 17/00* (2006.01)

(52) U.S. Cl.
CPC .......... *A61B 34/30* (2016.02); *A61B 17/4241* (2013.01); *A61B 2017/00477* (2013.01); *A61B 2017/4216* (2013.01); *A61B 2017/4225* (2013.01); *A61B 2034/301* (2016.02); *A61B 2560/0443* (2013.01); *A61B 2562/043* (2013.01)

(58) Field of Classification Search
CPC ........ A61B 2017/306; A61B 2017/308; A61B 2018/00291
See application file for complete search history.

(56) References Cited

U.S. PATENT DOCUMENTS

| | | | |
|---|---|---|---|
| 5,902,251 A | * | 5/1999 | vanHooydonk ....... A61N 5/045 |
| | | | 600/549 |
| 8,696,563 B2 | | 4/2014 | Williams et al. |
| 9,522,252 B2 | | 12/2016 | Ahluwalia et al. |

(Continued)

FOREIGN PATENT DOCUMENTS

| | | |
|---|---|---|
| EP | 3981347 A2 | 4/2022 |
| WO | 2020206297 A1 | 10/2020 |

OTHER PUBLICATIONS

International Search Report and Written Opinion, received for PCT Application No. PCT/IB2022/058320, mailed on Feb. 2, 2023, 26 pages.

(Continued)

*Primary Examiner* — Martin T Ton
(74) *Attorney, Agent, or Firm* — Joshua D. Young

(57) ABSTRACT

An apparatus includes a modular colpotomy cup component and a modular shaft component. The modular colpotomy cup component includes a proximal base, an elongated sleeve, an expanding member, and a colpotomy cup. The proximal base is configured to couple to a distal end of a head of a robotic arm. The modular shaft component includes a coupling body and an elongated shaft. The coupling body is configured to couple to the head of the robotic arm such that the modular shaft component and the modular colpotomy cup component are attached to each other via the head of the robotic arm. The elongated shaft extends distally from the coupling body and is configured to be inserted through the opening of the proximal base such that the coupling body is configured to couple to the head of the robotic arm.

16 Claims, 49 Drawing Sheets

(56) References Cited

U.S. PATENT DOCUMENTS

| | | | |
|---|---|---|---|
| 9,743,955 | B2 | 8/2017 | Hill et al. |
| 9,763,741 | B2 | 9/2017 | Alvarez et al. |
| 9,788,859 | B2 | 10/2017 | Parys |
| 10,464,209 | B2 | 11/2019 | Ho et al. |
| 10,639,072 | B2 | 5/2020 | Ahluwalia |
| 10,667,875 | B2 | 6/2020 | DeFonzo et al. |
| 10,765,303 | B2 | 9/2020 | Graetzel et al. |
| 10,827,913 | B2 | 11/2020 | Ummalaneni et al. |
| 10,881,280 | B2 | 1/2021 | Baez, Jr. |
| 10,898,277 | B2 | 1/2021 | Srinivasan et al. |
| 10,905,505 | B1 | 2/2021 | Barakat et al. |
| 11,058,493 | B2 | 7/2021 | Rafii-Tari et al. |
| 2009/0182329 | A1 | 7/2009 | Dycus |
| 2013/0165854 | A1 | 6/2013 | Sandhu et al. |
| 2014/0276916 | A1* | 9/2014 | Ahluwalia ............. A61B 90/50 606/119 |
| 2015/0148812 | A1 | 5/2015 | Ahluwalia |
| 2015/0351621 | A1 | 12/2015 | Hill et al. |
| 2016/0270819 | A1* | 9/2016 | Ahluwalia ......... A61B 17/4241 |
| 2017/0224421 | A1 | 8/2017 | Marczyk et al. |
| 2018/0325552 | A1* | 11/2018 | Weihe ................ A61B 18/1482 |
| 2018/0325575 | A1 | 11/2018 | Begg et al. |
| 2018/0338787 | A1 | 11/2018 | Cote et al. |
| 2019/0038314 | A1* | 2/2019 | Jadhav .............. A61B 1/00066 |
| 2020/0078109 | A1 | 3/2020 | Steger et al. |
| 2021/0100584 | A1 | 4/2021 | Einarsson |
| 2021/0282814 | A1* | 9/2021 | Prior .................. A61B 17/4241 |
| 2021/0282836 | A1* | 9/2021 | Prior ..................... A61B 34/35 |
| 2021/0353330 | A1 | 11/2021 | Prior et al. |
| 2022/0104875 | A1* | 4/2022 | Gleiman ............... A61B 18/16 |
| 2022/0192707 | A1* | 6/2022 | Barakat .................. A61B 34/30 |
| 2023/0075930 | A1 | 3/2023 | Scheib et al. |

OTHER PUBLICATIONS

Invitation to Pay Additional Fees, received for PCT Application No. PCT/IB2022/058320, mailed on Dec. 23, 2022, 15 pages.

* cited by examiner

MODULAR COLPOTOMY CUP COMPONENT FOR ROBOTICALLY CONTROLLED UTERINE MANIPULATOR

BACKGROUND

A variety of medical instruments may be used in procedures conducted by a medical professional operator, as well as applications in robotically assisted surgeries. In the case of robotically assisted surgery, the clinician may operate a master controller to remotely control the motion of such medical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the medical instrument. In some scenarios, a servo motor moves a manipulator supporting the medical instrument based on the clinician's manipulation of the hand input devices. During the medical procedure, the clinician may employ, via a robotic system, a variety of medical instruments including an ultrasonic blade, a surgical stapler, a tissue grasper, a needle driver, an electrosurgical cautery probes, etc. Each of these structures performs functions for the clinician, for example, cutting tissue, coagulating tissue, holding or driving a needle, grasping a blood vessel, dissecting tissue, or cauterizing tissue.

Examples of robotic systems are described in U.S. Pat. No. 9,763,741, entitled "System for Robotic-Assisted Endolumenal Surgery and Related Methods," issued Sep. 19, 2017, the disclosure of which is incorporated by reference herein, in its entirety; U.S. Pat. No. 10,464,209, entitled "Robotic System with Indication of Boundary for Robotic Arm," issued Nov. 5, 2019, the disclosure of which is incorporated by reference herein, in its entirety; U.S. Pat. No. 10,667,875, entitled "Systems and Techniques for Providing Multiple Perspectives During Medical Procedures," issued Jun. 2, 2020, the disclosure of which is incorporated by reference herein, in its entirety; U.S. Pat. No. 10,765,303, entitled "System and Method for Driving Medical Instrument," issued Sep. 8, 2020, the disclosure of which is incorporated by reference herein, in its entirety; U.S. Pat. No. 10,827,913, entitled "Systems and Methods for Displaying Estimated Location of Instrument," issued Nov. 10, 2020, the disclosure of which is incorporated by reference herein, in its entirety; U.S. Pat. No. 10,881,280, entitled "Manually and Robotically Controllable Medical Instruments," issued Jan. 5, 2021, the disclosure of which is incorporated by reference herein, in its entirety; U.S. Pat. No. 10,898,277, entitled "Systems and Methods for Registration of Location Sensors," issued Jan. 26, 2012, the disclosure of which is incorporated by reference herein, in its entirety; and U.S. Pat. No. 11,058,493, entitled "Robotic System Configured for Navigation Path Tracing," issued Jul. 13, 2021, the disclosure of which is incorporated by reference herein, in its entirety.

During a hysterectomy procedure, a colpotomy may be performed at the cervicovaginal junction. Such procedures may include the use of a uterine manipulator that includes a colpotomy cup or similar structure. Examples of instruments that may be used during a hysterectomy procedure are described in U.S. Pat. No. 9,743,955, entitled "Intracorporeal Transilluminator of Tissue Using LED Array," issued Aug. 29, 2017; U.S. Pat. No. 9,788,859, entitled "Uterine Manipulators and Related Components and Methods," issued Oct. 17, 2017; U.S. Pat. No. 10,639,072, entitled "Uterine Manipulator," issued May 5, 2020; U.S. Pub. No. 2021/0100584, entitled "Uterine Manipulator," published Apr. 8, 2021; U.S. Pub. No. 2018/0325552, entitled "Colpotomy Systems, Devices, and Methods with Rotational Cutting," published Nov. 15, 2018.

While several medical instruments, systems, and methods have been made and used, it is believed that no one prior to the inventors has made or used the invention described in the appended claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

I. Overview of Example of Robotic System

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Example of Robotic System Cart

Figure 1:
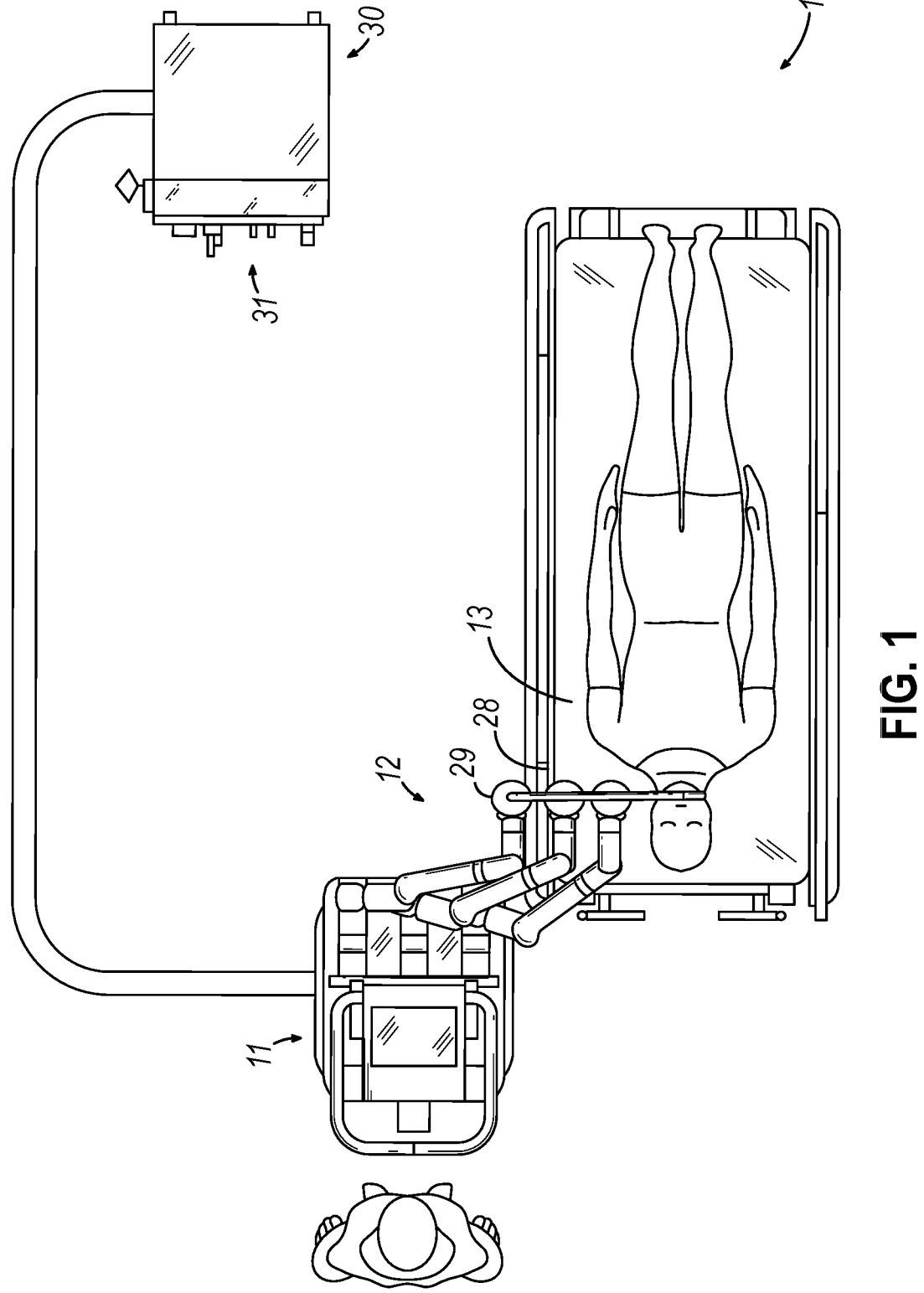
FIG. 1 depicts an embodiment of a cart-based robotic system arranged for diagnostic and/or therapeutic bronchoscopy procedure(s).
Figure 2:
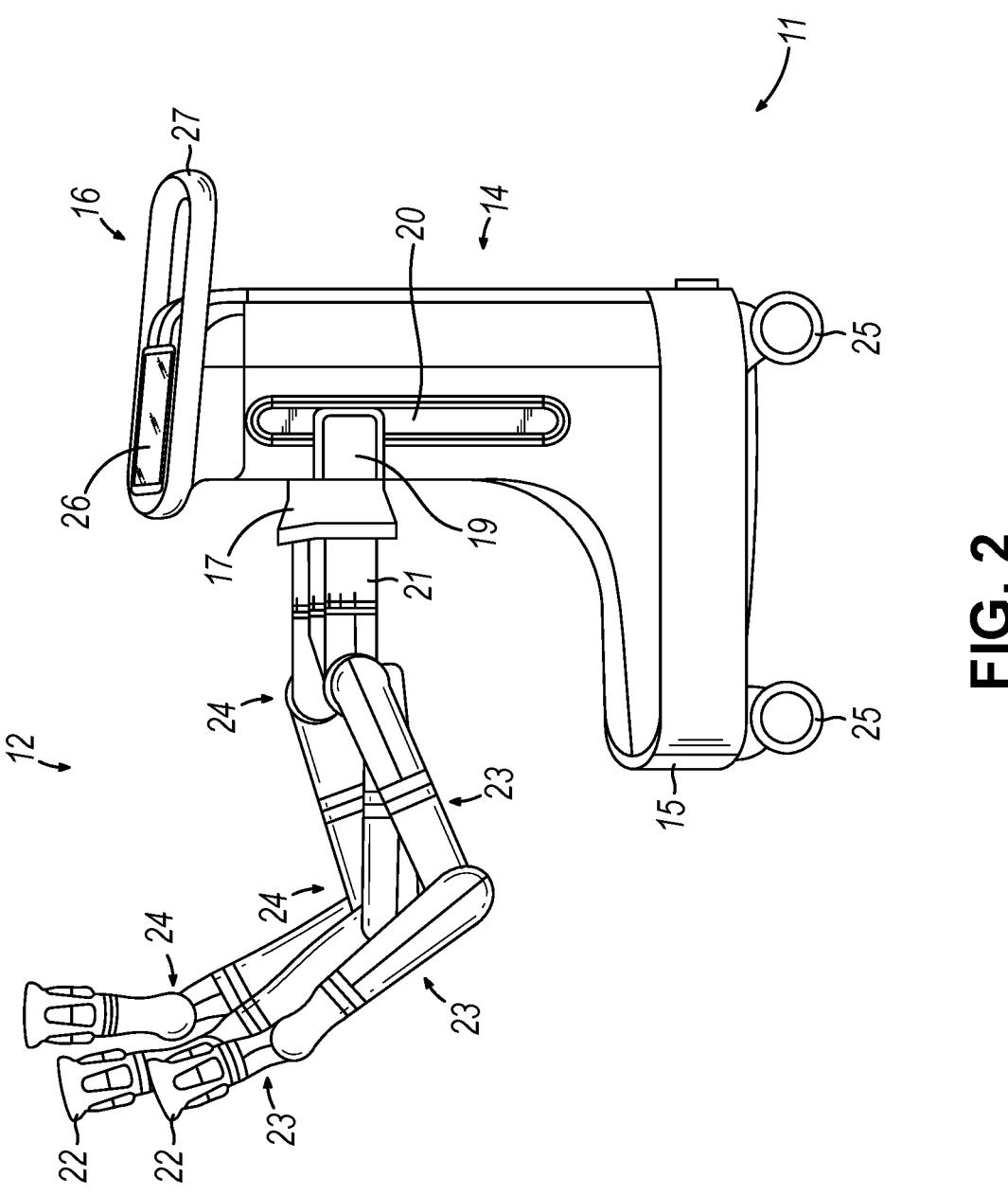
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system (10) arranged for a diagnostic and/or therapeutic bronchoscopy procedure. During a bronchoscopy, the system (10) may comprise a cart (11) having one or more robotic arms (12) to deliver a medical instrument, such as a steerable endoscope (13), which may be a procedure-specific bronchoscope for bronchoscopy, to a natural orifice access point (i.e., the mouth of the patient positioned on a table in the present example) to deliver diagnostic and/or therapeutic tools. As shown, the cart (11) may be positioned proximate to the patient's upper torso in order to provide access to the access point. Similarly, the robotic arms (12) may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart (11) is properly positioned, the robotic arms (12) may insert the steerable endoscope (13) into the patient robotically, manually, or a combination thereof. As shown, the steerable endoscope (13) may comprise at least two telescoping parts, such as an inner leader portion and an outer sheath portion, each portion coupled to a separate instrument driver from the set of instrument drivers (28), each instrument driver coupled to the distal end of an individual robotic arm. This linear arrangement of the instrument drivers (28), which facilitates coaxially aligning the leader portion with the sheath portion, creates a "virtual rail" (29) that may be repositioned in space by manipulating the one or more robotic arms (12) into different angles and/or positions. The virtual rails described herein are depicted in the Figures using dashed lines, and accordingly the dashed lines do not depict any physical structure of the system. Translation of the instrument drivers (28) along the virtual rail (29) telescopes the inner leader portion relative to the outer sheath portion or advances or retracts the endoscope (13) from the patient. The angle of the virtual rail (29) may be adjusted, translated, and pivoted based on clinical application or physician preference. For example, in bronchoscopy, the angle and position of the virtual rail (29) as shown represents a compromise between providing physician access to the endoscope (13) while minimizing friction that results from bending the endoscope (13) into the patient's mouth.

The endoscope (13) may be directed down the patient's trachea and lungs after insertion using precise commands from the robotic system until reaching the target destination or operative site. In order to enhance navigation through the patient's lung network and/or reach the desired target, the endoscope (13) may be manipulated to telescopically extend the inner leader portion from the outer sheath portion to obtain enhanced articulation and greater bend radius. The use of separate instrument drivers (28) also allows the leader portion and sheath portion to be driven independent of each other.

For example, the endoscope (13) may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope (13) may endoscopically deliver tools to resect the potentially cancerous tissue. In some instances, diagnostic and therapeutic treatments can be delivered in separate procedures. In those circumstances, the endoscope (13) may also be used to deliver a fiducial to "mark" the location of the target nodule as well. In other instances, diagnostic and therapeutic treatments may be delivered during the same procedure.

The system (10) may also include a movable tower (30), which may be connected via support cables to the cart (11) to provide support for controls, electronics, fluidics, optics, sensors, and/or power to the cart (11). Placing such functionality in the tower (30) allows for a smaller form factor cart (11) that may be more easily adjusted and/or repositioned by an operating physician and his/her staff. Additionally, the division of functionality between the cart/table and the support tower (30) reduces operating room clutter and facilitates improving clinical workflow. While the cart (11) may be positioned close to the patient, the tower (30) may be stowed in a remote location to stay out of the way during a procedure.

In support of the robotic systems described above, the tower (30) may include component(s) of a computer-based control system that stores computer program instructions, for example, within a non-transitory computer-readable storage medium such as a persistent magnetic storage drive, solid state drive, etc. The execution of those instructions, whether the execution occurs in the tower (30) or the cart (11), may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower (30) may also include a pump, flow meter, valve control, and/or fluid access in order to provide controlled irrigation and aspiration capabilities to the system that may be deployed through the endoscope (13). These components may also be controlled using the computer system of tower (30). In some embodiments, irrigation and aspiration capabilities may be delivered directly to the endoscope (13) through separate cable(s).

The tower (30) may include a voltage and surge protector designed to provide filtered and protected electrical power to the cart (11), thereby avoiding placement of a power transformer and other auxiliary power components in the cart (11), resulting in a smaller, more moveable cart (11).

The tower (30) may also include support equipment for the sensors deployed throughout the robotic system (10). For example, the tower (30) may include opto-electronics equipment for detecting, receiving, and processing data received from the optical sensors or cameras throughout the robotic system (10). In combination with the control system, such opto-electronics equipment may be used to generate real-time images for display in any number of consoles deployed throughout the system, including in the tower (30). Similarly, the tower (30) may also include an electronic subsystem for receiving and processing signals received from deployed electromagnetic (EM) sensors. The tower (30) may also be used to house and position an EM field generator for detection by EM sensors in or on the medical instrument.

The tower (30) may also include a console (31) in addition to other consoles available in the rest of the system, e.g., console mounted on top of the cart. The console (31) may include a user interface and a display screen, such as a touchscreen, for the physician operator. Consoles in system (10) are generally designed to provide both robotic controls as well as pre-operative and real-time information of the procedure, such as navigational and localization information of the endoscope (13). When the console (31) is not the only console available to the physician, it may be used by a second operator, such as a nurse, to monitor the health or vitals of the patient and the operation of system, as well as provide procedure-specific data, such as navigational and localization information. In other embodiments, the console (31) is housed in a body that is separate from the tower (30).

The tower (30) may be coupled to the cart (11) and endoscope (13) through one or more cables or connections (not shown). In some embodiments, the support functionality from the tower (30) may be provided through a single cable to the cart (11), simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart (11) generally includes an elongated support structure (14) (often referred to as a "column"), a cart base (15), and a console (16) at the top of the column (14). The column (14) may include one or more carriages, such as a carriage (17) (alternatively "arm support") for supporting the deployment of one or more robotic arms (12) (three shown in FIG. 2). The carriage (17) may include individually configurable arm mounts that rotate along a perpendicular axis to adjust the base of the robotic arms (12) for better positioning relative to the patient. The carriage (17) also includes a carriage interface (19) that allows the carriage (17) to vertically translate along the column (14).

The carriage interface (19) is connected to the column (14) through slots, such as slot (20), that are positioned on opposite sides of the column (14) to guide the vertical translation of the carriage (17). The slot (20) contains a vertical translation interface to position and hold the carriage at various vertical heights relative to the cart base (15). Vertical translation of the carriage (17) allows the cart (11) to adjust the reach of the robotic arms (12) to meet a variety of table heights, patient sizes, and physician preferences. Similarly, the individually configurable arm mounts on the carriage (17) allow the robotic arm base (21) of robotic arms (12) to be angled in a variety of configurations.

In some embodiments, the slot (20) may be supplemented with slot covers that are flush and parallel to the slot surface to prevent dirt and fluid ingress into the internal chambers of the column (14) and the vertical translation interface as the carriage (17) vertically translates. The slot covers may be deployed through pairs of spring spools positioned near the vertical top and bottom of the slot (20). The covers are coiled within the spools until deployed to extend and retract from their coiled state as the carriage (17) vertically translates up and down. The spring-loading of the spools provides force to retract the cover into a spool when carriage (17) translates towards the spool, while also maintaining a tight seal when the carriage (17) translates away from the spool. The covers may be connected to the carriage (17) using, for example, brackets in the carriage interface (19) to ensure proper extension and retraction of the cover as the carriage (17) translates.

The column (14) may internally comprise mechanisms, such as gears and motors, that are designed to use a vertically aligned lead screw to translate the carriage (17) in a mechanized fashion in response to control signals generated in response to user inputs, e.g., inputs from the console (16).

The robotic arms (12) may generally comprise robotic arm bases (21) and end effectors (22), separated by a series of linkages (23) that are connected by a series of joints (24), each joint comprising an independent actuator, each actuator comprising an independently controllable motor. Each independently controllable joint represents an independent degree of freedom available to the robotic arm. Each of the arms (12) have seven joints, and thus provide seven degrees of freedom. A multitude of joints result in a multitude of degrees of freedom, allowing for "redundant" degrees of freedom. Redundant degrees of freedom allow the robotic arms (12) to position their respective end effectors (22) at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base (15) balances the weight of the column (14), carriage (17), and arms (12) over the floor. Accordingly, the cart base (15) houses heavier components, such as electronics, motors, power supply, as well as components that either enable movement and/or immobilize the cart. For example, the cart base (15) includes rollable wheel-shaped casters (25) that allow for the cart to easily move around the room prior to a procedure. After reaching the appropriate position, the casters (25) may be immobilized using wheel locks to hold the cart (11) in place during the procedure.

Positioned at the vertical end of column (14), the console (16) allows for both a user interface for receiving user input and a display screen (or a dual-purpose device such as, for example, a touchscreen (26)) to provide the physician user with both pre-operative and intra-operative data. Potential pre-operative data on the touchscreen (26) may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console (16) may be positioned and tilted to allow a physician to access the console from the side of the column (14) opposite carriage (17). From this position, the physician may view the console (16), robotic arms (12), and patient while operating the console (16) from behind the cart (11). As shown, the console (16) also includes a handle (27) to assist with maneuvering and stabilizing cart (11).

Figure 3:
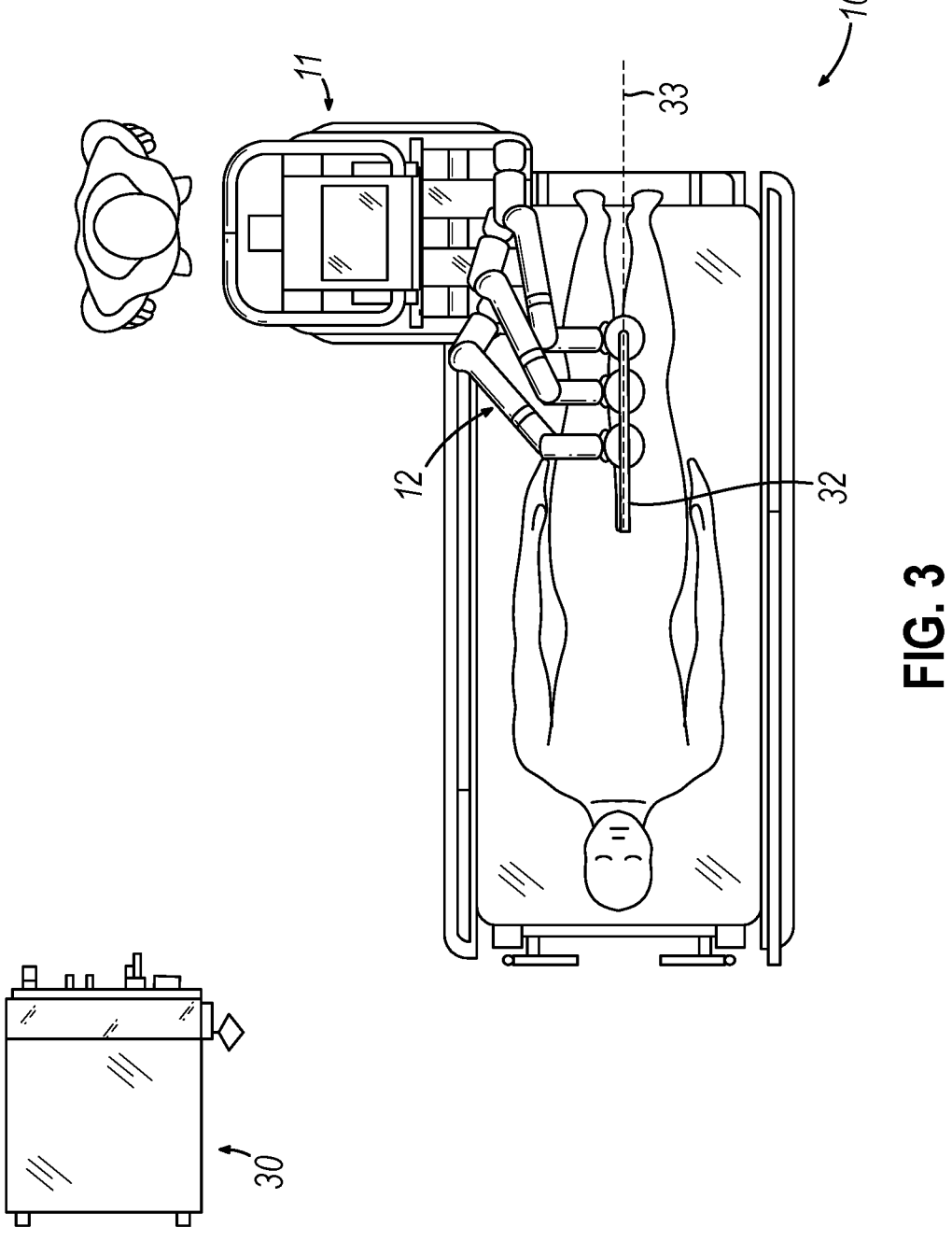
FIG. 3 depicts an embodiment of the robotic system of FIG. 1 arranged for ureteroscopy.

FIG. 3 illustrates an embodiment of a robotically-enabled system (10) arranged for ureteroscopy. In a ureteroscopic procedure, the cart (11) may be positioned to deliver a ureteroscope (32), a procedure-specific endoscope designed to traverse a patient's urethra and ureter, to the lower abdominal area of the patient. In a ureteroscopy, it may be desirable for the ureteroscope (32) to be directly aligned with the patient's urethra to reduce friction and forces on the sensitive anatomy in the area. As shown, the cart (11) may be aligned at the foot of the table to allow the robotic arms (12) to position the ureteroscope (32) for direct linear access to the patient's urethra. From the foot of the table, the robotic arms (12) may insert the ureteroscope (32) along the virtual rail (33) directly into the patient's lower abdomen through the urethra.

After insertion into the urethra, using similar control techniques as in bronchoscopy, the ureteroscope (32) may be navigated into the bladder, ureters, and/or kidneys for diagnostic and/or therapeutic applications. For example, the ureteroscope (32) may be directed into the ureter and kidneys to break up kidney stone build up using a laser or ultrasonic lithotripsy device deployed down the working channel of the ureteroscope (32). After lithotripsy is complete, the resulting stone fragments may be removed using baskets deployed down the ureteroscope (32).

Figure 4:
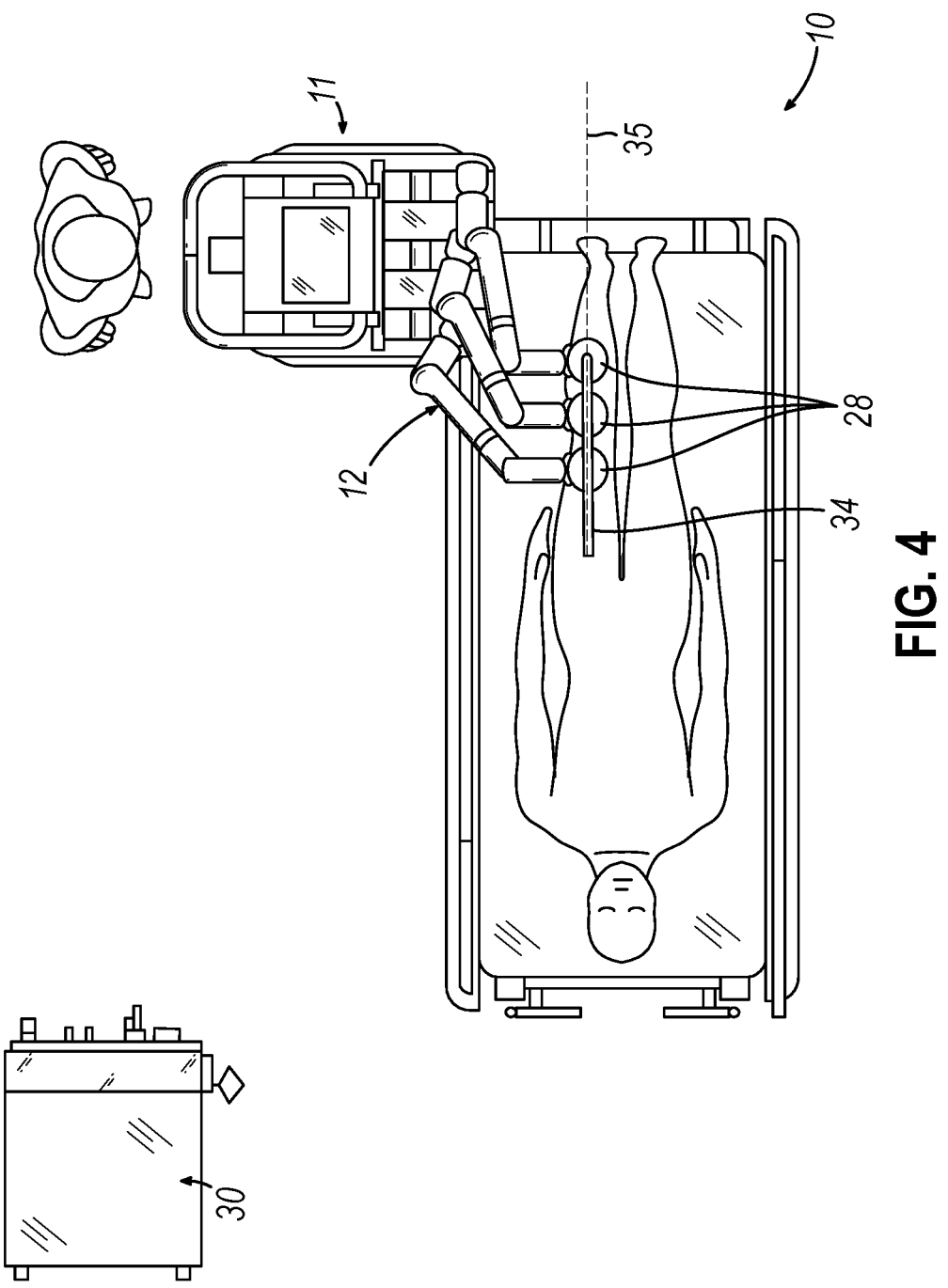
FIG. 4 depicts an embodiment of the robotic system of FIG. 1 arranged for a vascular procedure.

FIG. 4 illustrates an embodiment of a robotically-enabled system similarly arranged for a vascular procedure. In a vascular procedure, the system (10) may be configured such that the cart (11) may deliver a medical instrument (34), such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart (11) may be positioned towards the patient's legs and lower abdomen to allow the robotic arms (12) to provide a virtual rail (35) with direct linear access to the femoral artery access point in the patient's thigh/hip region. After insertion into the artery, the medical instrument (34) may be directed and inserted by translating the instrument drivers (28). Alternatively, the cart may be positioned around the patient's upper abdomen in order to reach alternative vascular access points, such as, for example, the carotid and brachial arteries near the shoulder and wrist.

B. Example of Robotic System Table

Figure 5:
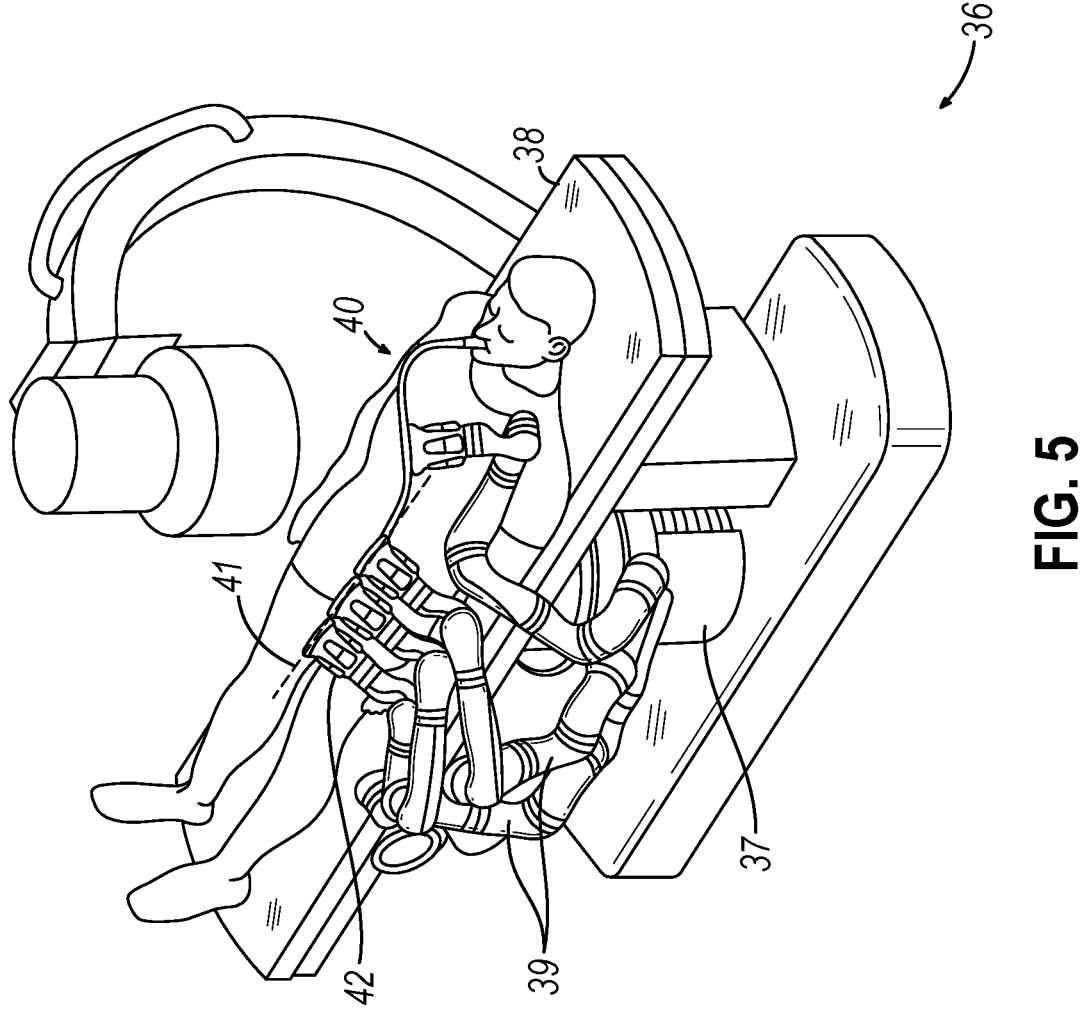
FIG. 5 depicts an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System (36) includes a support structure or column (37) for supporting platform (38) (shown as a "table" or "bed") over the floor. Much like in the cart-based systems, the end effectors of the robotic arms (39) of the system (36) comprise instrument drivers (42) that are designed to manipulate an elongated medical instrument, such as a bronchoscope (40) in FIG. 5, through or along a virtual rail (41) formed from the linear alignment of the instrument drivers (42). In practice, a C-arm for providing fluoroscopic imaging may be positioned over the patient's upper abdominal area by placing the emitter and detector around table (38).

Figure 6:
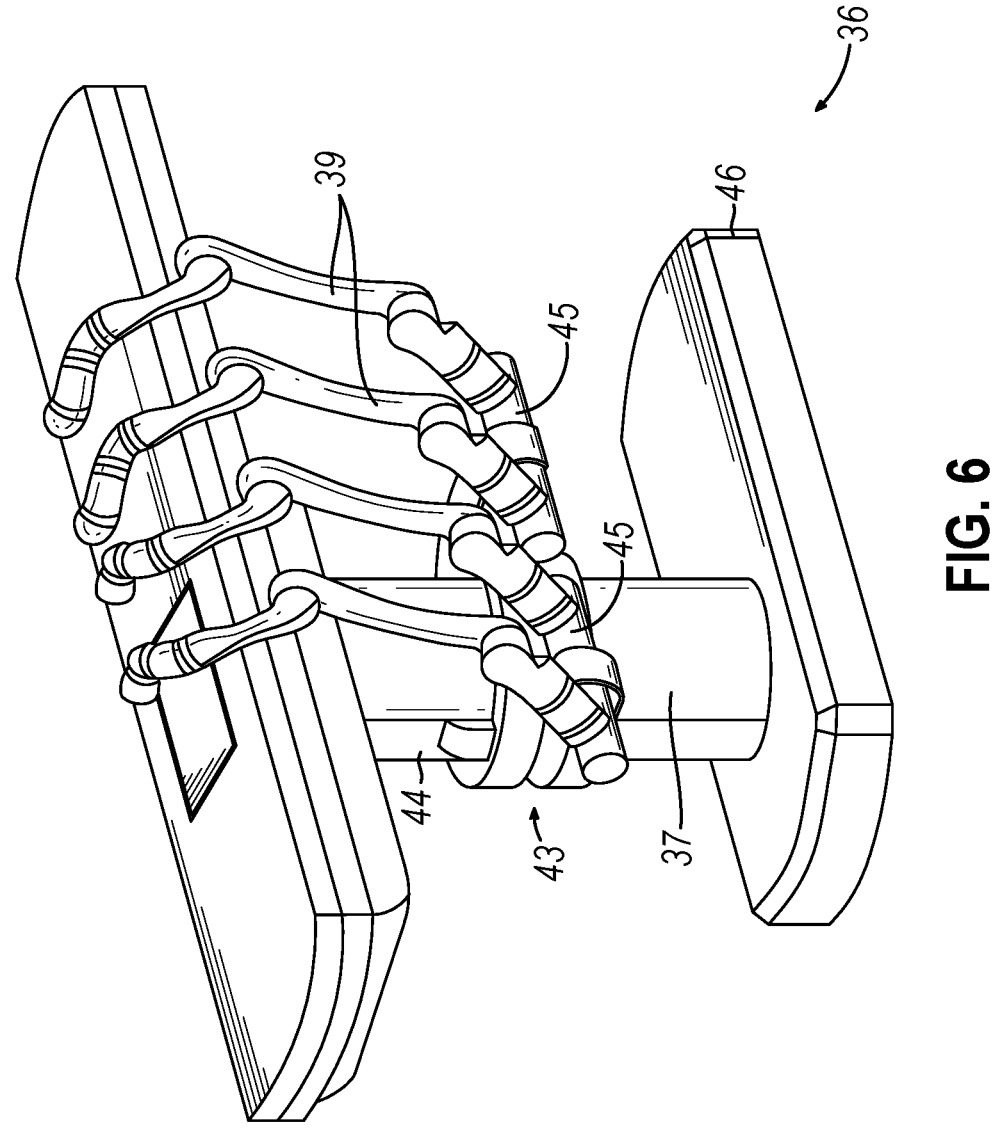
FIG. 6 provides an alternative view of the robotic system of FIG. 5.

FIG. 6 provides an alternative view of the system (36) without the patient and medical instrument for discussion purposes. As shown, the column (37) may include one or more carriages (43) shown as ring-shaped in the system (36), from which the one or more robotic arms (39) may be based. The carriages (43) may translate along a vertical column interface 44 that runs the length of the column (37) to provide different vantage points from which the robotic arms (39) may be positioned to reach the patient. The carriage(s) (43) may rotate around the column (37) using a mechanical motor positioned within the column (37) to allow the robotic arms (39) to have access to multiples sides of the table (38), such as, for example, both sides of the patient. In embodiments with multiple carriages, the carriages may be individually positioned on the column and may translate and/or rotate independent of the other carriages. While carriages (43) need not surround the column (37) or even be circular, the ring-shape as shown facilitates rotation of the carriages (43) around the column (37) while maintaining structural balance. Rotation and translation of the carriages (43) allows the system to align the medical instruments, such as endoscopes and laparoscopes, into different access points on the patient. In other embodiments (not shown), the system (36) can include a patient table or bed with adjustable arm supports in the form of bars or rails extending alongside it. One or more robotic arms (39) (e.g., via a shoulder with an elbow joint) can be attached to the adjustable arm supports, which can be vertically adjusted. By providing vertical adjustment, the robotic arms (39) are advantageously capable of being stowed compactly beneath the patient table or bed, and subsequently raised during a procedure.

Figure 9:
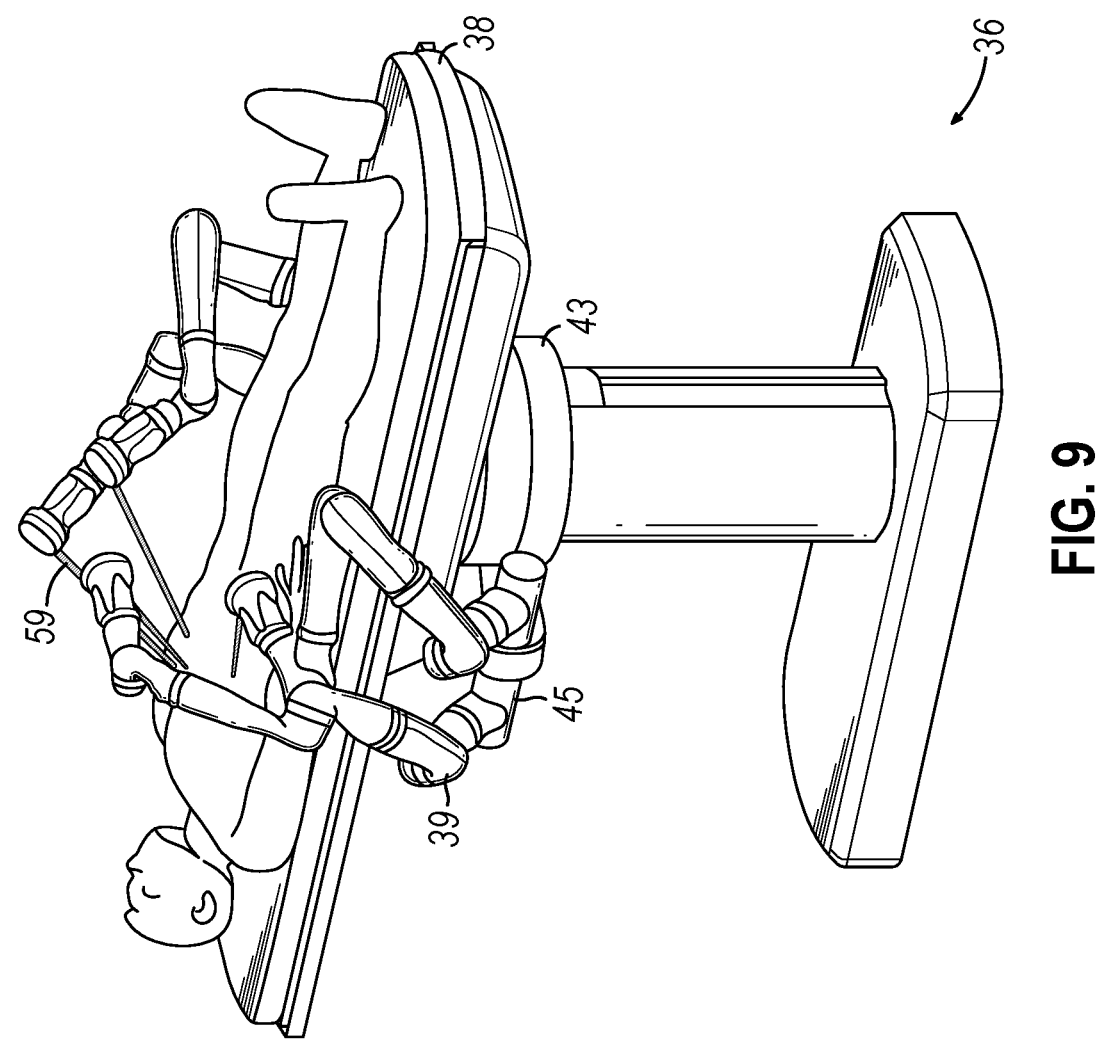
FIG. 9 depicts an embodiment of a table-based robotic system configured for a laparoscopic procedure.

The arms (39) may be mounted on the carriages through a set of arm mounts (45) comprising a series of joints that may individually rotate and/or telescopically extend to provide additional configurability to the robotic arms (39). Additionally, the arm mounts (45) may be positioned on the carriages (43) such that, when the carriages (43) are appropriately rotated, the arm mounts (45) may be positioned on either the same side of table (38) (as shown in FIG. 6), on opposite sides of table (38) (as shown in FIG. 9), or on adjacent sides of the table (38) (not shown).

The column (37) structurally provides support for the table (38), and a path for vertical translation of the carriages. Internally, the column (37) may be equipped with lead screws for guiding vertical translation of the carriages, and motors to mechanize the translation of said carriages based the lead screws. The column (37) may also convey power and control signals to the carriage (43) and robotic arms (39) mounted thereon.

The table base (46) serves a similar function as the cart base (15) in cart (11) shown in FIG. 2, housing heavier components to balance the table/bed (38), the column (37), the carriages (43), and the robotic arms (39). The table base (46) may also incorporate rigid casters to provide stability during procedures. Deployed from the bottom of the table base (46), the casters may extend in opposite directions on both sides of the base (46) and retract when the system (36) needs to be moved.

Continuing with FIG. 6, the system (36) may also include a tower (not shown) that divides the functionality of System (36) between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
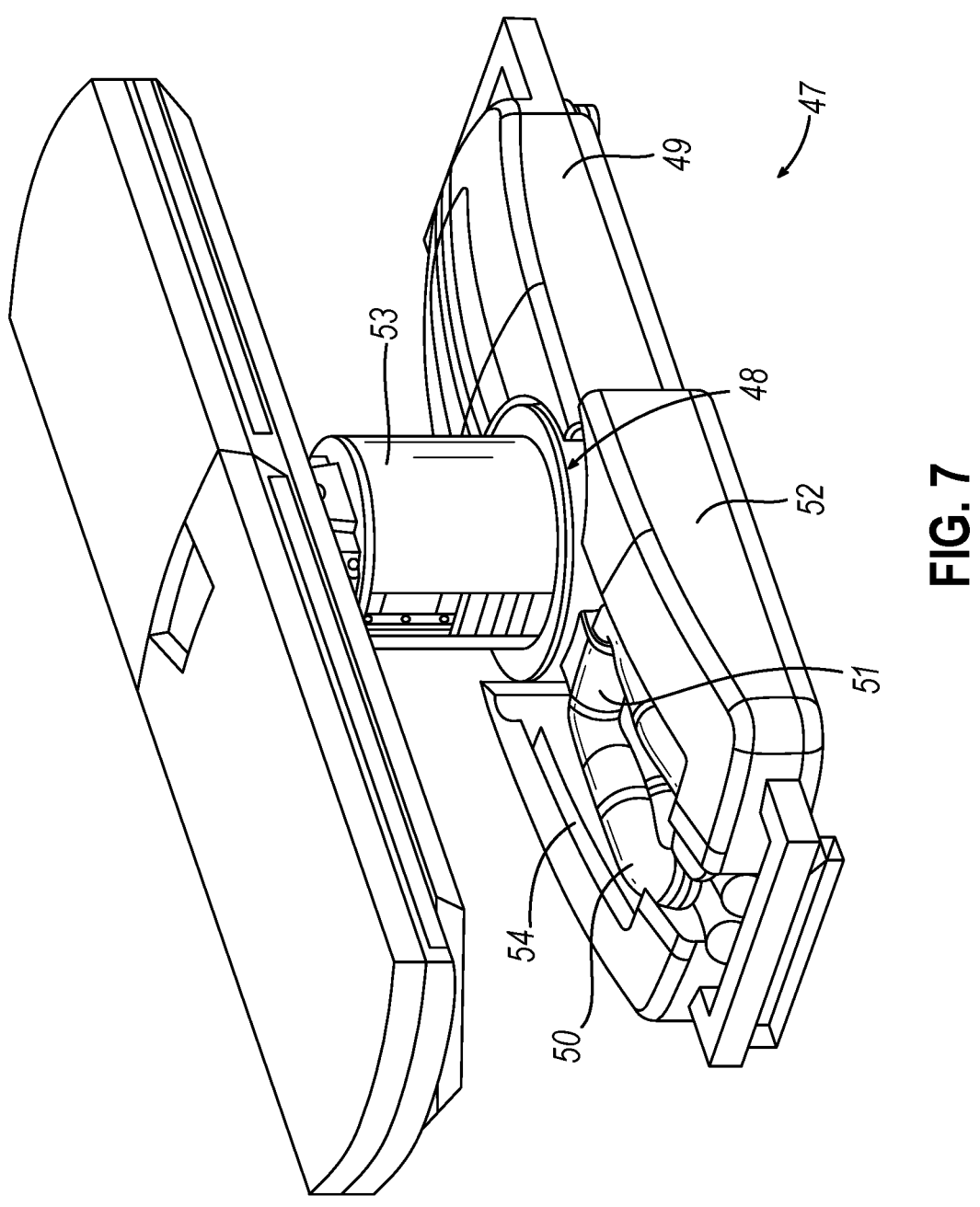
FIG. 7 depicts an example system configured to stow robotic arm(s).

In some embodiments, a table base may stow and store the robotic arms when not in use. FIG. 7 illustrates a system (47) that stows robotic arms in an embodiment of the table-based system. In system (47), carriages (48) may be vertically translated into base (49) to stow robotic arms (50), arm mounts (51), and the carriages (48) within the base (49). Base covers (52) may be translated and retracted open to deploy the carriages (48), arm mounts (51), and arms (50) around column (53), and closed to stow to protect them when not in use. The base covers (52) may be sealed with a membrane (54) along the edges of its opening to prevent dirt and fluid ingress when closed.

Figure 8:
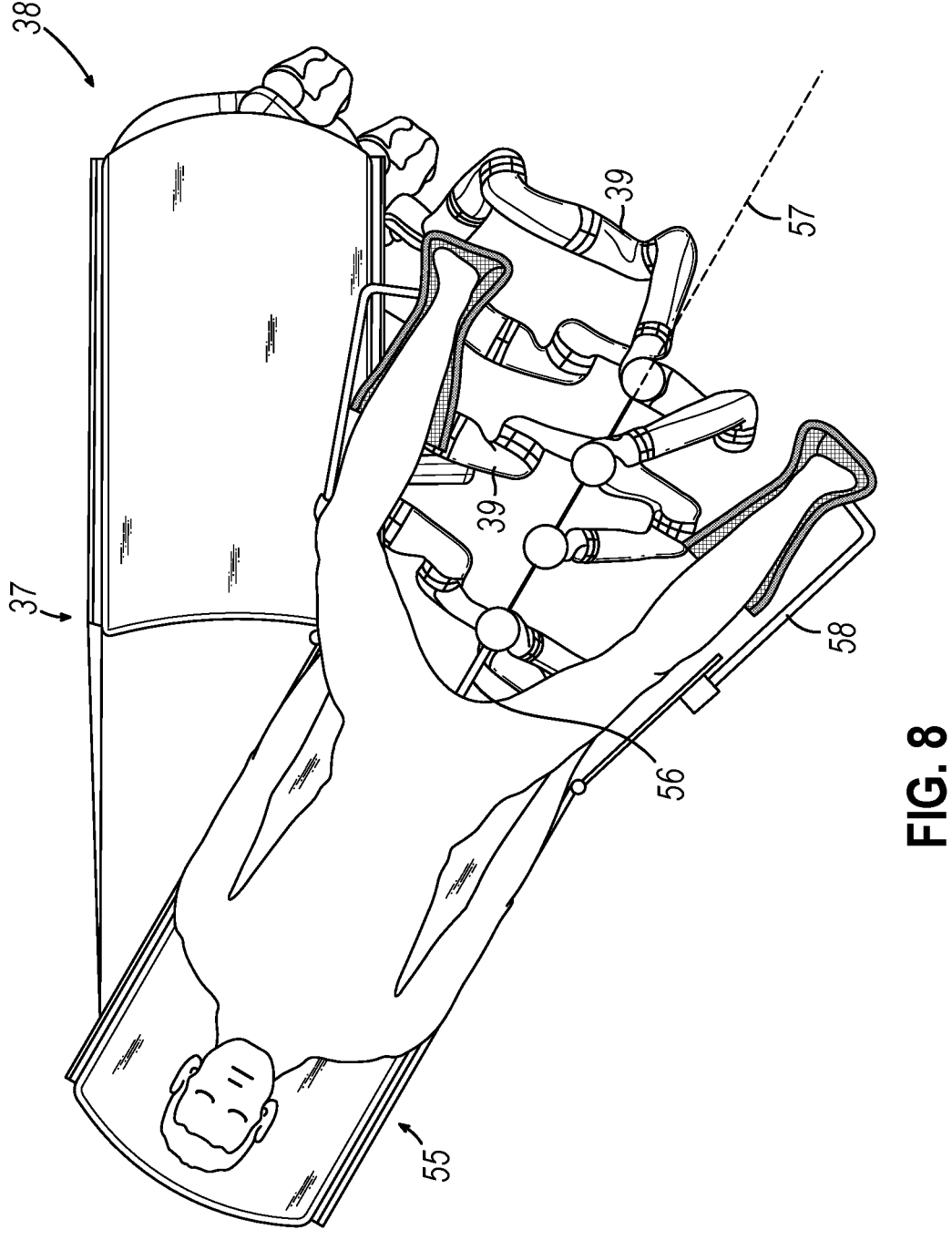
FIG. 8 depicts an embodiment of a table-based robotic system configured for a ureteroscopy procedure.

FIG. 8 illustrates an embodiment of a robotically-enabled table-based system configured for a ureteroscopy procedure. In a ureteroscopy, the table (38) may include a swivel portion (55) for positioning a patient off-angle from the column (37) and table base (46). The swivel portion (55) may rotate or pivot around a pivot point (e.g., located below the patient's head) in order to position the bottom portion of the swivel portion (55) away from the column (37). For example, the pivoting of the swivel portion (55) allows a C-arm (not shown) to be positioned over the patient's lower abdomen without competing for space with the column (not shown) below table (38). By rotating the carriage (35) (not shown) around the column (37), the robotic arms (39) may directly insert a ureteroscope (56) along a virtual rail (57) into the patient's groin area to reach the urethra. In a ureteroscopy, stirrups (58) may also be fixed to the swivel portion (55) of the table (38) to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages (43) of the system (36) may be rotated and vertically adjusted to position pairs of the robotic arms (39) on opposite sides of the table (38), such that instrument (59) may be positioned using the arm mounts (45) to be passed through minimal incisions on both sides of the patient to reach his/her abdominal cavity.

Figure 10:
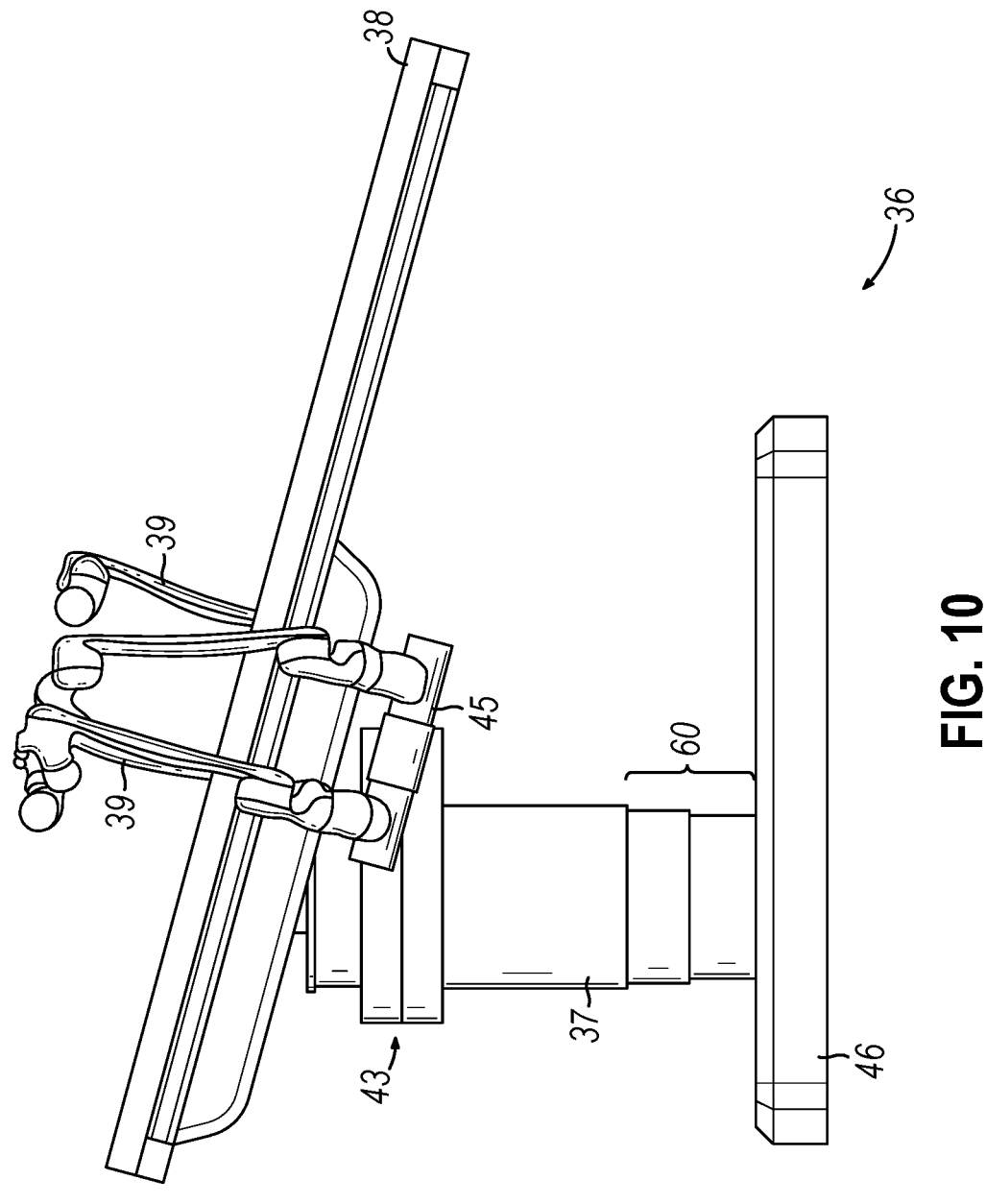
FIG. 10 depicts an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system (36) may accommodate tilt of the table (38) to position one portion of the table at a greater distance from the floor than the other. Additionally, the arm mounts (45) may rotate to match the tilt such that the arms (39) maintain the same planar relationship with table (38). To accommodate steeper angles, the column (37) may also include telescoping portions (60) that allow vertical extension of column (37) to keep the table (38) from touching the floor or colliding with base (46).

Figure 11:
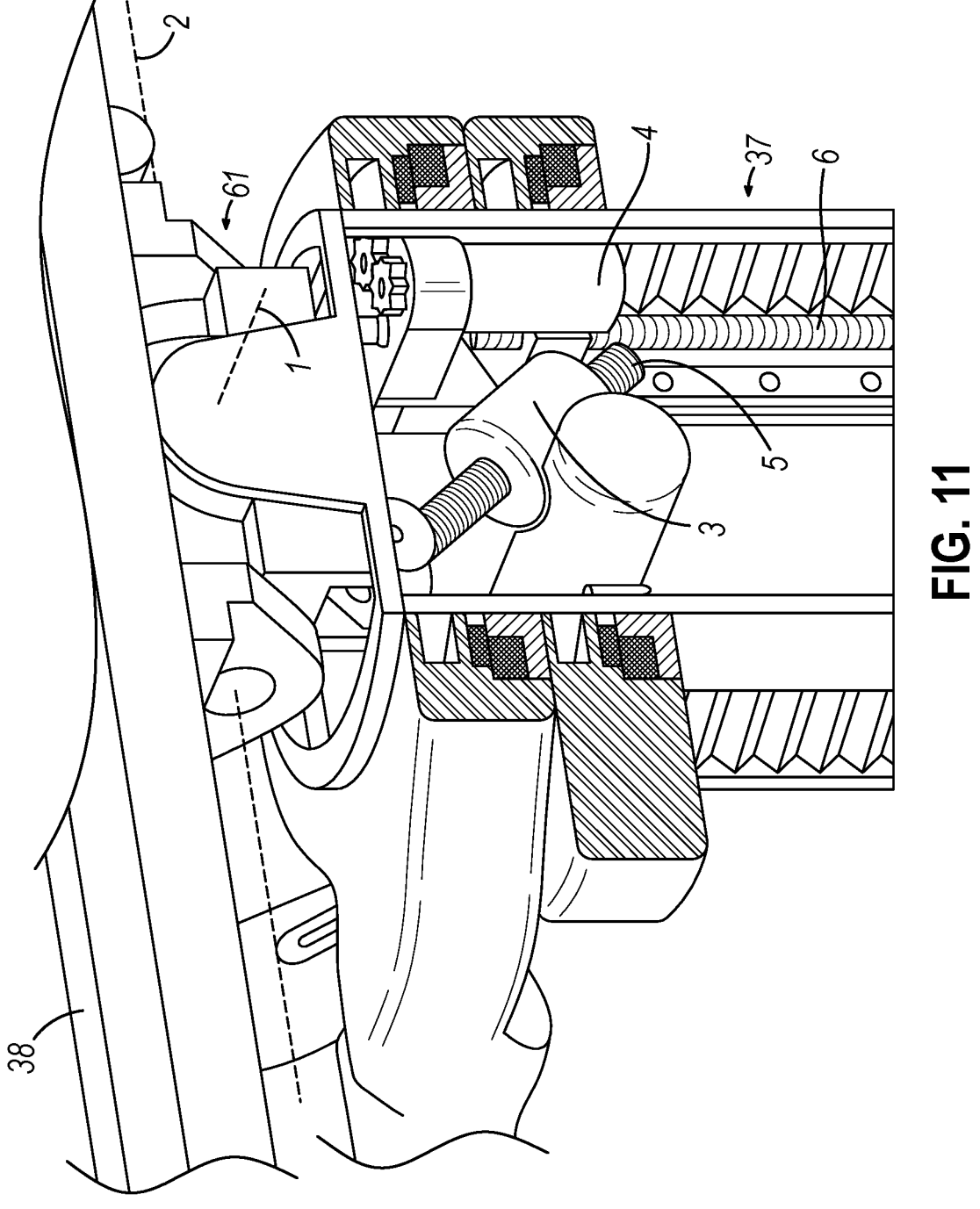
FIG. 11 provides a detailed illustration of the interface between the table and the column of the table-based robotic system of FIGS. 5-10.

FIG. 11 provides a detailed illustration of the interface between the table (38) and the column (37). Pitch rotation mechanism (61) may be configured to alter the pitch angle of the table (38) relative to the column (37) in multiple degrees of freedom. The pitch rotation mechanism (61) may be enabled by the positioning of orthogonal axes (1, 2) at the column-table interface, each axis actuated by a separate motor (3, 4) responsive to an electrical pitch angle command. Rotation along one screw (5) would enable tilt adjustments in one axis (1), while rotation along the other screw (6) would enable tilt adjustments along the other axis (2). In some embodiments, a ball joint can be used to alter the pitch angle of the table (38) relative to the column (37) in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
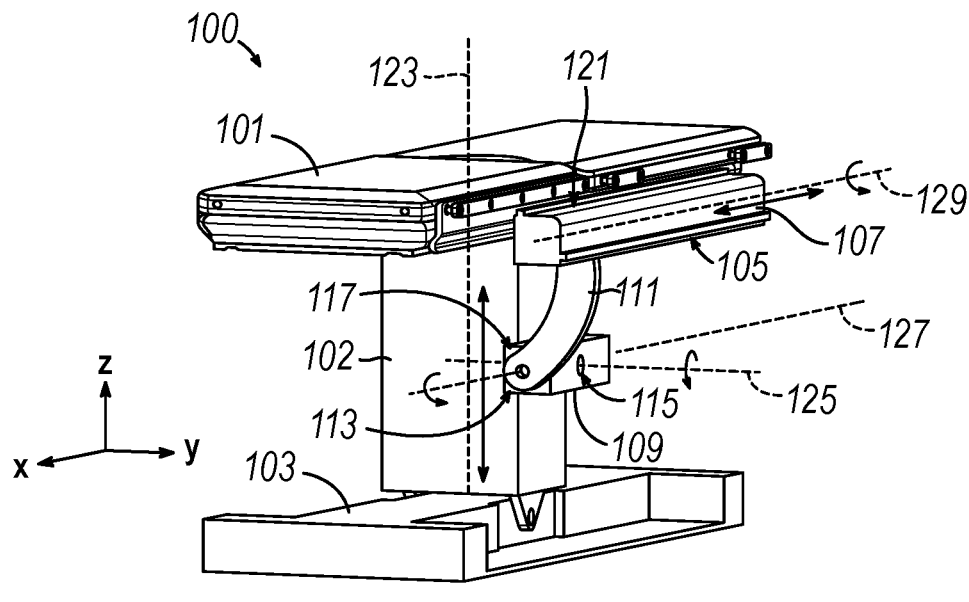
FIG. 12 depicts an alternative embodiment of a table-based robotic system.
Figure 13:
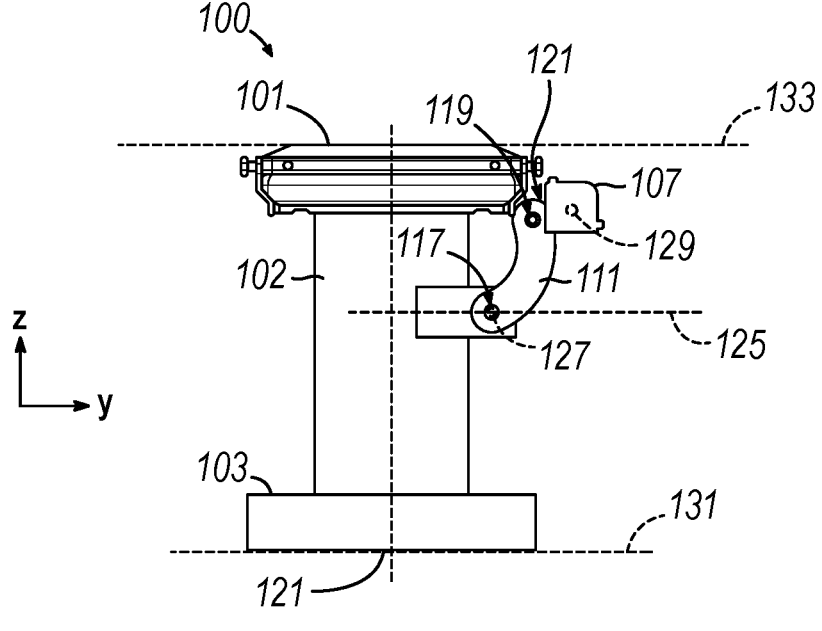
FIG. 13 depicts an end view of the table-based robotic system of FIG. 12.

FIGS. 12 and 13 illustrate isometric and end views of an alternative embodiment of a table-based surgical robotics system (100). The surgical robotics system (100) includes one or more adjustable arm supports (105) that can be configured to support one or more robotic arms (see, for example, FIG. 14) relative to a table (101). In the illustrated embodiment, a single adjustable arm support (105) is shown, though an additional arm support can be provided on an opposite side of the table (101). The adjustable arm support (105) can be configured so that it can move relative to the table (101) to adjust and/or vary the position of the adjustable arm support (105) and/or any robotic arms mounted thereto relative to the table (101). For example, the adjustable arm support (105) may be adjusted one or more degrees of freedom relative to the table (101). The adjustable arm support (105) provides high versatility to the system (100), including the ability to easily stow the one or more adjustable arm supports (105) and any robotics arms attached thereto beneath the table (101). The adjustable arm support (105) can be elevated from the stowed position to a position below an upper surface of the table (101). In other embodiments, the adjustable arm support (105) can be elevated from the stowed position to a position above an upper surface of the table (101).

The adjustable arm support (105) can provide several degrees of freedom, including lift, lateral translation, tilt, etc. In the illustrated embodiment of FIGS. 12 and 13, the arm support (105) is configured with four degrees of freedom, which are illustrated with arrows in FIG. 12. A first degree of freedom allows for adjustment of the adjustable arm support (105) in the z-direction ("Z-lift"). For example, the adjustable arm support (105) can include a carriage (109) configured to move up or down along or relative to a column (102) supporting the table (101). A second degree of freedom can allow the adjustable arm support (105) to tilt. For example, the adjustable arm support (105) can include a rotary joint, which can allow the adjustable arm support (105) to be aligned with the bed in a Trendelenburg position. A third degree of freedom can allow the adjustable arm support (105) to "pivot up," which can be used to adjust a distance between a side of the table (101) and the adjustable arm support (105). A fourth degree of freedom can permit translation of the adjustable arm support (105) along a longitudinal length of the table.

The surgical robotics system (100) in FIGS. 12 and 13 can comprise a table supported by a column (102) that is mounted to a base (103). The base (103) and the column (102) support the table (101) relative to a support surface. A floor axis (131) and a support axis (133) are shown in FIG. 13.

The adjustable arm support (105) can be mounted to the column (102). In other embodiments, the arm support (105) can be mounted to the table (101) or base (103). The adjustable arm support (105) can include a carriage (109), a bar or rail connector (111) and a bar or rail (107). In some embodiments, one or more robotic arms mounted to the rail (107) can translate and move relative to one another.

The carriage (109) can be attached to the column (102) by a first joint (113), which allows the carriage (109) to move relative to the column (102) (e.g., such as up and down a first or vertical axis 123). The first joint (113) can provide the first degree of freedom ("Z-lift") to the adjustable arm support (105). The adjustable arm support (105) can include a second joint 115, which provides the second degree of freedom (tilt) for the adjustable arm support (105). The adjustable arm support (105) can include a third joint (117), which can provide the third degree of freedom ("pivot up") for the adjustable arm support (105). An additional joint (119) (shown in FIG. 13) can be provided that mechanically constrains the third joint (117) to maintain an orientation of the rail (107) as the rail connector (111) is rotated about a third axis (127). The adjustable arm support (105) can include a fourth joint (121), which can provide a fourth degree of freedom (translation) for the adjustable arm support (105) along a fourth axis (129).

Figure 14:
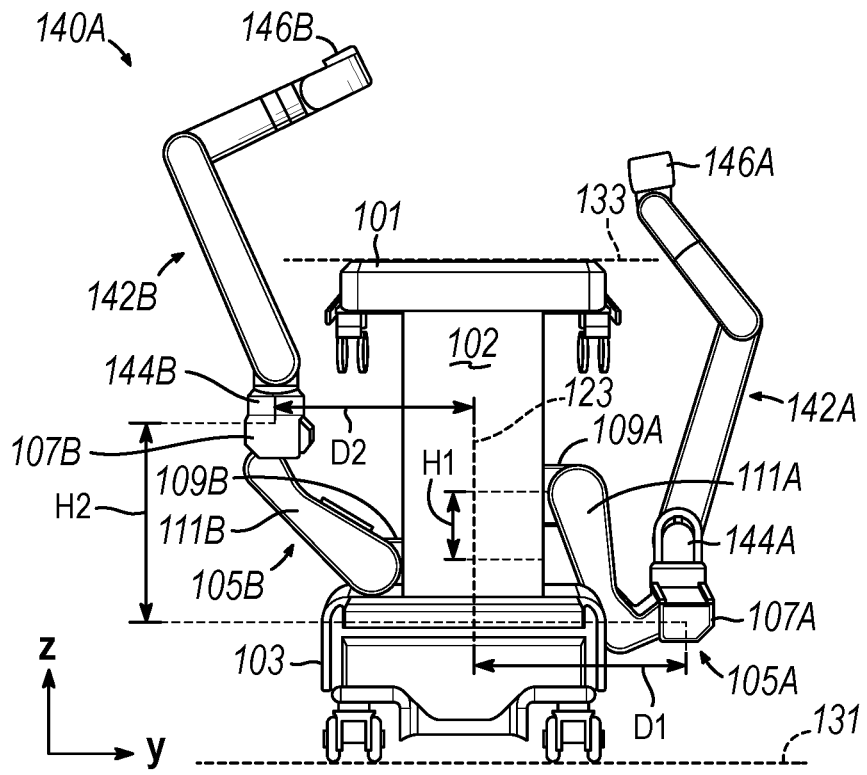
FIG. 14 depicts an end view of a table-based robotic system with robotic arms attached thereto.

FIG. 14 illustrates an end view of the surgical robotics system (140A) with two adjustable arm supports (105A, 105B) mounted on opposite sides of a table (101). A first robotic arm (142A) is attached to the bar or rail (107A) of the first adjustable arm support (105B). The first robotic arm (142A) includes a base (144A) attached to the rail (107A). The distal end of the first robotic arm (142A) includes an instrument drive mechanism (146A) that can attach to one or more robotic medical instruments or tools. Similarly, the second robotic arm (142B) includes a base (144B) attached to the rail (107B). The distal end of the second robotic arm (142B) includes an instrument drive mechanism (146B). The instrument drive mechanism (146B) can be configured to attach to one or more robotic medical instruments or tools.

In some embodiments, one or more of the robotic arms (142A, 142B) comprises an arm with seven or more degrees of freedom. In some embodiments, one or more of the robotic arms (142A, 142B) can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (144A, 144B) (1-degree of freedom including translation). In some embodiments, the insertion degree of freedom can be provided by the robotic arm (142A, 142B), while in other embodiments, the instrument itself provides insertion via an instrument-based insertion architecture.

C. Example of Robotic System Instrument Driver & Interface

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
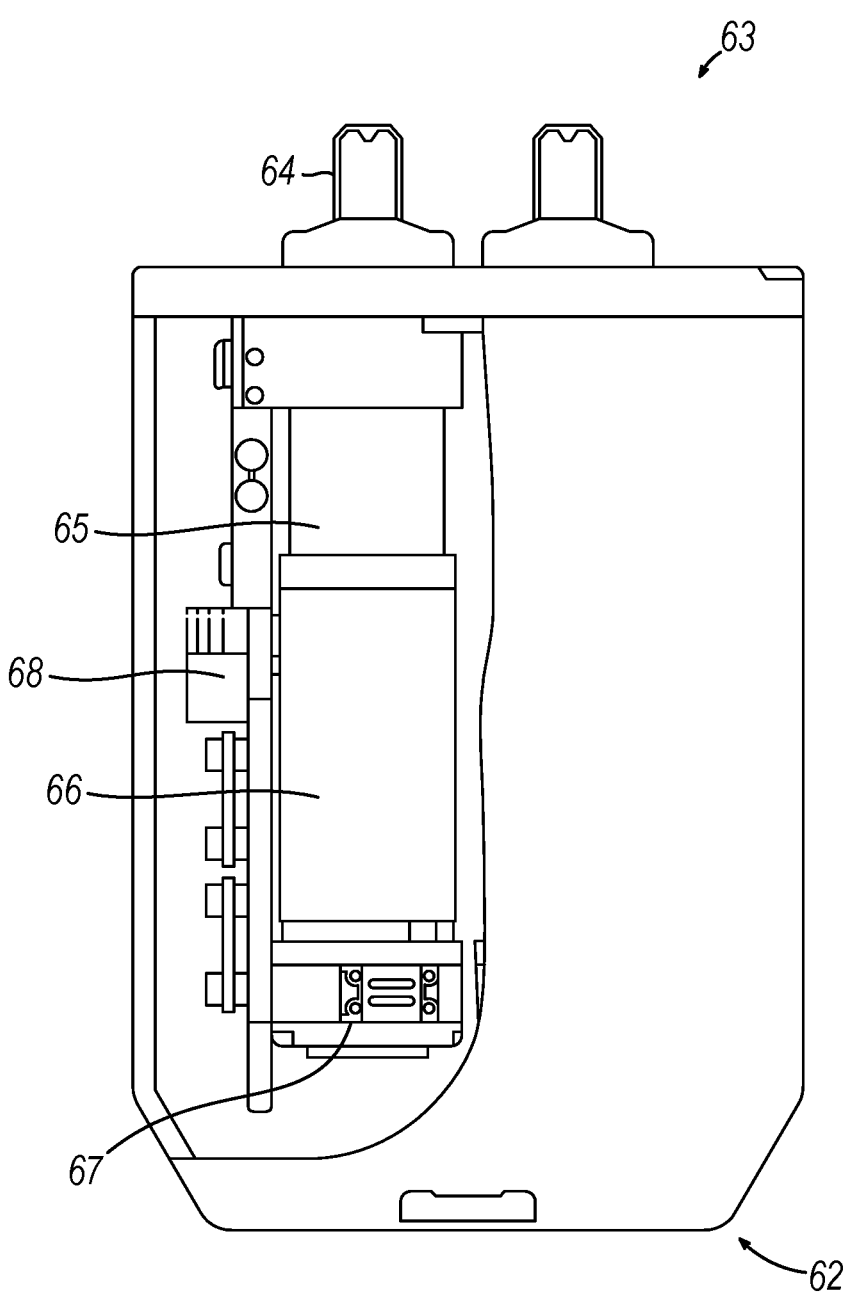
FIG. 15 depicts an exemplary instrument driver.

FIG. 15 illustrates an example instrument driver. Positioned at the distal end of a robotic arm, instrument driver (62) comprises of one or more drive units (63) arranged with parallel axes to provide controlled torque to a medical instrument via drive shafts (64). Each drive unit (63) comprises an individual drive shaft (64) for interacting with the instrument, a gear head (65) for converting the motor shaft rotation to a desired torque, a motor (66) for generating the drive torque, an encoder (67) to measure the speed of the motor shaft and provide feedback to the control circuitry, and control circuitry (68) for receiving control signals and actuating the drive unit. Each drive unit (63) being independent controlled and motorized, the instrument driver (62) may provide multiple (four as shown in FIG. 15) independent drive outputs to the medical instrument. In operation, the control circuitry (68) would receive a control signal, transmit a motor signal to the motor (66), compare the resulting motor speed as measured by the encoder (67) with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Example of Robotic System Medical Instrument

Figure 16:
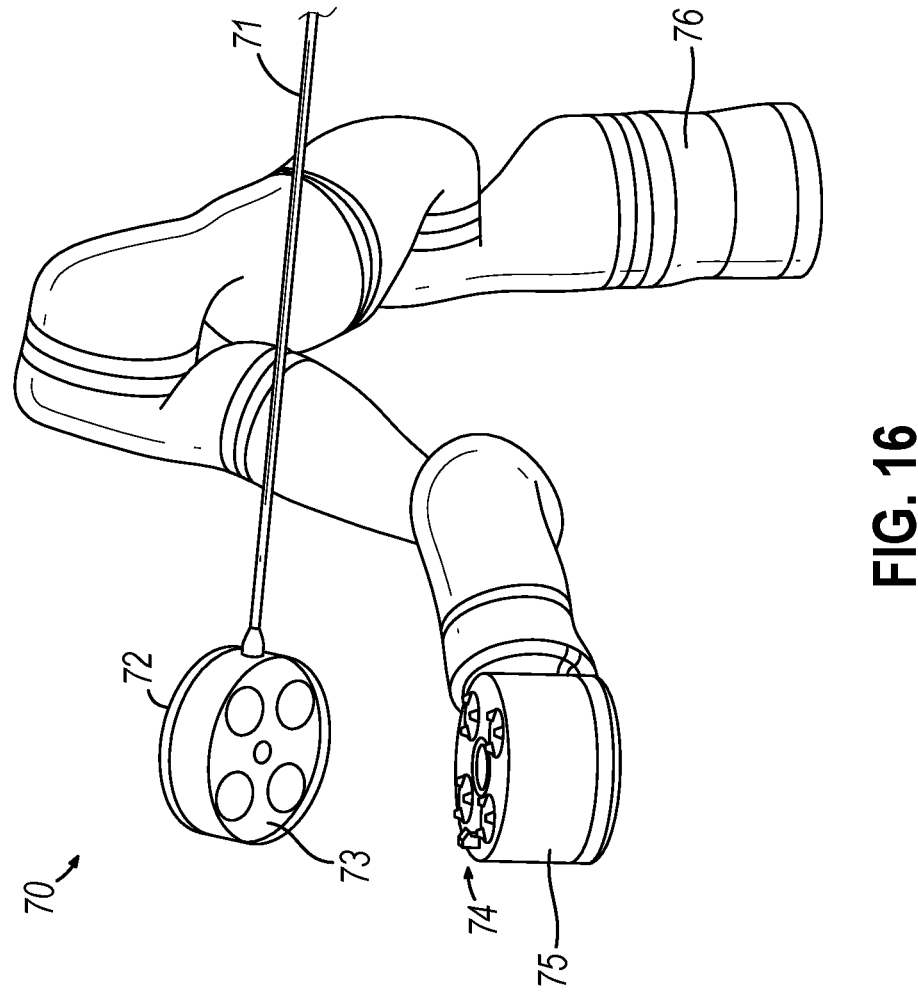
FIG. 16 depicts an exemplary medical instrument with a paired instrument driver.

FIG. 16 illustrates an example medical instrument with a paired instrument driver. Like other instruments designed for use with a robotic system, medical instrument (70) comprises an elongated shaft (71) (or elongate body) and an instrument base (72). The instrument base (72), also referred to as an "instrument handle" due to its intended design for manual interaction by the physician, may generally comprise rotatable drive inputs (73), e.g., receptacles, pulleys or spools, that are designed to be mated with drive outputs (74) that extend through a drive interface on instrument driver (75) at the distal end of robotic arm (76). When physically connected, latched, and/or coupled, the mated drive inputs (73) of instrument base (72) may share axes of rotation with the drive outputs (74) in the instrument driver (75) to allow the transfer of torque from drive outputs (74) to drive inputs (73). In some embodiments, the drive outputs (74) may comprise splines that are designed to mate with receptacles on the drive inputs (73).

The elongated shaft (71) is designed to be delivered through either an anatomical opening or lumen, e.g., as in endoscopy, or a minimally invasive incision, e.g., as in laparoscopy. The elongated shaft (71) may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs (74) of the instrument driver (75). When designed for endoscopy, the distal end of a flexible elongated shaft may include a steerable or controllable bending section that may be articulated and bent based on torque received from the drive outputs (74) of the instrument driver (75).

Torque from the instrument driver (75) is transmitted down the elongated shaft (71) using tendons along the shaft (71). These individual tendons, such as pull wires, may be individually anchored to individual drive inputs (73) within the instrument handle (72). From the handle (72), the tendons are directed down one or more pull lumens along the elongated shaft (71) and anchored at the distal portion of the elongated shaft (71), or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs (73) would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft (71), where tension from the tendon cause the grasper to close.

In endoscopy, the tendons may be coupled to a bending or articulating section positioned along the elongated shaft (71) (e.g., at the distal end) via adhesive, control ring, or other mechanical fixation. When fixedly attached to the distal end of a bending section, torque exerted on drive inputs (73) would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft (71) to allow for controlled articulation in the desired bending or articulable sections.

In endoscopy, the elongated shaft (71) houses a number of components to assist with the robotic procedure. The shaft may comprise of a working channel for deploying surgical tools (or medical instruments), irrigation, and/or aspiration to the operative region at the distal end of the shaft (71). The shaft (71) may also accommodate wires and/or optical fibers to transfer signals to/from an optical assembly at the distal tip, which may include of an optical camera. The shaft (71) may also accommodate optical fibers to carry light from proximally-located light sources, such as light emitting diodes, to the distal end of the shaft.

At the distal end of the instrument (70), the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft (71). Rolling the elongated shaft (71) along its axis while keeping the drive inputs (73) static results in undesirable tangling of the tendons as they extend off the drive inputs (73) and enter pull lumens within the elongated shaft (71). The resulting entanglement of such tendons may disrupt any control algorithms intended to predict movement of the flexible elongated shaft during an endoscopic procedure.

Figure 17:
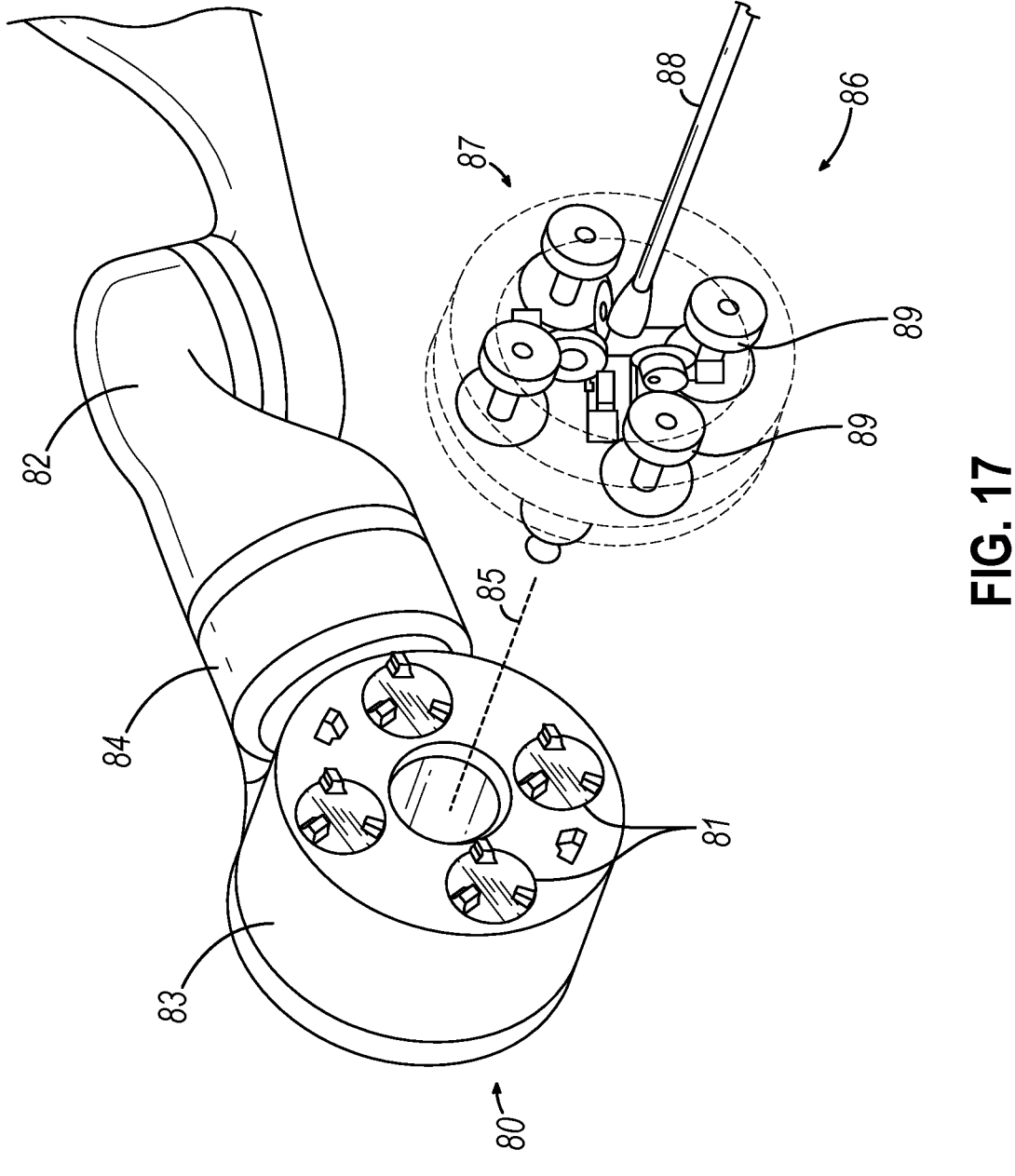
FIG. 17 depicts an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver (80) comprises four drive units with their drive outputs (81) aligned in parallel at the end of a robotic arm (82). The drive units, and their respective drive outputs (81), are housed in a rotational assembly (83) of the instrument driver (80) that is driven by one of the drive units within the assembly (83). In response to torque provided by the rotational drive unit, the rotational assembly (83) rotates along a circular bearing that connects the rotational assembly (83) to the non-rotational portion (84) of the instrument driver. Power and controls signals may be communicated from the non-rotational portion (84) of the instrument driver (80) to the rotational assembly (83) through electrical contacts may be maintained through rotation by a brushed slip ring connection (not shown). In other embodiments, the rotational assembly (83) may be responsive to a separate drive unit that is integrated into the non-rotatable portion (84), and thus not in parallel to the other drive units. The rotational assembly (83) allows the instrument driver (80) to rotate the drive units, and their respective drive outputs (81), as a single unit around an instrument driver axis (85).

Like earlier disclosed embodiments, an instrument 86 may comprise an elongated shaft portion (88) and an instrument base (87) (shown with a transparent external skin for discussion purposes) comprising a plurality of drive inputs (89) (such as receptacles, pulleys, and spools) that are configured to receive the drive outputs (81) in the instrument driver (80). Unlike prior disclosed embodiments, instrument shaft (88) extends from the center of instrument base (87) with an axis substantially parallel to the axes of the drive inputs (89), rather than orthogonal as in the design of FIG. 16.

When coupled to the rotational assembly (83) of the instrument driver (80), the medical instrument 86, comprising instrument base (87) and instrument shaft (88), rotates in combination with the rotational assembly (83) about the instrument driver axis (85). Since the instrument shaft (88) is positioned at the center of instrument base (87), the instrument shaft (88) is coaxial with instrument driver axis (85) when attached. Thus, rotation of the rotational assembly (83) causes the instrument shaft (88) to rotate about its own longitudinal axis. Moreover, as the instrument base (87) rotates with the instrument shaft (88), any tendons connected to the drive inputs (89) in the instrument base (87) are not tangled during rotation. Accordingly, the parallelism of the axes of the drive outputs (81), drive inputs (89), and instrument shaft (88) allows for the shaft rotation without tangling any control tendons.

Figure 18:
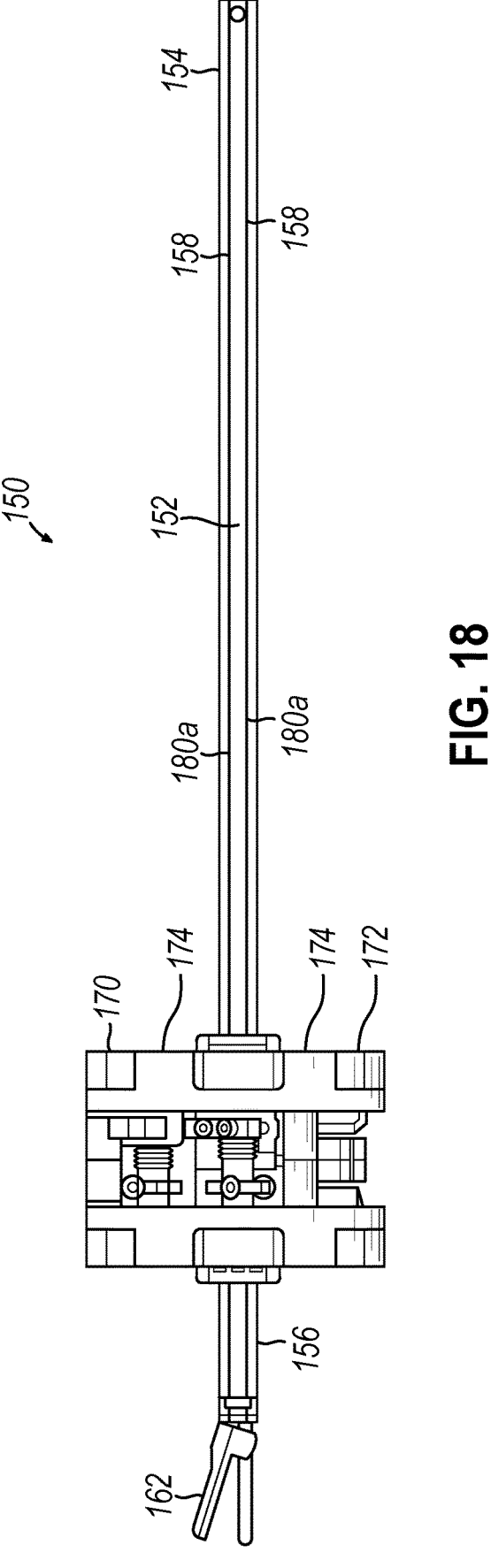
FIG. 18 depicts an instrument having an instrument-based insertion architecture.

FIG. 18 illustrates an instrument having an instrument based insertion architecture in accordance with some embodiments. The instrument (150) can be coupled to any of the instrument drivers discussed above. The instrument (150) comprises an elongated shaft (152), an end effector (162) connected to the shaft (152), and a handle (170) coupled to the shaft (152). The elongated shaft (152) comprises a tubular member having a proximal portion (154) and a distal portion (156). The elongated shaft (152) comprises one or more channels or grooves (158) along its outer surface. The grooves (158) are configured to receive one or more wires or cables (180) therethrough. One or more cables (180) thus run along an outer surface of the elongated shaft (152). In other embodiments, cables (180) can also run through the elongated shaft (152). Manipulation of the one or more cables (180) (e.g., via an instrument driver) results in actuation of the end effector (162).

The instrument handle (170), which may also be referred to as an instrument base, may generally comprise an attachment interface (172) having one or more mechanical inputs (174), e.g., receptacles, pulleys or spools, that are designed to be reciprocally mated with one or more torque couplers on an attachment surface of an instrument driver.

In some embodiments, the instrument (150) comprises a series of pulleys or cables that enable the elongated shaft (152) to translate relative to the handle (170). In other words, the instrument (150) itself comprises an instrument-based insertion architecture that accommodates insertion of the instrument, thereby minimizing the reliance on a robot arm to provide insertion of the instrument (150). In other embodiments, a robotic arm can be largely responsible for instrument insertion.

E. Example of Robotic System Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
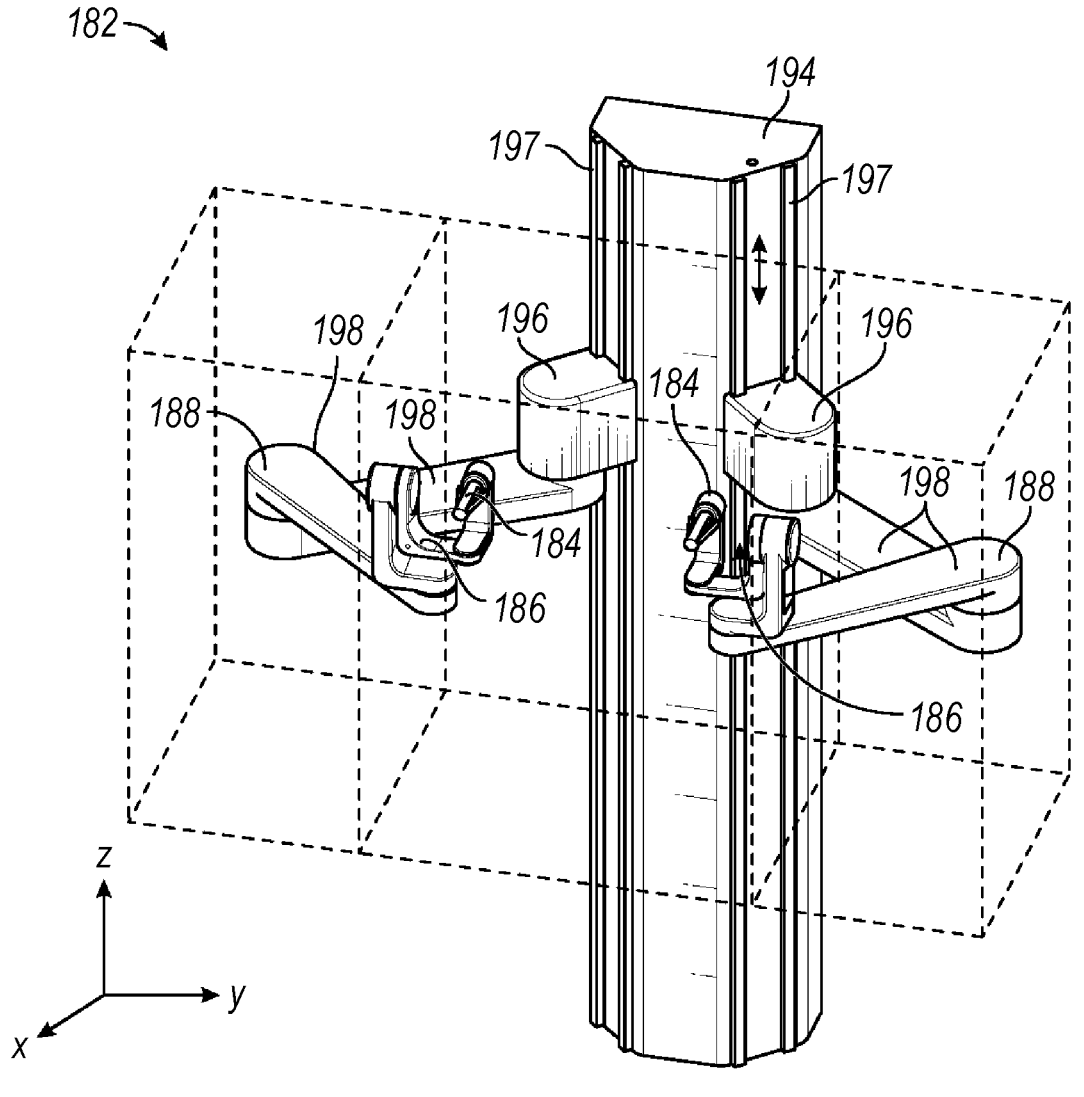
FIG. 19 depicts an exemplary controller.

FIG. 19 is a perspective view of an embodiment of a controller (182). In the present embodiment, the controller (182) comprises a hybrid controller that can have both impedance and admittance control. In other embodiments, the controller (182) can utilize just impedance or passive control. In other embodiments, the controller (182) can utilize just admittance control. By being a hybrid controller, the controller (182) advantageously can have a lower perceived inertia while in use.

In the illustrated embodiment, the controller (182) is configured to allow manipulation of two medical instruments, and includes two handles (184). Each of the handles (184) is connected to a gimbal (186). Each gimbal (186) is connected to a positioning platform (188).

As shown in FIG. 19, each positioning platform (188) includes a SCARA arm (selective compliance assembly robot arm) (198) coupled to a column (194) by a prismatic joint (196). The prismatic joints (196) are configured to translate along the column (194) (e.g., along rails (197)) to allow each of the handles (184) to be translated in the z-direction, providing a first degree of freedom. The SCARA arm (198) is configured to allow motion of the handle (184) in an x-y plane, providing two additional degrees of freedom.

In some embodiments, one or more load cells are positioned in the controller. For example, in some embodiments, a load cell (not shown) is positioned in the body of each of the gimbals (186). By providing a load cell, portions of the controller (182) are capable of operating under admittance control, thereby advantageously reducing the perceived inertia of the controller while in use. In some embodiments, the positioning platform (188) is configured for admittance control, while the gimbal (186) is configured for impedance control. In other embodiments, the gimbal (186) is configured for admittance control, while the positioning platform (188) is configured for impedance control. Accordingly, for some embodiments, the translational or positional degrees of freedom of the positioning platform (188) can rely on admittance control, while the rotational degrees of freedom of the gimbal (186) rely on impedance control.

F. Example of Robotic System Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
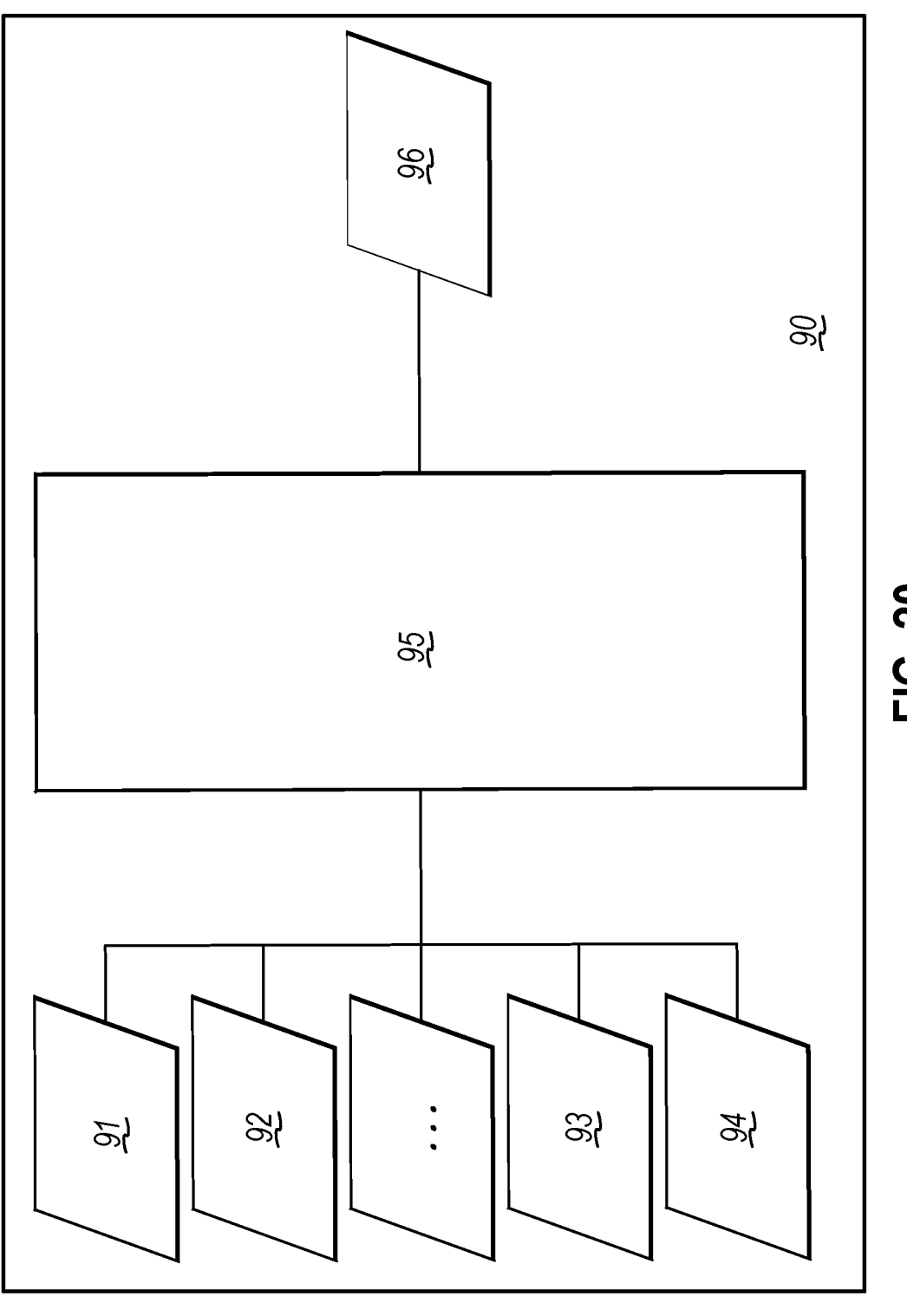
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system (90) that estimates a location of one or more elements of the robotic system, such as the location of the instrument, in accordance to an example embodiment. The localization system (90) may be a set of one or more computer devices configured to execute one or more instructions. The computer devices may be embodied by a processor (or processors) and computer-readable memory in one or more components discussed above. By way of example and not limitation, the computer devices may be in the tower (30) shown in FIG. 1, the cart shown in FIGS. 1-4, the beds shown in FIGS. 5-14, etc.

As shown in FIG. 20, the localization system (90) may include a localization module (95) that processes input data (91-94) to generate location data (96) for the distal tip of a medical instrument. The location data (96) may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data (91-94) are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data (91) (also referred to as "preoperative model data" when generated using only preoperative CT scans). The use of center-line geometry is discussed in U.S. Pat. No. 9,763,741, the contents of which are herein incorporated in its entirety. Network topological models may also be derived from the CT-images, and are particularly appropriate for bronchoscopy.

In some embodiments, the instrument may be equipped with a camera to provide vision data (92). The localization module (95) may process the vision data to enable one or more vision-based location tracking. For example, the pre-operative model data may be used in conjunction with the vision data (92) to enable computer vision-based tracking of the medical instrument (e.g., an endoscope or an instrument advance through a working channel of the endoscope). For example, using the preoperative model data (91), the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module (95) may identify circular geometries in the preoperative model data (91) that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data (92) to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module (95) may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data (93). The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data (94) may also be used by the localization module (95) to provide localization data (96) for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module (95). For example, although not shown in FIG. 20, an instrument utilizing shape-sensing fiber can provide shape data that the localization module (95) can use to determine the location and shape of the instrument.

The localization module (95) may use the input data (91-94) in combination(s). In some cases, such a combination may use a probabilistic approach where the localization module (95) assigns a confidence weight to the location determined from each of the input data (91-94). Thus, where the EM data may not be reliable (as may be the case where there is EM interference) the confidence of the location determined by the EM data (93) can be decrease and the localization module (95) may rely more heavily on the vision data (92) and/or the robotic command and kinematics data (94).

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

II. Example of Robotically Controlled Uterine Manipulator

In some conventional hysterectomy procedures, a first clinician may serve in a role of forming incisions and performing other laparoscopic operations to remove the uterus of a patient, while a second clinician may serve in a role of manipulating the position and orientation uterus of the patient to facilitate the operations being performed by the first clinician. Such team-based procedures may require clear communication between the first clinician and the second clinician, with the first clinician instructing the second clinician on desired positioning and orientation of the uterus, and with the second clinician responding in a timely and accurate fashion. In some scenarios, such communications may break down or otherwise yield undesirable results, such as the second clinician not precisely positioning or orienting the uterus when and where the first clinician wishes. It may therefore be desirable to provide a robotic system that is capable of performing at least part of the role of the second clinician, such that the robotic system may at least partially control the position and orientation of the uterus based on the desire of the first clinician. Examples of how a robotic system may provide uterine manipulation are described in greater detail below. The following examples may be readily incorporated into any of the various robotic systems (10, 36, 47, 100, 140A) described herein; or in any other suitable robotic system.

Figure 21:
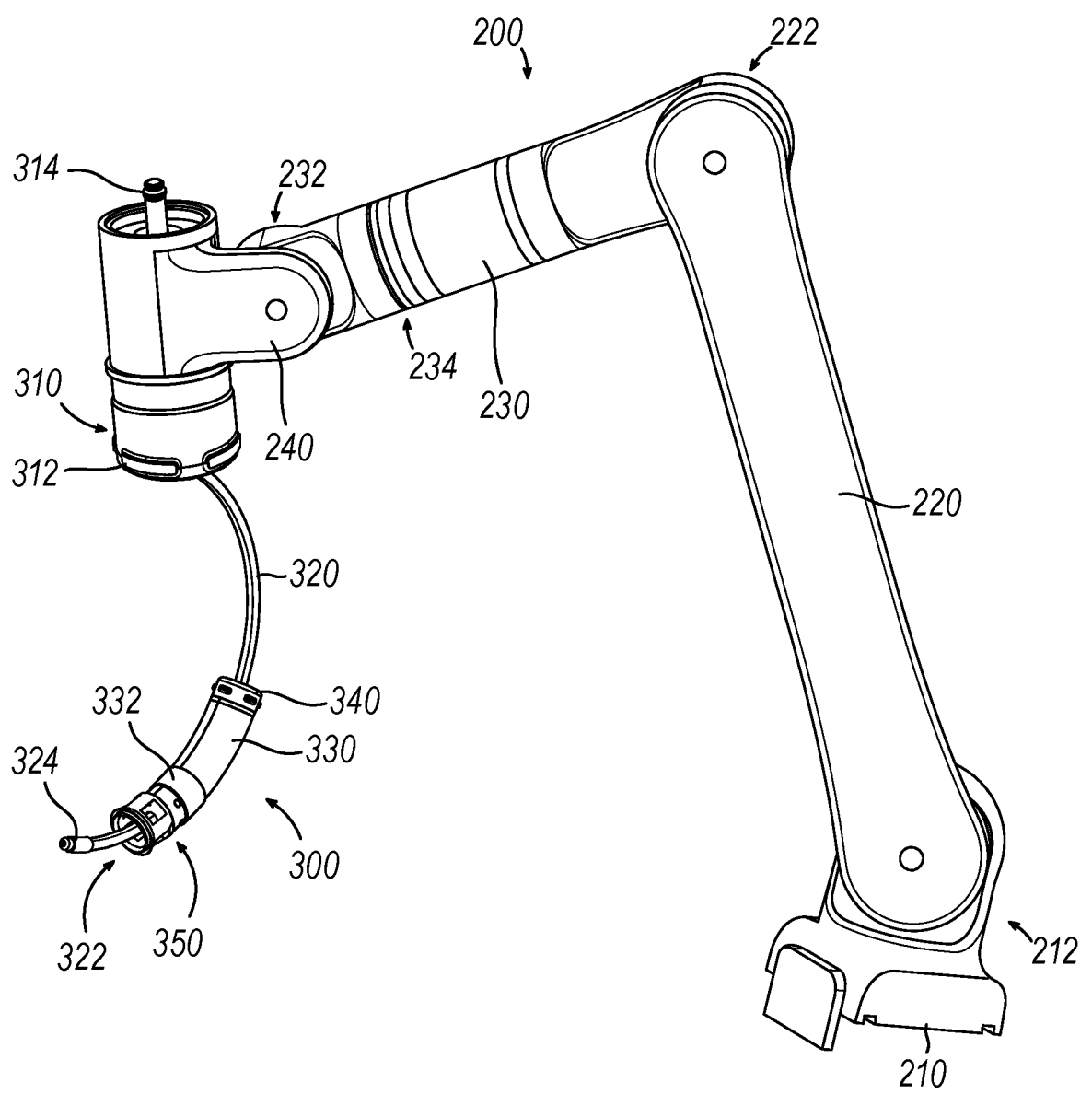
FIG. 21 depicts a perspective view of an example of a robotic arm with a uterine manipulator instrument.

FIG. 21 shows an example of a uterine manipulator (300) secured to a robotic arm (200). Robotic arm (200) of this example includes a mount (210), arm segments (220, 230), a plurality of joints (212, 222, 234, 232), and a head (240). Mount (210) is configured to couple with a component of a robotic system (10, 36, 47, 100, 140A) for support. For instance, mount (210) may be coupled with carriage interface (19), carriage (43), rail (197), or any other suitable structure. In some versions, base (210) is operable to translate along the structure to which base (210) is secured, to thereby assist in positioning robotic arm (200) in relation to a patient and/or to otherwise position robotic arm (200). One end of arm segment (220) is pivotably coupled to base (210) via joint (212), such that arm segment (220) is pivotable relative to base (210) at joint (212). The other end of arm segment (220) is pivotably coupled to an end of arm segment (230) via joint (222), such that arm segment (230) is pivotable relative to arm segment (220) at joint (222). The other end of arm segment (230) is coupled with joint (232) via joint (234). Joint (234) is configured to allow joint (232) and head (240) to rotate relative to arm segment (230) about the longitudinal axis of arm segment (230). In some variations, a similar kind of joint is provided in arm segment (220), such that arm segment (220) may be effectively broken into two segments where one of those segments is rotatable relative to the other about the longitudinal axes of those two segments. Head (240) is pivotably coupled with joint (234) via joint (232), such that head (240) is pivotable relative to joint (234) at joint (232). Motion at any of joints (212, 222, 234, 232) may be driven robotically via motors, solenoids, and/or any other suitable source(s) of motion.

Figure 22:
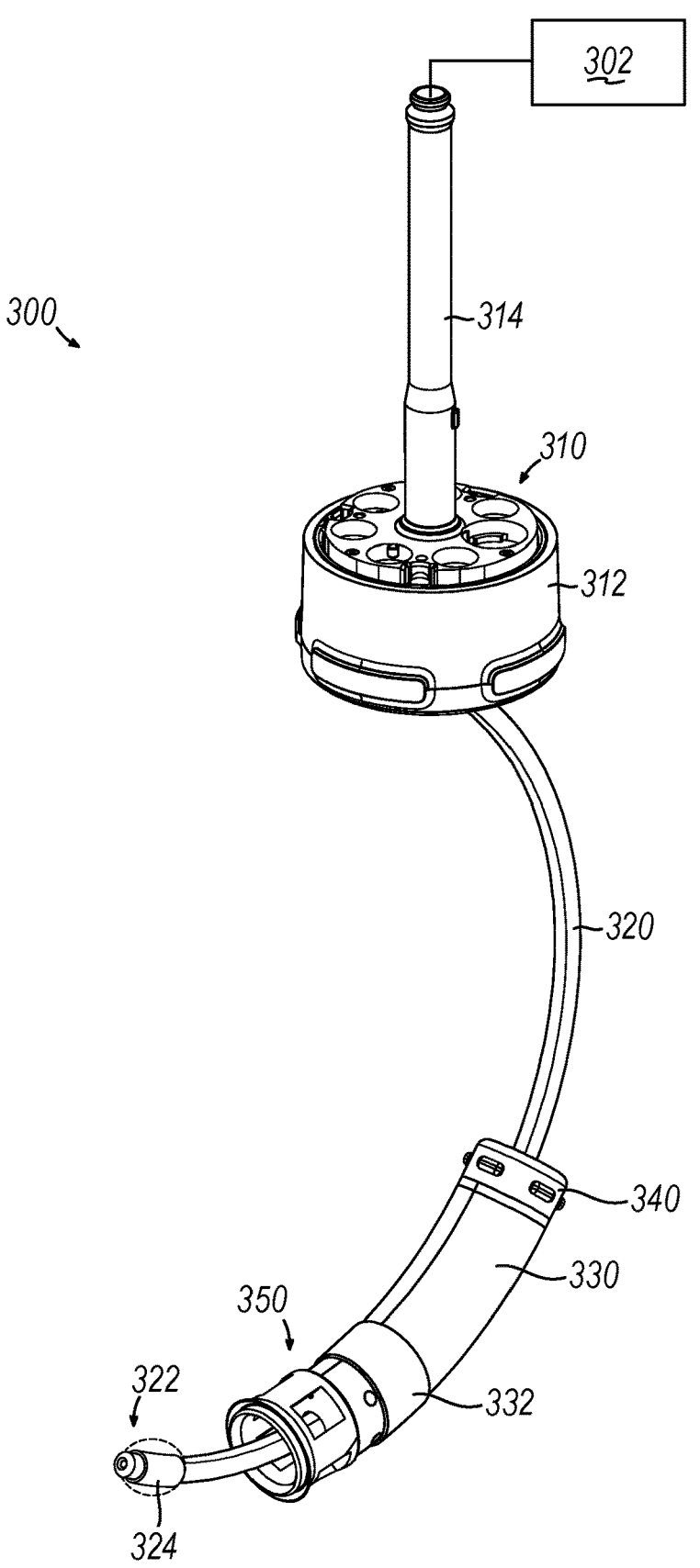
FIG. 22 depicts a perspective view of the uterine manipulator instrument of FIG. 21.

Uterine manipulator (300) is removably coupled with head (240), such that robotic arm (200) may selectively position and orient uterine manipulator in relation to a patient by driving robotic arm (200). As best seen in FIG. 22, uterine manipulator (300) of the present example includes a head interface assembly (310), a shaft (320), a sleeve (330), a sleeve locking ring (340), and a colpotomy cup (350). Head interface assembly (310) includes a base (312) and a shaft (314). Base (312) is configured to removably couple with head (240) to thereby secure uterine manipulator (300) with head (240). By way of example only, base (312) and head (240) may include complementary bayonet fitting features, complementary threading, complementary snap-fit features, and/or any other suitable kinds of structures to provide a removable coupling. Shaft (320) is configured to couple with a pressurized fluid source (302). Pressurized fluid source (302) may contain pressurized air, pressurized saline, or any other suitable kind of pressurized fluid. The pressurized fluid may be used to selectively inflate balloons (324, 332), which will be described in greater detail below.

Shaft (320) of the present example extends distally from base (312) along a curve. In some versions, shaft (320) is rigid. In some other versions, shaft (320) is flexible yet resiliently biased to assume the curved configuration shown. Any suitable biocompatible material(s) may be used to form shaft (320), including but not limited to metallic materials, plastic materials, and combinations thereof. An inflatable balloon (324) is positioned near distal end (322) of shaft (320). Balloon (324) may be formed of an extensible material or a non-extensible material. The interior of shaft (320) includes one or more lumen(s) that are configured to communicate pressurized fluid from pressurized fluid source (302) to balloon (324). While balloon (324) is positioned near distal end (322) of shaft (320) in the present example, other versions may include a different kind of expandable member. By way of example only, an alternative expandable member may include a mechanically expandable component such as an expandable mesh structure, an expanding umbrella-like structure, or any other suitable kind of expandable structure or assembly. In some versions, distal end (322) of shaft (320) may also include an illuminating element (e.g., one or more LEDs, a lens illuminated by one or more optical fibers, etc.). In such versions, one or more wires, optical fibers, and/or other components may extend along the length of shaft (320) to couple with a source of electrical power, a source of light, etc.

Sleeve (330) is slidably coupled to shaft (320), such that sleeve (330) may slide along shaft (320) from a proximal position (FIGS. 25B-25C) to any number of distal positions (FIGS. 21, 22, 25D-25E). Sleeve (330) is generally cylindraceous and rigid; and extends along a curved axis such that the curved lateral profile complements the curved lateral profile of shaft (320). Sleeve (330) may be formed of plastic, metal, and/or any other suitable biocompatible material(s), including combinations of materials. Locking ring (340) is rotatably secured to the proximal end of sleeve (330), while colpotomy cup (350) is fixedly secured to the distal end of sleeve (330). An inflatable balloon (332) is positioned along sleeve (330), between locking ring (340) and colpotomy cup (350). Balloon (332) may be formed of an extensible material or a non-extensible material. The interior of sleeve (330) includes one or more lumen(s) that are configured to communicate pressurized fluid from pressurized fluid source (302) to balloon (332). Such a lumen or lumens may be coupled with pressurized fluid source (302) via a flexible tube (not shown). In some versions, one or more lumens or tubes within shaft (320) provide at least part of the fluid pathway between balloon (332) and pressurized fluid source (302).

Locking ring (340) is operable to selectively secure the position of sleeve (330) along the length of shaft (320). For instance, locking ring (340) may be rotated to a first angular position relative to sleeve (330) to provide an unlocked state where sleeve (330) may be freely translated along shaft (320). Locking ring (340) may then be rotated to a second angular position relative to sleeve (330) to provide a locked state where the position of sleeve (330) along shaft (320) is secured until locking ring (340) is rotated back to the first angular position. By way of example only, locking ring (340) may include one or more frictional braking structures that selectively engage shaft (320) to thereby provide the locked state. Alternatively, locking ring (340) may selectively engage shaft (320) in any other suitable fashion.

Figure 23:
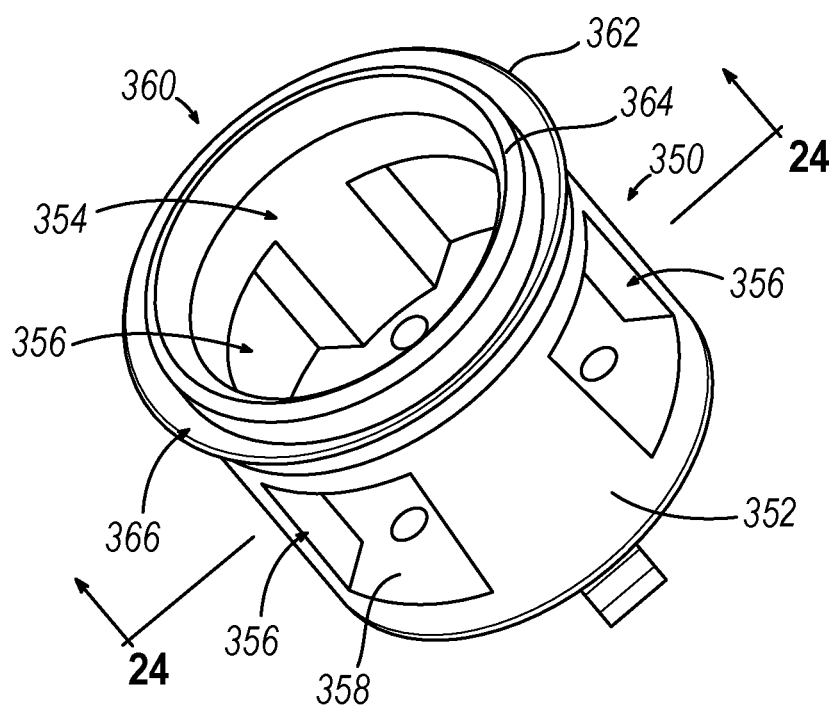
FIG. 23 depicts a perspective view of a colpotomy cup of the uterine manipulator instrument of FIG. 23.
Figure 24:
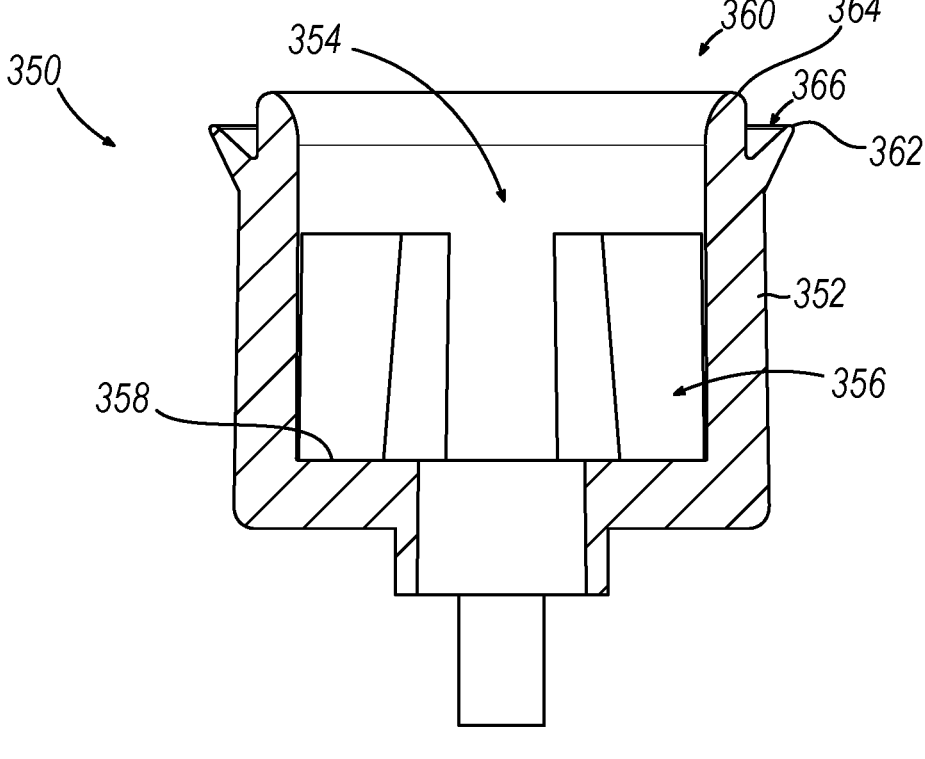
FIG. 24 depicts a cross-sectional side view of the colpotomy cup of FIG. 23.

FIGS. 23-24 show colpotomy cup (350) in greater detail. As shown, colpotomy cup (350) of the present example includes a body (352) defining an interior space (354). Body (352) further includes a floor (358) at the bottom of interior space (354) and an open distal end (360). A plurality of lateral openings (356) are in communication with interior space (354). Distal end (360) includes a distally presented annular edge (364) and an obliquely presented annular edge (362), with a space (366) being defined between edges (362, 364). Space (366) has a V-shaped cross-sectional profile, as best seen in FIG. 24. Colpotomy cup (350) may be formed of plastic, metal, and/or any other suitable biocompatible material(s), including combinations of materials.

Figure 25A:
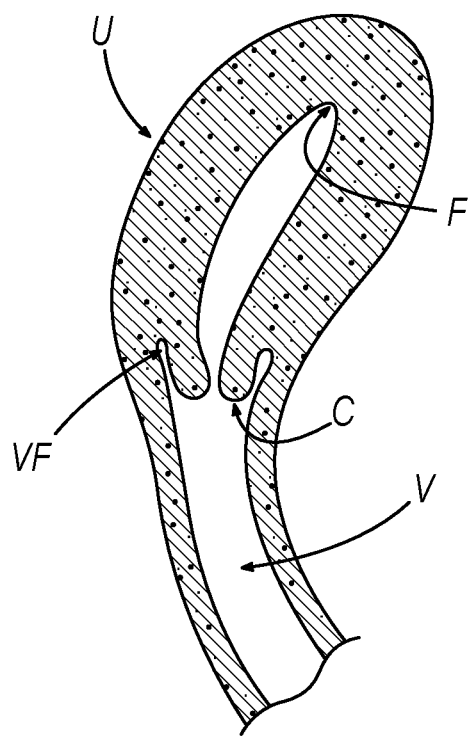
FIG. 25A depicts a mid-sagittal cross-sectional view of a vagina and uterus.
Figure 25B:
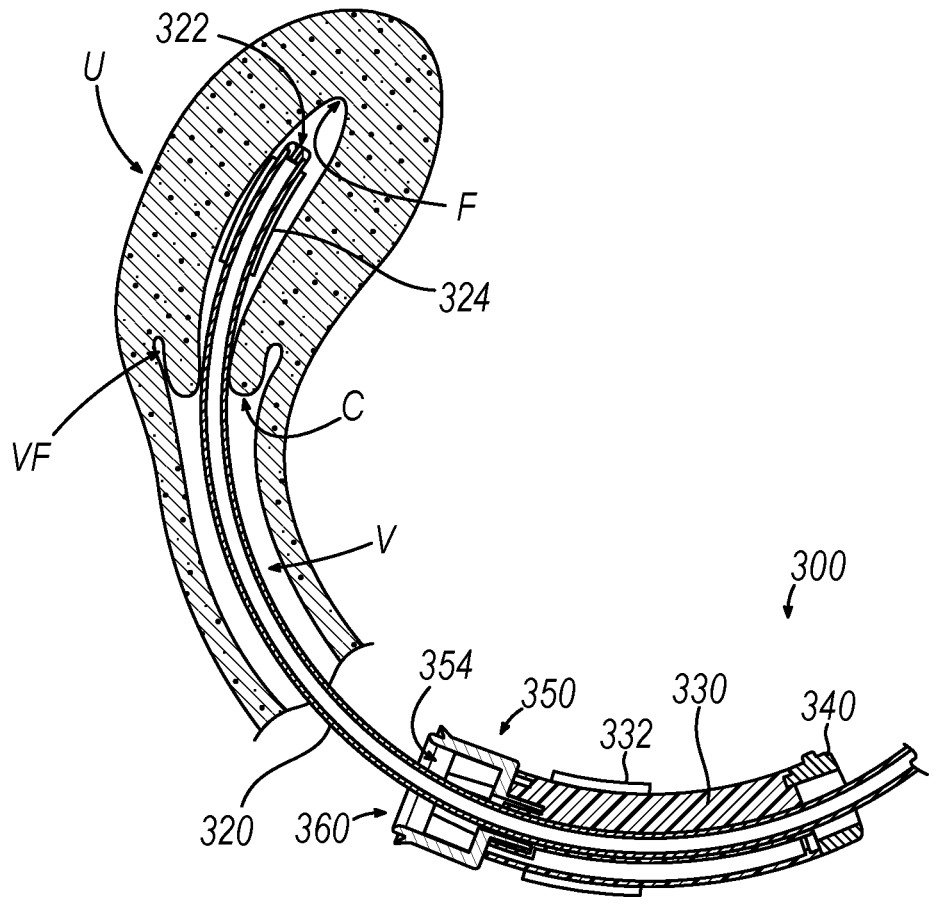
FIG. 25B depicts a mid-sagittal cross-sectional view of the vagina and uterus of FIG. 25A, with the shaft of the uterine manipulator instrument of FIG. 21 inserted through the vagina into the uterus, with a balloon of the uterine manipulator instrument of FIG. 21 in a deflated state, and with a sleeve of the uterine manipulator instrument in a proximal position.

FIGS. 25A-25E show an example of a procedure in which uterine manipulator (300) is used. As shown in FIG. 25A, the anatomical context in which uterine manipulator (300) is used includes a vagina (V) and uterus (U) of a patient. As shown in FIG. 25B, shaft (320) is inserted through the vagina (V) and into the uterus (U) via the cervix (C), while sleeve (330) is in a proximal position along shaft (320). Balloon (324) is in a deflated state during this stage of insertion. In some versions, uterine manipulator (300) is fully decoupled from robotic arm (200) during the process leading up to the stage shown in FIG. 25B, such that uterine manipulator (300) is advanced to this state manually by a human operator grasping a proximal portion of uterine manipulator (300) (e.g., grasping a proximal portion of shaft (320), grasping base (312), and/or grasping some other part of uterine manipulator (300)). In such scenarios, uterine manipulator (300) may be coupled with robotic arm (200) after reaching the stage shown in FIG. 25B.

In some other versions, uterine manipulator (300) is already coupled with robotic arm (200) before reaching the stage shown in FIG. 25B; and robotic arm (200) is used to guide and drive uterine manipulator (300) to the position shown in FIG. 25B. As yet another variation, some versions may allow a human operator to guide and drive uterine manipulator (300) to the position shown in FIG. 25B while uterine manipulator (300) is coupled with robotic arm (200), such that robotic arm (200) does not restrict manual movement of uterine manipulator (300) leading up to the stage shown in FIG. 25B.

Regardless of the stage at which uterine manipulator (300) is coupled with robotic arm (200), robotic arm (200) may be positioned in various suitable ways relative to the patient while uterine manipulator (300) is inserted in the patient. In some scenarios, robotic arm (200) crosses over the top of one of the patient's legs from the side, to assist in positioning uterine manipulator (300). In some other scenarios (e.g., when the patient's legs are supported by stirrups (58)), robotic arm (200) crosses under the bottom of one of the patient's legs from the side, to assist in positioning uterine manipulator (300). In still other scenarios, robotic arm (200) is positioned between the patient's legs from underneath, such that robotic arm (200) does not cross over or under either of the patient's legs. Alternatively, robotic arm (200) may have any other suitable spatial and positional relationship with respect to the patient.

In the present example, uterine manipulator (300) is advanced distally until distal end (322) of shaft (320) reaches the fundus (F) of the uterus (U). The operator may determine that distal end (322) has reached the fundus (F) via tactile feedback (e.g., such that the operator can feel sudden resistance to further advancement of shaft (320)). In addition, or in the alternative, in versions where distal end (322) includes an illuminating element, the illuminating element may provide transillumination through the wall of the uterus (U). Such transillumination may be observed via a laparoscope or other visualization device that is positioned external to the uterus (U). Such transillumination may indicate the extent to which shaft (320) has been inserted into the uterus (U). In some cases where distal end (322) contacts the fundus (F), distal end (322) may remain in contact with fundus (F) throughout the rest of the procedure shown in FIGS. 25B-25E. In some other versions, distal end (322) may be slightly backed out proximally, such that distal end (322) does not contact fundus (F) throughout the rest of the procedure shown in FIGS. 25B-25E.

After reaching the state shown in FIG. 25B, balloon (324) may be inflated as described above; and as shown in FIG. 25C. In some cases, balloon (324) is inflated to a point where balloon (324) bears outwardly against the sidewall of the uterus (U). In any case, the inflated balloon (324) may stabilize the distal portion of shaft (320) relative to the uterus (U). Specifically, the inflated balloon (324) may prevent shaft (320) from exiting proximally from the uterus (U) via the cervix (C). Balloon (324) may thus serve as a distally-positioned anchor structure for uterine manipulator (300). The inflated balloon (324) may also provide sufficient engagement between shaft (320) and the uterus (U) to allow use of shaft (320) to reposition and reorient the uterus (U) as described herein.

Figure 25C:
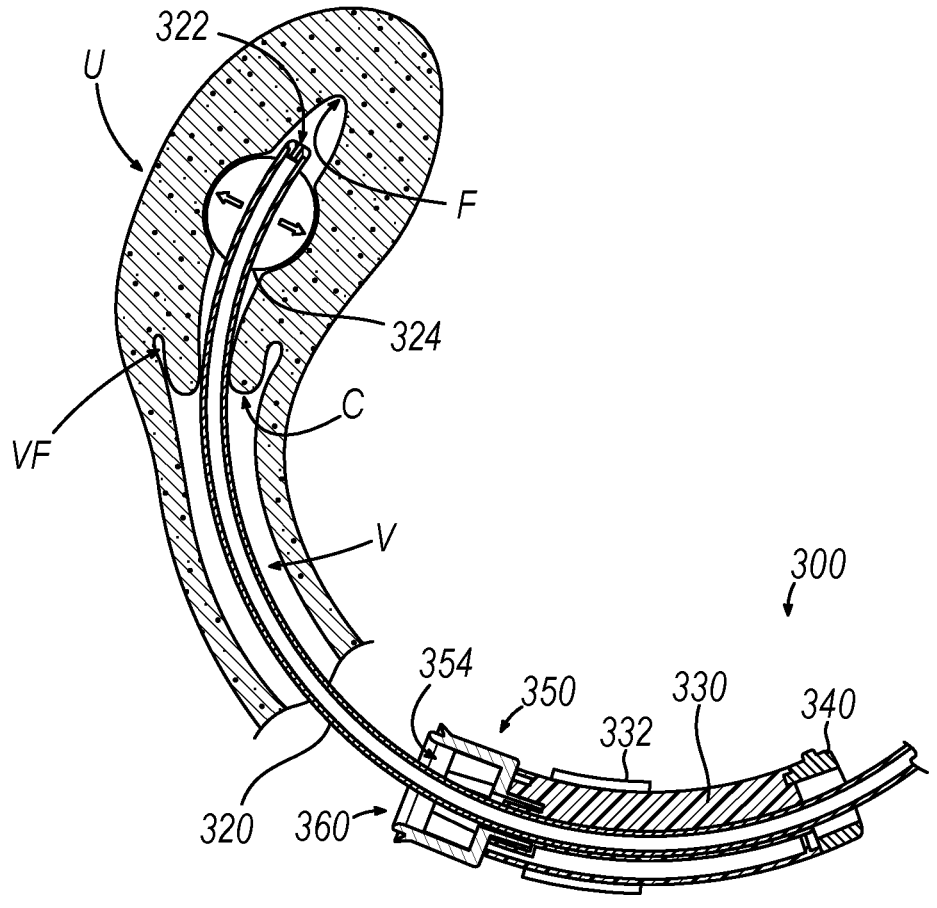
FIG. 25C depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in an inflated state, and with the sleeve of the uterine manipulator instrument in the proximal position.
Figure 25D:
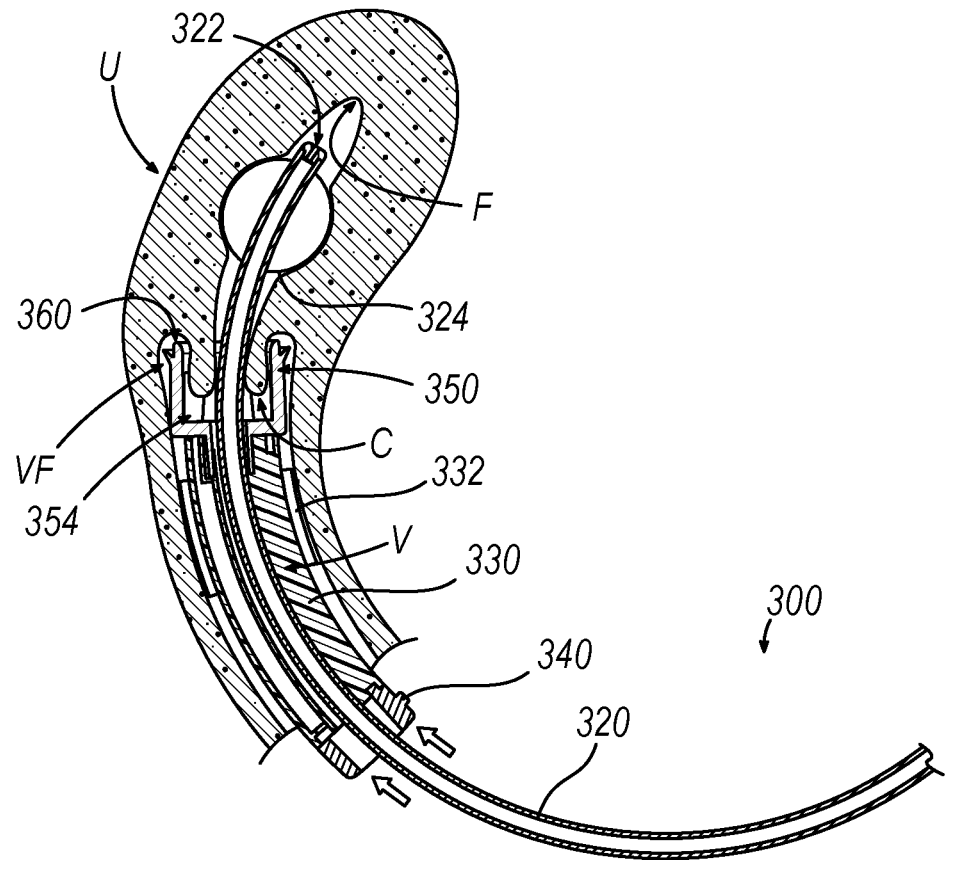
FIG. 25D depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in the inflated state, with the sleeve of the uterine manipulator instrument in a distal position such that the colpotomy cup of the sleeve is engaged with the cervix, and with a balloon of the sleeve in a deflated state.

With balloon (324) in the inflated state the operator may advance sleeve (330) distally along shaft (320) to the position shown in FIG. 25D. In the present example, this is performed by a human operator manually advancing sleeve (330) distally along shaft (320). In some other versions, this may be performed by a robotic operator robotically advancing sleeve (330) distally along shaft (320). As shown, sleeve (330) is advanced distally to a point where distal end (360) is firmly seated in the vaginal fornix (VF). The cervix (C) is received in interior space (354) of body (352). At this stage, the longitudinal position of sleeve (330) along shaft (320) is locked in place via locking ring (340). Specifically, the operator grasps locking ring (340) and rotates locking ring (340) about shaft (320) to firmly lock the position of sleeve (330) along shaft (320). In the present example, this is performed by a human operator, though it may be performed by a robotic operator in other versions. With the position of sleeve (330) locked in place against shaft (320), the position of uterine manipulator (300) is substantially fixed relative to the vagina (V), the cervix (C), and the uterus (U). While balloon (324) serves as a distally-positioned anchor structure for uterine manipulator (300), colpotomy cup (350) serves as a proximally-positioned anchor structure for uterine manipulator (300).

Figure 25E:
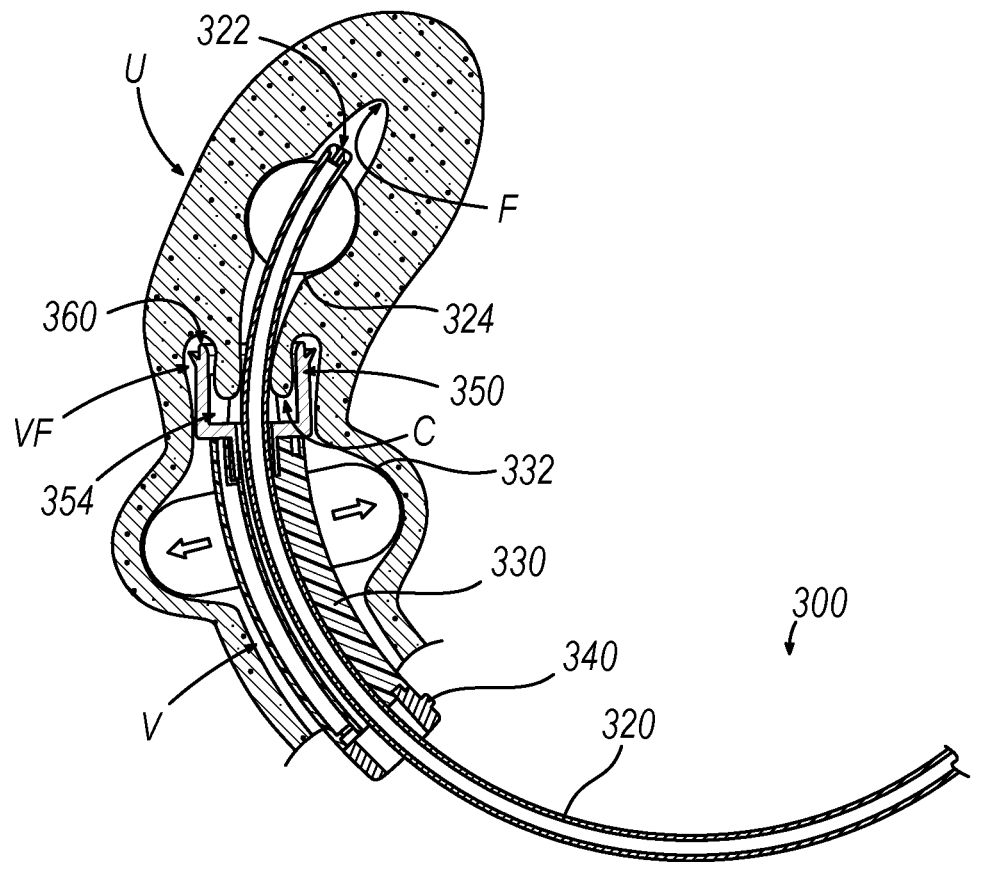
FIG. 25E depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in the inflated state, with the sleeve of the uterine manipulator instrument in the distal position such that the colpotomy cup of the sleeve is engaged with the cervix, and with the balloon of the sleeve in an inflated state.

With the position of uterine manipulator (300) being fixed by the combination of balloon (324) and colpotomy cup (350), balloon (332) is inflated as shown in FIG. 25E. Balloon (332) bears outwardly against the sidewall of the vagina (V), thereby creating a fluid-tight seal against the sidewall of the vagina (V).

With uterine manipulator (300) being positioned and configured as shown in FIG. 25E, robotic arm (200) may be utilized to drive uterine manipulator (300) to various positions, to thereby re-orient and reposition the uterus (U) as desired by the clinician who is performing the rest of the medical procedure (e.g., hysterectomy). In some scenarios, the clinician who robotically controls robotic arm (200) to drive uterine manipulator (300) to position and orient the uterus (U) also uses the same robotic system to control instruments that are used to perform a surgical procedure associated with the uterus (U) (e.g., a hysterectomy). As noted above, by allowing a surgeon to directly control the manipulation of the uterus (U) via robotic arm (200) and uterine manipulator (300), the process avoids potential confusion and inconsistency that might otherwise result in procedures where a human assistant is controlling a uterine manipulator based on commands from another human clinician. Moreover, once the uterus (U) has been manipulated to achieve the desired position and orientation, robotic arm (200) and uterine manipulator (300) may cooperate to maintain this position and orientation of the uterus (U) indefinitely. This may avoid scenarios where a human operator of a uterine manipulator might inadvertently reposition or reorient the uterus (U) the middle of a medical procedure.

As noted above, one medical procedure that may be performed using robotic arm (200) and uterine manipulator (300) is a hysterectomy. In some versions of such a procedure, one or more cutting instruments are introduced laparoscopically via the patient's abdomen to approach the cervicovaginal junction from outside the uterus (U) and vagina (V). Such instrumentation may be controlled manually or robotically. In versions where the instrumentation is controlled robotically, the same robotic system may control the instrumentation and robotic arm (200). A cutting instrument may cut the uterus (U) away at the cervicovaginal junction, generally tracing around the circular perimeter defined by distal end (360) of colpotomy cup (350).

In some versions, the tissue at the cervicovaginal junction may be distended in response to pressure imposed by distal end (360) of colpotomy cup (350), thereby promoting visualization of the position of distal end (360) of colpotomy cup (350) from a laparoscope that is positioned external to the uterus (U) and vagina (V). Distal end (360) may also urge the ureters of the patient outwardly, thereby reducing the risk of the cutting instrument inadvertently cutting one of the ureters. Also in some versions, the cutting instrument may be received in space (366) defined between edges (362, 364) at distal end (360) of colpotomy cup (350) as the cutting instrument travels in a generally circular motion along the cervicovaginal junction. This cutting at the cervicovaginal junction will ultimately result in separation of the uterus (U) from the vagina (V); and the end of the vagina (V) may be appropriately closed at this point. During this process, the patient's abdomen may be insufflated with pressurized gas, and the pressurized insufflation gas may eventually reach the distal region of the vagina (V). In such scenarios, balloon (332) will provide sealed occlusion that is sufficient to prevent the pressurized insufflation gas from escaping out of the patient via the vagina (V).

While robotic arm (200) and uterine manipulator (300) are described in the foregoing example as being used in a hysterectomy, robotic arm (200) and uterine manipulator (300) may be used in any other suitable fashion and may be used in any other suitable procedures.

III. Exemplary Robotically Controlled Uterine Manipulator Having Robotic Actuation of Colpotomy Cup and Sleeve As mentioned above, sleeve (330) and colpotomy cup (350) may be advanced along shaft (320) such that distal end (360) cervix (C) is received within interior space (354) of colpotomy cup (350). In some instances, as also mentioned above, this movement of sleeve (330) and colpotomy cup (350) may be performed manually or may be performed by a robotic operator. In some instances, it may be desirable to move sleeve (330) and colpotomy cup (350) along shaft (320) via a robotic operator, as this functionality may allow for a greater degree of automation in positioning colpotomy cup (350) in accordance with the description herein. Additionally, such functionally may give an operator control to adjust the distance between colpotomy cup (350) and distal end (324) of shaft (320), thereby providing greater controlled manipulation of the uterine tissue while using uterine manipulator (300) in accordance with the description herein.

Figure 26:
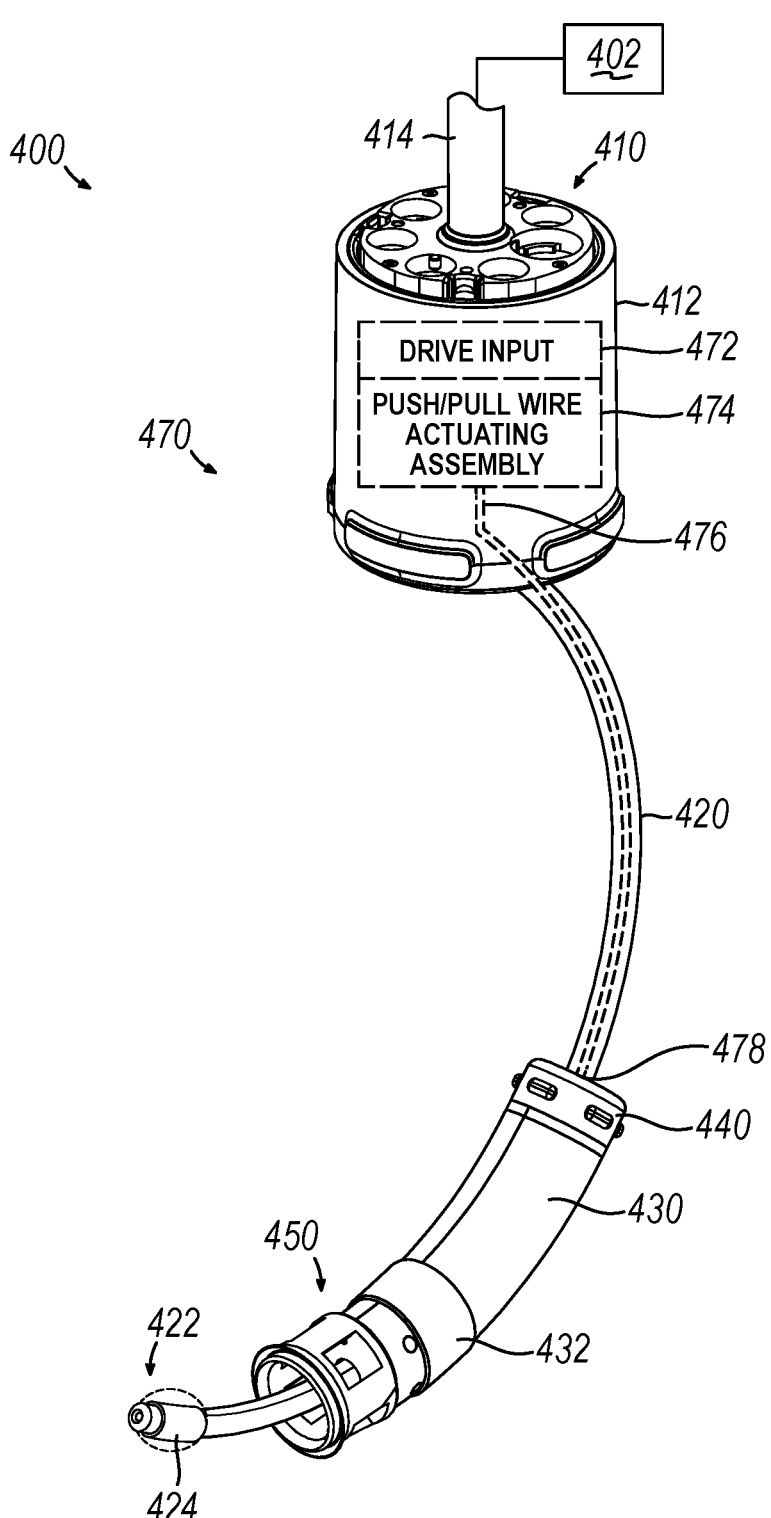
FIG. 26 depicts a perspective view of another exemplary uterine manipulator instrument.
Figure 27A:
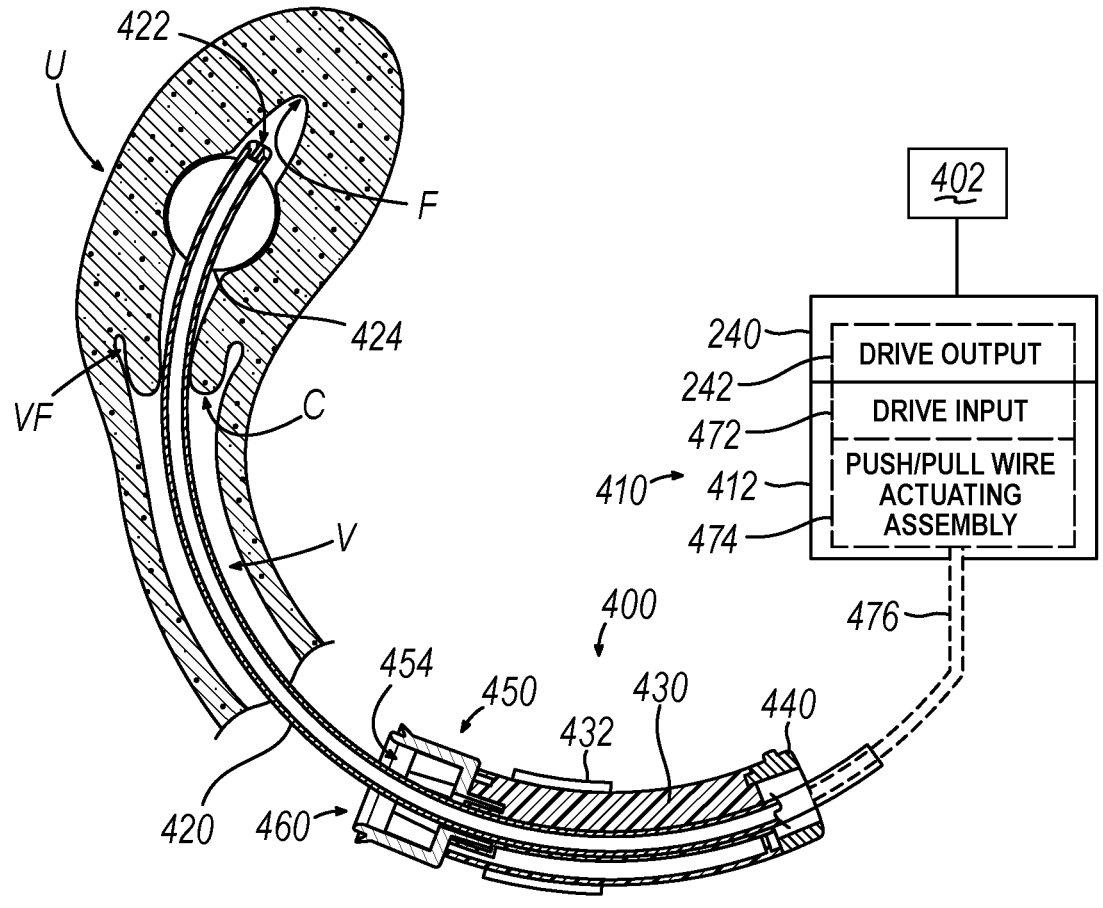
FIG. 27A depicts a mid-sagittal cross-sectional view of a vagina and uterus, with a shaft of the uterine manipulator instrument of FIG. 26 inserted through the vagina into the uterus, with a balloon of the uterine manipulator instrument of FIG. 21 in an inflated state, and with a sleeve of the uterine manipulator instrument in a proximal position.
Figure 27B:
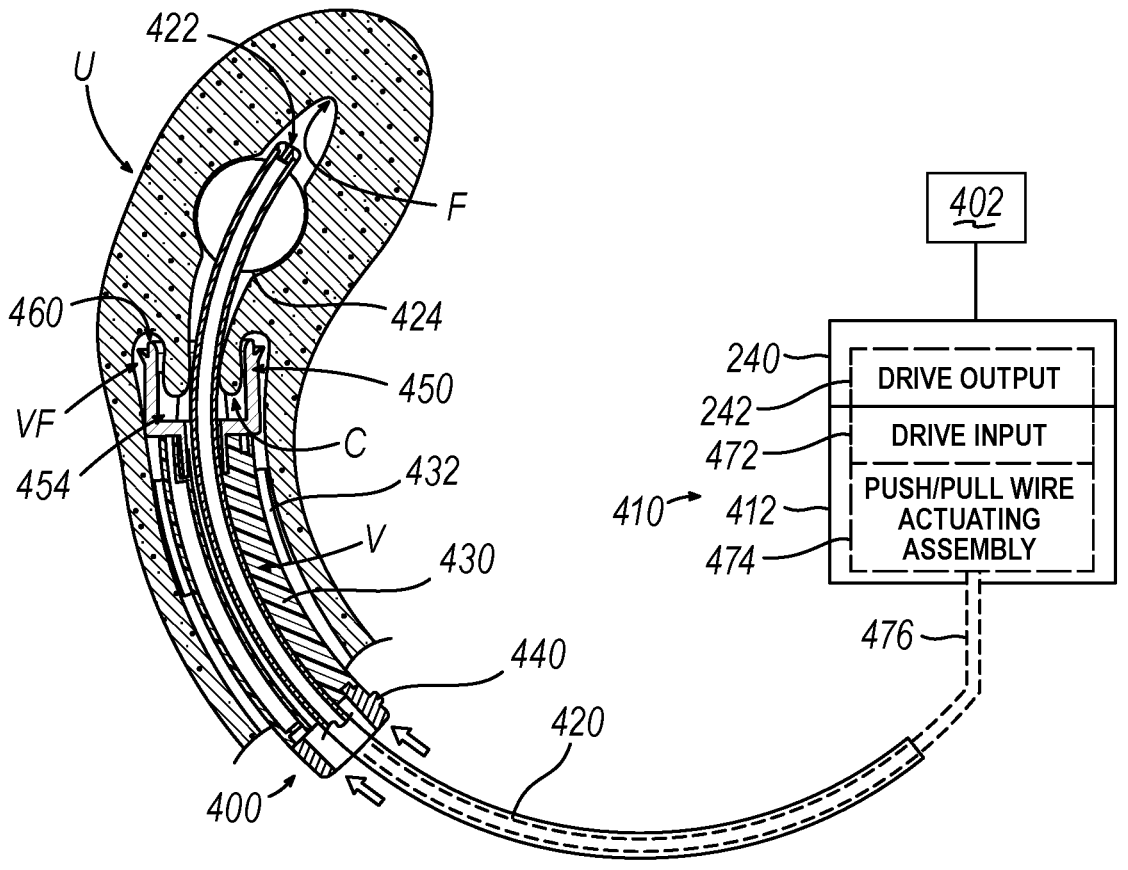
FIG. 27B depicts a mid-sagittal cross-sectional view of the vagina and uterus of FIG. 27A, with the shaft of the uterine manipulator instrument of FIG. 26 inserted through the vagina into the uterus, with the balloon of the uterine manipulator instrument of FIG. 21 in an inflated state, and with the sleeve of the uterine manipulator instrument in a distal position.
Figure 28:
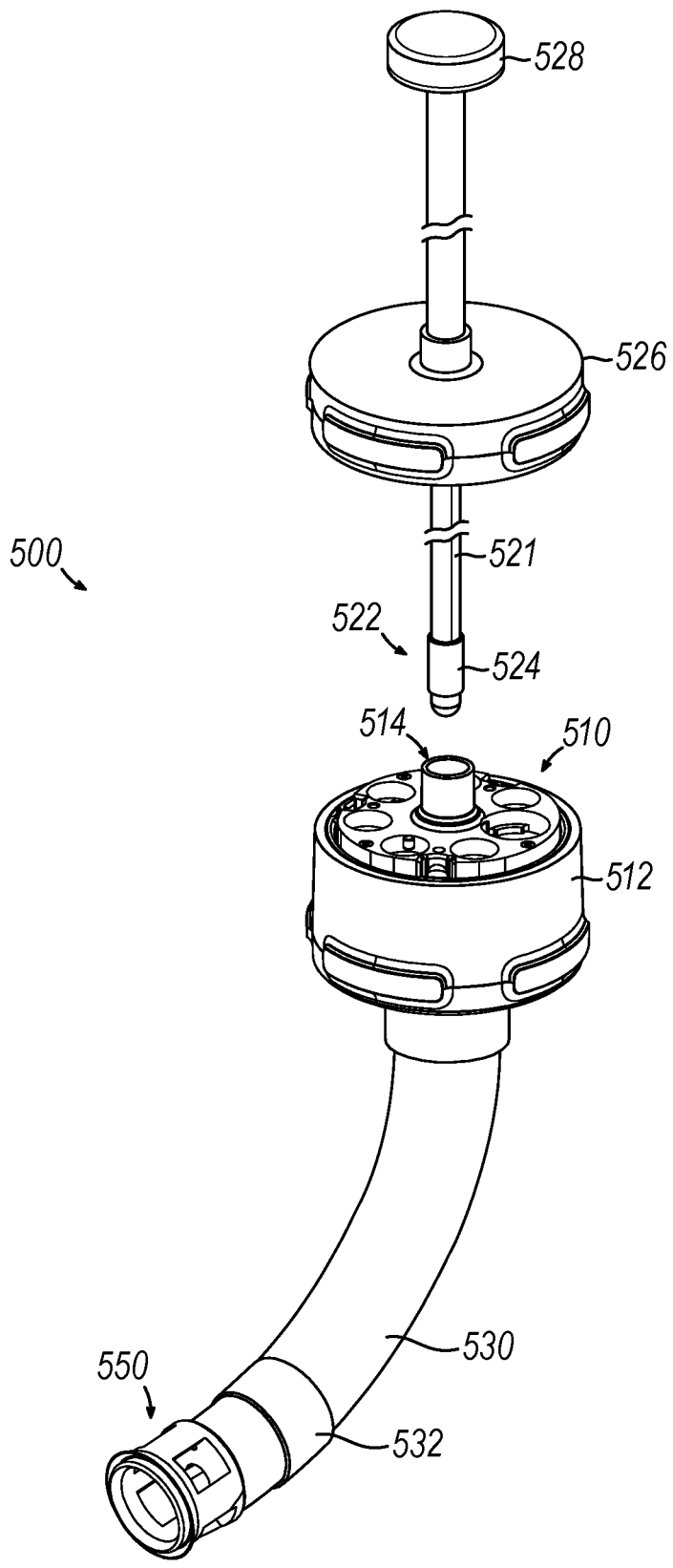
FIG. 28 depicts a perspective view of another exemplary uterine manipulator instrument.

FIGS. 26-27B show an exemplary uterine manipulator (400) having a colpotomy cup actuation assembly (470) configured to robotically actuate a sleeve (430) and colpotomy cup (450) along a shaft (420) in order to suitably control the position of colpotomy cup (450) relative to shaft (420) in accordance with the description herein. Uterine manipulator (400) may be substantially similar to uterine manipulator (300) described above, with differences elaborated below.

Uterine manipulator (400) includes a pressurized fluid source (402), a head interface assembly (410) having a base (412) and a shaft (414), a shaft (420) having a distal end (422) and a balloon (424), a sleeve (430) having a balloon (432), a sleeve locking ring (440), and a colpotomy cup (450) defining an interior space (454); which may be substantially similar to pressurized fluid source (302), head interface assembly (310), base (312), shaft (314), shaft (320), distal end (322), balloon (324), sleeve (330), balloon (332), sleeve locking ring (340), and colpotomy cup (350) defining interior space (354) described above, respectively, with differences elaborated herein.

As mentioned above, uterine manipulator (400) includes a colpotomy cup actuation assembly (470). Colpotomy cup actuation assembly (470) includes a drive input (472) associated with base (412) of head interface assembly (410), an actuating assembly (474) operatively coupled to drive input (472), and an elongated actuating member (476) operatively coupled to actuating assembly (474) and fixed to sleeve (430) at a distal end (478).

Drive input (472) may be substantially similar to drive input (89) of instrument base (87) or mechanical inputs (174) of instrument handle (170) describe above, with differences elaborated below. Drive input (472) may include any suitable components to operate in accordance with the description herein as would be apparent to one skilled in the art in view of the teachings herein. In some examples, drive input (472) includes receptacles, pulleys, and/or spools.

As best shown in FIGS. 27A-27B, when uterine manipulator (400) is operatively coupled to head (240) of robotic arm (200), drive input (472) is configured to operatively couple to a drive output (242) of head (240). Drive output (242) may be substantially similar to drive outputs (81) of instrument driver (80). Therefore, drive output (242) of head (240) of robotic arm (200) may be configured to transmit rotational motion generated by robotic motors (not shown) to drive input (472) of colpotomy cup actuation assembly (470).

Actuating assembly (474) is interposed between drive input (472) and elongated actuation member (476). Additionally, elongated actuation member (476) is slidably housed within shaft (420) such elongated auction member (476) may be advanced distally and retracted proximally along the length of shaft (420). As mentioned above, distal end (478) of elongated actuation member (476) is fixed to sleeve (430). Therefore, movement of actuation member (476) relative to shaft (470) drives movement of sleeve (430) and colpotomy cup (450) relative to shaft (470) via the coupling of distal end (478) and sleeve (430). Elongated actuation member (476) may include any suitable structures as would be apparent to one skilled in the art in view of the teachings herein. For example, elongated actuation member (476) may include a push-pull wire, a flexible band, etc.

Actuating assembly (474) is operatively coupled to both drive input (472) and elongated actuation member (476) such that actuation assembly (474) is configured to convert the rotational movement transmitted to drive input (472) into translational movement of elongated actuation member (476) within shaft (420). Actuation assembly (474) may include any suitable components as would be apparent to one skilled in the art in view of the teachings herein.

Drive input (472) may receive rotational motion from drive output (242) in a first rotational direction such that actuation assembly (474) may drive translation of elongated actuation member (476), sleeve (430), and colpotomy cup (450) in a distal direction relative to shaft (420). Conversely, drive input (472) may receive rotational motion from drive output (242) in a second, opposite, rotational direction such that actuation assembly (474) may drive translation of elongated actuation member (476), sleeve (430), and colpotomy cup (450) in a proximal direction relative to shaft (420). Therefore, an operator may utilize drive output (242) of robotic arm (200) in order to actuate colpotomy cup (450) along a length of shaft (420) to thereby selectively place colpotomy cup (450) at a desired location along shaft (420).

FIGS. 27A-27B show an exemplary use of colpotomy cup actuation assembly (470) to acuate colpotomy cup (450) to a desired location via robotic arm (200). As shown in FIG. 27A, distal end (422) of shaft (420) is suitably placed adjacent to fundus (F) while balloon (424) is inflated to stabilize distal portion of shaft (420). Next, rather than manually actuating sleeve (430) and colpotomy cup (450), an operator may actuate sleeve (430) and colpotomy cup (450) along shaft (420) via robotic arm (240) and colpotomy cup actuation assembly (470) in accordance with the description herein.

As shown in FIG. 27B, the operator may utilize colpotomy cup actuation assembly (470) to suitably place colpotomy cup (450) within the vagina (V) such that colpotomy cup (450) houses cervix (C) in accordance with the description herein. During the procedure, if the operator desires to change the distance between colpotomy cup (450) and balloon (424), the operator may adjust the placement of colpotomy cup (450) utilizing colpotomy cup actuation assembly (470) in accordance with the description herein.

In some scenarios where colpotomy cup actuation assembly (470) is not used to drive advance sleeve (330) and colpotomy cup (350) (e.g., when sleeve (330) and colpotomy cup (350) are advanced purely manually into the suitable position shown between FIGS. 25C-25D), an operator may use tactile feedback to determine if colpotomy cup (350) is suitably placed to house cervix (C) in accordance with the description herein. In scenarios where colpotomy cup actuation assembly (470) is used to drive advance sleeve (330) and colpotomy cup (350), uterine manipulator (400) may use one or more sensor(s) in order to determine that colpotomy cup (450) suitably houses cervix (C). For example, a force sensor, a position tracking sensor, a tissue detection sensor, and/or any other suitable sensor(s) that would be apparent to one skilled in the art in view of the teachings herein may be incorporated into uterine manipulator (400) in order to determine when colpotomy cup actuation assembly (470) has (A) actuated colpotomy cup (450) into a desired position, and/or (B) if colpotomy cup actuation assembly (470) is actuating colpotomy cup (450) into an undesired position.

A clinician may drive colpotomy cup actuation assembly (470) by manipulating user input features at a control station, such as console (31) or controller (182) described above. In some instances, the clinician may drive colotomy cup actuation assembly (470) with the control station such that the clinician may directly control the advancement and retraction of colpotomy cup (450). In other words, a clinician may utilize one or more user input features at a control station to start and stop actuation of colpotomy cup (450) as the clinician desires. In such instances, the clinician may rely on force and/or position sensing feedback to determine when colpotomy cup (450) has reached the appropriate position in accordance with the description herein; at which point, the clinician may stop advancement of colpotomy cup (450). Feedback may be provided by the clinician viewing a screen, listening to audible feedback (e.g., beeping, etc.), or feeling tactile feedback provided by controller (182).

In some other instances, a clinician may utilize colotomy cup actuation assembly (470) for automatically driving colpotomy cup (450) and sleeve (430) along shaft (420). For example, a clinician may just press a single input, such as a "go" button, and then robotic arm (200) may start driving colpotomy cup (450) and sleeve (430) along shaft (420), utilizing actuation assembly (470), until the force and/or positioning sensing feedback indicates that colpotomy cup (450) has reached the appropriate position in accordance with the description herein. Once the positioning sensing feedback indicates that colpotomy cup (450) has reached the appropriate position, colotomy cup actuation assembly (470) may automatically arrest further driving of colpotomy cup (450) and sleeve (430) along shaft (420) in response to such position sensing feedback.

IV. Exemplary Robotically Controlled Uterine Manipulator Having Modular Components In some instances, it may be desirable to have uterine manipulator (300) with modular components. Having modular components of uterine manipulator (300) may allow for dynamic insertion movement with the uterus (U) that a one-piece uterine manipulator (300) does not allow. Additionally or alternatively, one module component of a uterine manipular (300) may be designed to be reusable (i.e., may be suitably reprocessed and sterilized for another surgical procedure), while another modular component of a uterine manipulator (300) may be designed for a single use purposes. As another example, having modular components may allow for various combinations of modular components such that a single shaft (320) may be used to various sleeves (330) and colpotomy cups (350). Therefore, a single shaft (320) may be utilized with sleeves (330) and colpotomy cups (350) of various sizes such that an operator may use a single sized shaft (320) and choose a specific sized sleeve (330) and colpotomy cup (350) that is suitable for a specific patient. Additionally or alternatively, it may be desirable to configured uterine manipulator (300) such that multiple shafts (320) may be used, as different types of shafts (320) may be used for specific uterine (U) manipulation tasks.

FIGS. 29A-30B show a uterine manipulator (500) that is substantially similar to uterine manipulator (300) described above, with differences elaborated below. In particular, uterine manipulator (500) includes a modular colpotomy cup component (510) and a modular shaft component (520). As will be described in greater detail below, modular colpotomy cup component (510) is configured to couple to a distal end of head (240) of robotic arm (200); while modular shaft component (520) is configured to be inserted through a proximal end of head (240) of robotic arm (200), and through modular colpotomy cup component (510) such that a balloon (524) of modular shaft component (520) extends distally past colpotomy cup (550) of modular colpotomy cup component (510).

Modular colpotomy cup component (510) includes a proximal base (512) defining a proximal opening (514), a sleeve (530) fixed to proximal base (512), a balloon (532) coupled to sleeve (530), and a colpotomy cup (350) attached to a distal end of sleeve (530). Proximal base (512) defines a proximal opening (514) dimensioned to slidably receive a shaft (521) of modular shaft component (520) such that shaft (521) may extend through proximal base (512), sleeve (530), and colpotomy cup (550) when modular components (510, 520) are coupled together during exemplary use. Sleeve (530), balloon (532), and colpotomy cup (550) are substantially similar to sleeve (330), balloon (332), and colpotomy cup (350) described above, with differences elaborated below. Balloon (532) includes a fluidic coupling that may extend proximally from base (512) and couple with a pressurized fluid source, similar to pressurized fluid sources (302, 402) described above.

Figure 29A:
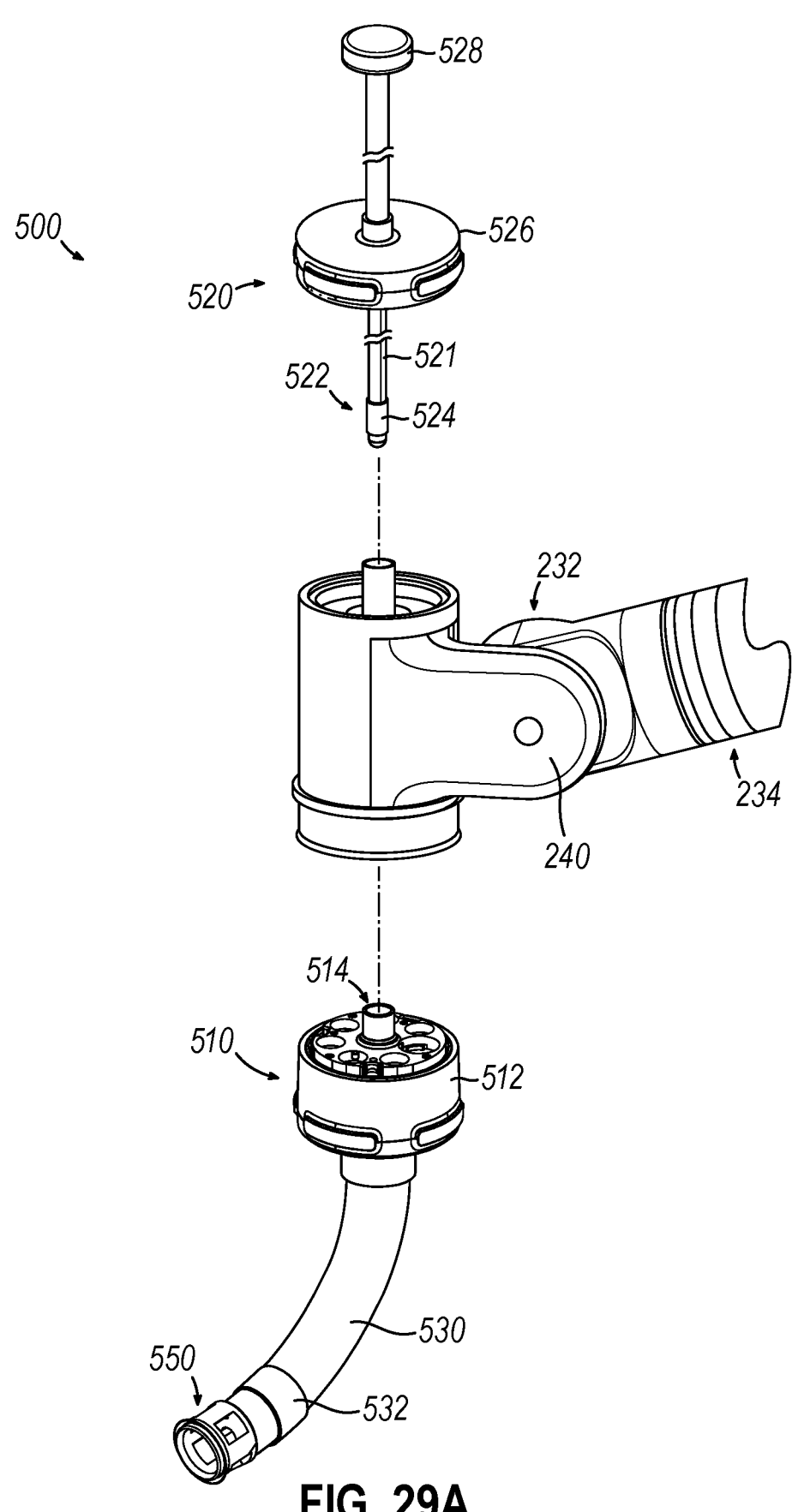
FIG. 29A depicts a perspective view of the uterine manipulator of FIG. 28 in a disassembled configuration with a robotic arm.
Figure 29B:
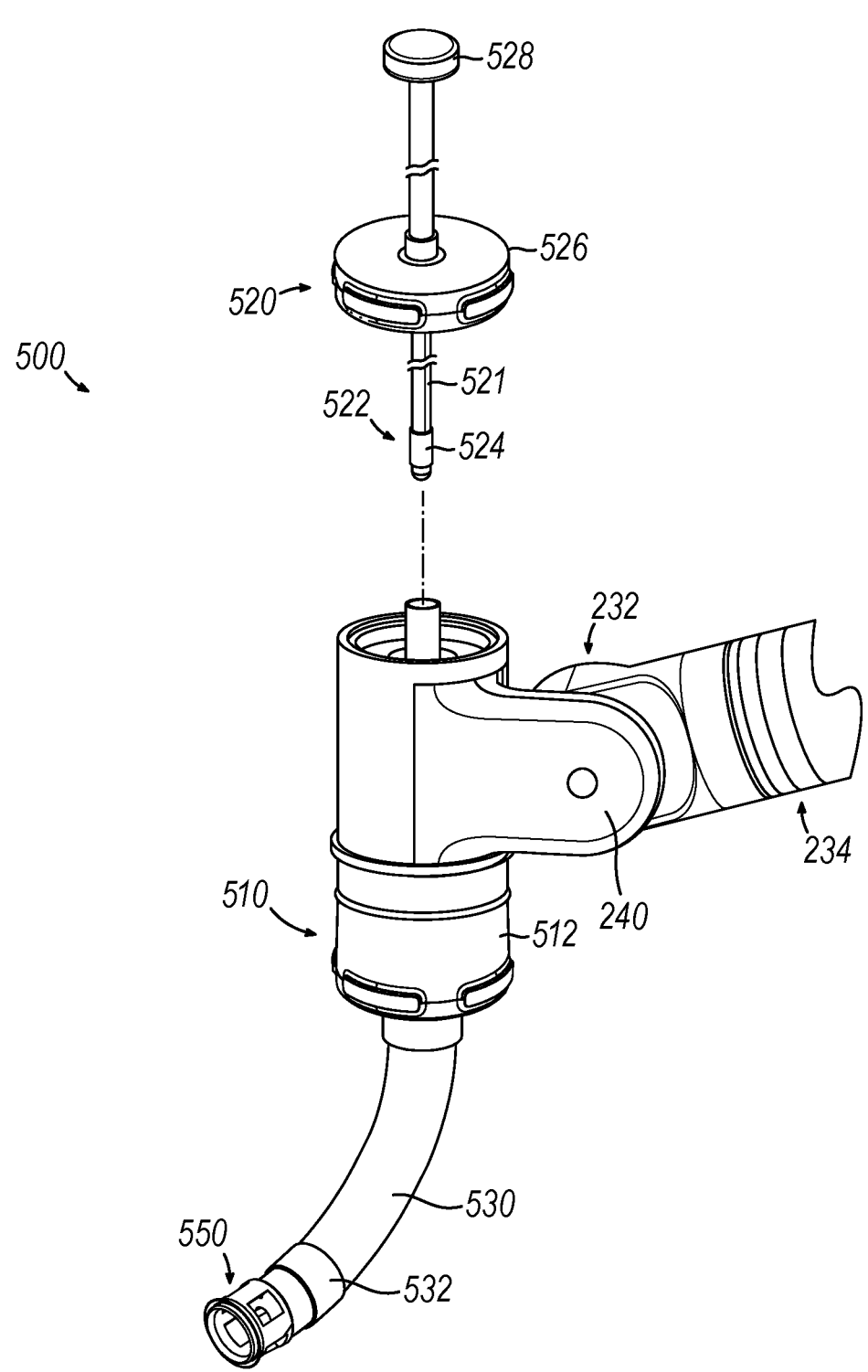
FIG. 29B depicts a perspective view of the uterine manipulator of FIG. 28, where a colpotomy cup component is coupled with the robotic arm of FIG. 29A while a shaft component is decoupled with the robotic arm.

As best shown between FIGS. 29A-29B, proximal base (512) is configured to attach to a distal end of head (240) of robotic arm (200) such that sleeve (530) and colpotomy cup (550) may be selectively fixed to head (240) of robotic arm (200). Therefore, movement of head (240) of robotic arm (200) may lead to corresponding movement of sleeve (530) and colpotomy cup (550) while proximal base (512) is attached to distal end of head (240). In some instances, a user may manually actuate head (240) of robotic arm (200) with modular colpotomy cup component (510) already attached in order to suitably place colpotomy cup (510) in accordance with the teachings herein. In other instances, robotic arm (200) may be used to actuate head (240) and modular colpotomy cup component (510) in order to suitably place colpotomy cup (510) in accordance with the teachings herein. In some instances, a combination of manual movement and robotic movement may be used to suitably place colpotomy cup (550) in accordance with the teachings herein.

Modular shaft component (520) includes shaft (521), balloon (524) located at a distal end (522) of shaft (521), a robotic arm interface (526) operatively coupled to shaft (521), and a proximal end (528) of shaft (521). Shaft (521) and balloon (524) may be substantially similar to shaft (320) and balloon (324) described above, with differences elaborated below. As shown between FIGS. 29B-29C, shaft (521) is suitably long enough such that as shaft (521) is inserted through the proximal end of head (240), through proximal opening (514) of base (512), and through sleeve (530) and colpotomy cup (550), a distal portion of shaft (521) that carries balloon (524) extends a suitable distance from colpotomy cup (550) in order for balloon (524) to serve as an anchor structure during exemplary use in accordance with the description herein.

Shaft (521) may be substantially laterally compliant such that as shaft (521) is inserted through sleeve (530) in accordance with the teachings herein, shaft (521) may bend or otherwise deform in order to promote distal advancement of shaft (521) through sleeve (530) and colpotomy cup (550). Shaft (521) may nevertheless have sufficient column strength to resist undesired buckling during insertion of shaft (521). While shaft (521) in the current example is shown extending along a linear longitudinal profile, it should be understood that this is merely optional. Shaft (521) may extend along a curved longitudinal profile substantially similar to that of sleeve (530). Alternatively, shaft (521) may extend along any other suitable longitudinal profile as would be apparent to one skilled in the art in view of the teachings herein.

Figure 29C:
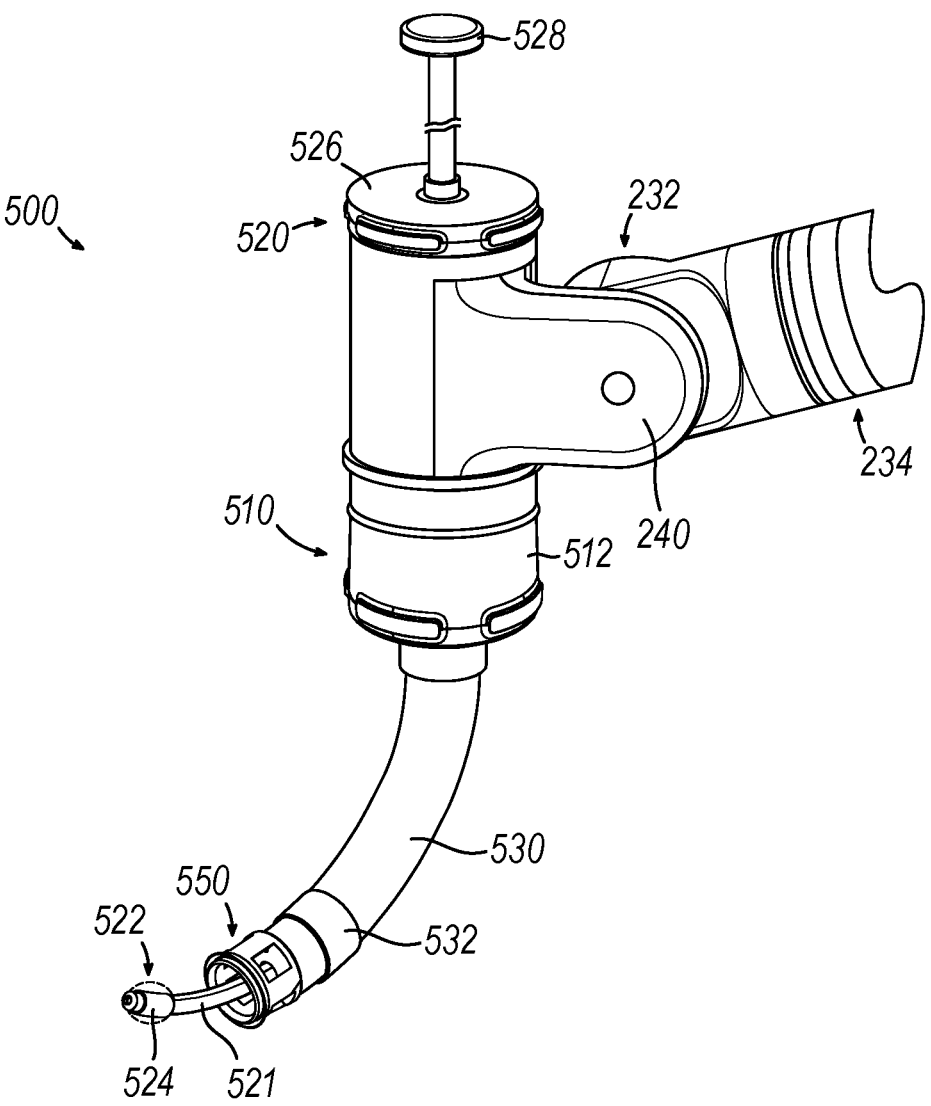
FIG. 29C depicts a perspective view of the uterine manipulator of FIG. 28, where the colpotomy cup component of FIG. 29B and the shaft component of FIG. 29B are both coupled with the robotic arm of FIG. 29A.

As also shown between FIGS. 29B-29C, robotic arm interface (526) is configured to suitably mate with a proximal end of head (240) of robotic arm (200) in order to couple modular shaft component (520) with head (240). When fully coupled, modular colpotomy cup component (510) and modular shaft component (520) are both coupled to head (240) of robotic arm (200). Therefore, head (240) of robotic arm (200) acts as an intermediary to couple modular interfaces (510, 520) together. Therefore, a user may acuate head (240), either manually or robotically as described above, in order to suitably place colpotomy shaft (521) and colpotomy cup (550) in accordance with the teachings herein.

Robotic arm interface (526) is configured to mate with suitable components of head (240) of robotic arm (200), such as drive output (242), such that head (240) may acuate shaft (521) proximally and distally relative to robotic arm interface (526), sleeve (530), and colpotomy cup (550) when both modular components (510, 520) are suitably coupled to head (240).

Figure 30A:
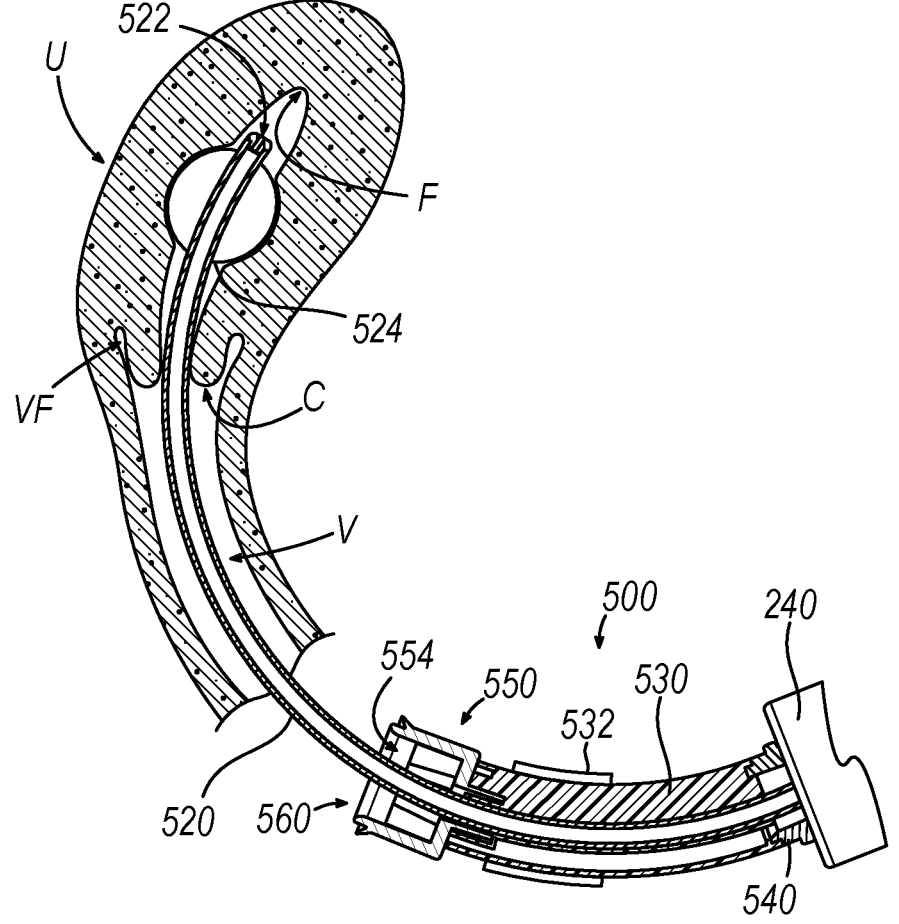
FIG. 30A depicts a mid-sagittal cross-sectional view of a vagina and uterus, with a shaft of the uterine manipulator instrument of FIG. 28 inserted through the vagina into the uterus, with a balloon of the uterine manipulator instrument of FIG. 28 in an inflated state, and with a sleeve of the uterine manipulator instrument in a proximal position.
Figure 30B:
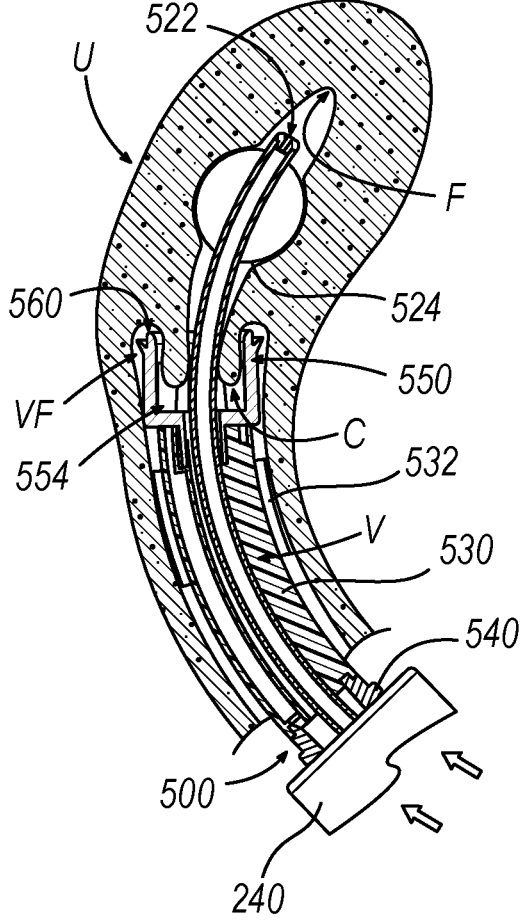
FIG. 30B depicts a mid-sagittal cross-sectional view of the vagina and uterus of FIG. 30A, with the shaft of the uterine manipulator instrument of FIG. 28 inserted through the vagina into the uterus, with the balloon of the uterine manipulator instrument of FIG. 28 in an inflated state, and with the sleeve of the uterine manipulator instrument in a distal position.

FIGS. 30A-30B shows an exemplary use of uterine manipulator (500) and head (240) of robotic arm (200) in order to suitably place colpotomy cup (550) to house cervix (C) after balloon (324) is already deployed to act as a distal anchoring mechanism. As shown in FIG. 30A, a distal end (522) of shaft (521) is suitable placed adjacent to fundus (F) while balloon (524) is inflated to stabilize distal portion of shaft (521). Next, as shown in FIG. 30B, robotic head (240) may actuated, either manually or robotically, in order to advance sleeve (530) and colpotomy cup (350) such that colpotomy cup (550) suitably engages cervix (C) in accordance with the teachings herein. As head (240) is actuated along with sleeve (530) and colpotomy cup (550) to advance sleeve (530) and colpotomy cup (550) into the vagina (V), head (240) of robotic arm (200) may suitably drive robotic arm interface (526) in order to acuate shaft (521) proximally relative to robotic arm interface (526), head (240), sleeve (530), and colpotomy cup (550), such that balloon (524) remains relatively stationary within the uterus (U) while inflated. In other words, while head (240) is moved in order to drive colpotomy cup (550) into place, head (240) may also drive robotic arm interface (526) in order to move shaft (521) relative to colpotomy cup (350), thereby keeping balloon (524) stationary within the uterus (U).

Since colpotomy cup (550) and sleeve (530) are configured to selectively couple with shaft (521) via modular components (510, 520), a multitude of modular colpotomy cup components (510) having various sized colpotomy cups (550) and sleeves (530) may be configured to couple with a multitude of shafts (521) having various sizes and longitudinal profiles. Therefore, an operator may mix and match different modular colpotomy cup components (510) with different modular shaft components (520) in order to accommodate for the anatomical dimensions of the specific patient at hand, in order to perform specific uterine manipulation maneuvers, or based on any other suitable need as would be apparent to one skilled in the art in view of the teachings herein. Additionally, as mentioned above, one modular components (510, 520) may be configured to be disposable, while the other modular component (510, 520) may be configured to be reusable.

V. Exemplary Colpotomy Cup with Tissue Sensing
Capabilities

As mentioned above, colpotomy cup (350) serves as a proximally-positioned anchor structure for uterine manipulator (300). Therefore, during exemplary use of uterine manipulator (300), it may be desirable to keep the cervix (C) engaged with floor (358) of body (352) of colpotomy cup (350). However, in some instances for various reasons as will be apparent to those skilled in the art in view of the teachings herein, the portion of cervix (C) that is intended to engage with floor (358) may migrate such that the cervix (C) is no longer seated on floor (358); which may lead to less accurate uterine manipulation by manipulator (300). Therefore, it may be desirable to have a colpotomy cup (350) that is configured to detect if and when the cervix (C) has undesirably migrated away from floor (358).

Figure 31:
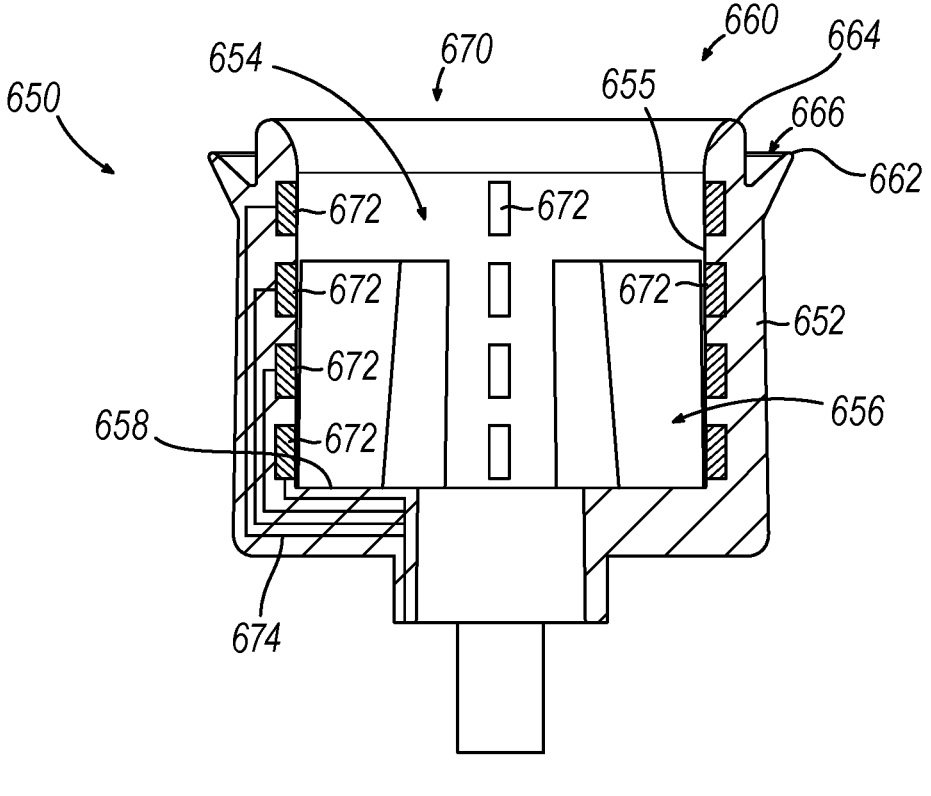
FIG. 31 depicts a side cross-sectional view of an exemplary colpotomy cup, taken along a center line thereof.
Figure 32A:
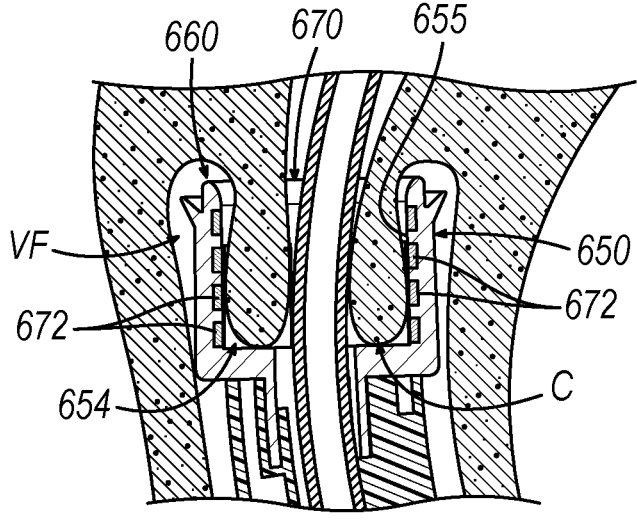
FIG. 32A depicts a mid-sagittal cross-sectional view of a vagina and uterus, with the colpotomy cup of FIG. 31 in a first position relative to a cervix.
Figure 32B:
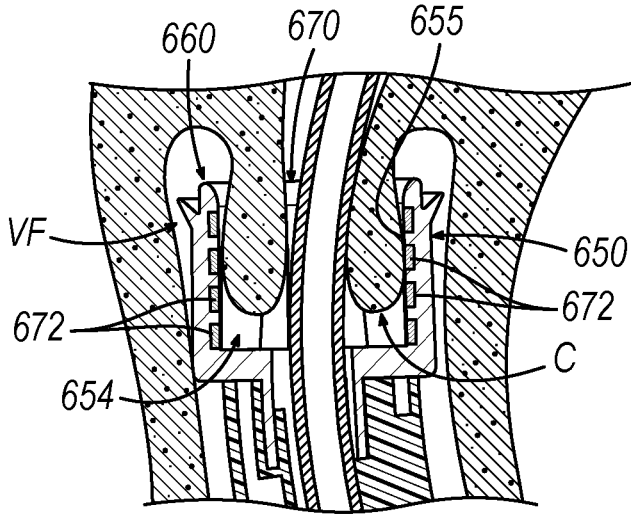
FIG. 32B depicts a mid-sagittal cross-sectional view of the vagina and uterus of FIG. 32A, with the colpotomy cup of FIG. 31 in a second position relative to the cervix.

FIGS. 31-32B show an exemplary colpotomy cup (650) that may be readily incorporated into uterine manipulator (300, 400, 500) in replacement of colpotomy cup (350, 450, 550). Colpotomy cup (650) is substantially similar to colpotomy cup (350, 450, 550) described above, with differences elaborated below. In particular, colpotomy cup (650) includes a tissue sensing assembly (670) configured to detect whether or not the cervix (C) is properly seated within an interior space (654) of colpotomy cup (650) during exemplary use in accordance with the description herein.

Colpotomy cup (650) includes a body (652) having a floor (658), an obliquely presented annular edge (662), and an annular edge (664); which may be substantially similar to body (352), floor (358), obliquely presented annular edge (362), and annular edge (364) described above, respectively, with differences elaborated below. Body (652) defines an interior space (654), lateral openings (656), and open distal end (660); which may be substantially similar to interior space (354), lateral openings (356), and open distal end (360) described above, respectively, with differences elaborated below. Annular edges (662, 664) define a space (666) which may be substantially similar to space (366) described above, with differences elaborated below.

Tissue sensing assembly (670) includes at least one linear array of tissue sensing elements (672) extending along a length of an annular interior surface (655) of colpotomy cup (650). Tissue sensing elements (672) are configured to detect whether or not tissue sensing element (672) is in direct contact with tissue, such as the cervix (C). Tissue sensing elements (672) may include any suitable sensor as would be apparent to one skilled in the art in view of the teachings herein. For instance, tissue sensing elements (672) may include electrodes that are configured to serve as impedance sensors.

Since the most proximal tissue sensing element (672) is located adjacent to floor (658), if that tissue sensing element (672) detects tissue, tissue sensing assembly (670) may determine the cervix (C) is seated against floor (658). If the most proximal tissue sensing element (672) no longer detects tissue, tissue sensing assembly (670) may determine the cervix (C) has undesirably migrated from floor (658).

Tissue sensing elements (672) are in communication with a processor of a suitable computer system via electrical traces (674) extending proximally from tissue sensing elements (672), through body (652), and proximally back to any suitable structures configured to establish communication with the suitable computer system. Since tissue sensing elements (672) may detect whether or not each respective element (672) is in contact with tissue and communicate such information to a suitable computer system, tissue sensing elements (672) may be used in combination with a suitable algorithm to determine if cervix (C) has moved within the interior of colpotomy cup (650) during exemplary use in accordance with the description herein.

Figure 33:
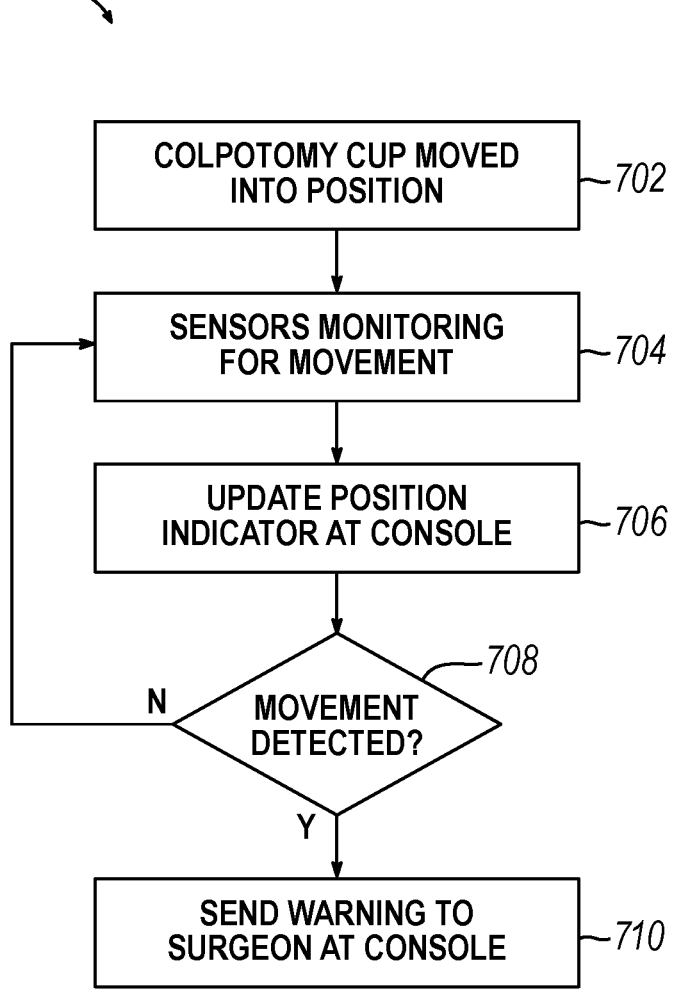
FIG. 33 shows an exemplary block diagram of an algorithm that may be used in conjunction with the colpotomy cup of FIG. 31.

One exemplary algorithm (700) is shown in FIG. 33. First as shown in block (702), colpotomy cup (650) may be moved into position such that cervix (C) is suitably housed within interior space (654). As shown in FIG. 32A, cervix (C) may be suitably housed within interior space (654) when cervix (C) is seated against floor (658). Next, tissue sensing assembly (670) may monitor for movement of cervix (C) within colpotomy cup (650), as indicated in block (704) and then update the position of cervix (C) to the processor of the suitable computer system as shown in block (706). If movement is not detected, the algorithm may repeat the processes in blocks (704, 706) until a point in the operation is reached when it is no longer desirable to have cervix (C) housed within colpotomy cup (650). However, as shown in block (710), if movement of the cervix (C) is detected, as shown between FIGS. 32A-32B, tissue sensing assembly (670) may send a warning to the surgeon at a suitable computer system, such as a console (31), thereby indicating that the cervix (C) is no longer properly seated within colpotomy cup (650), as is shown in FIG. 32B. Therefore, the surgeon may make the necessary adjustments to properly house cervix (C) within colpotomy cup (650).

VI. Exemplary Colpotomy Cup with Lighting
Features

As mentioned above, in some instances distal end (322) of shaft (320) may include an illuminating element that may provide transillumination through the wall of the uterus (U). Such transillumination may be observed via a laparoscope or other visualization device that is positioned external to the uterus (U). Such transillumination may indicate the extent to which shaft (320) has been inserted into the uterus (U). In some instances, it may be desirable for colpotomy cup (350) to include an illumination feature. Such an illumination feature on colpotomy cup (350) may be controlled by an operator at a surgeon's console (31). Such an illumination feature may provide a contrast to help guide the surgeon when manipulating a uterus (U) with uterine manipulator (300) or to help guide the surgeon when performing a colpotomy. Additionally, it may be desirable to adjust the color and brightness provided on such an illumination feature for better contrast and/or exposure.

Figure 34:
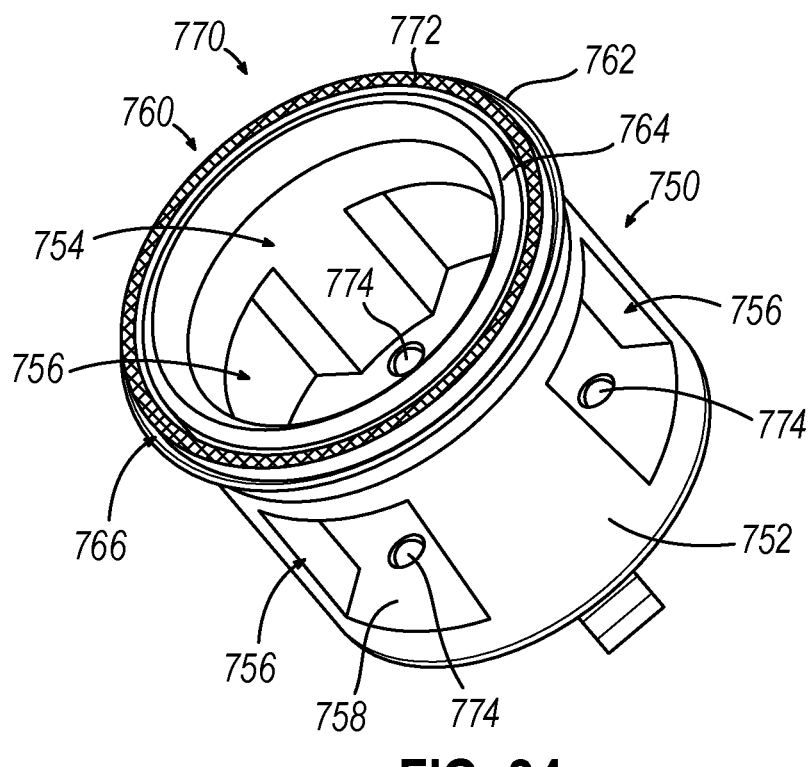
FIG. 34 depicts a perspective view of another exemplary colpotomy cup.

FIG. 34 shows an exemplary colpotomy cup (750) that may be readily incorporated into uterine manipulator (300, 400, 500) in replacement of colpotomy cup (350, 450, 550). Colpotomy cup (750) is substantially similar to colpotomy cup (350, 450, 550, 650) described above, with differences elaborated below. In particular, colpotomy cup (750) includes an illumination assembly (770) configured to provide the above mentioned functionality.

Colpotomy cup (750) includes a body (752) having a floor (758), an obliquely presented annular edge (762), and an annular edge (764); which may be substantially similar to body (352), floor (358), obliquely presented annular edge (362), and annular edge (364) described above, respectively, with differences elaborated below. Body (752) defines an interior space (754), lateral openings (756), and open distal end (760); which may be substantially similar to interior space (354), lateral openings (356), and open distal end (360) described above, respectively, with differences elaborated below. Annular edges (762, 764) define a space (766) which may be substantially similar to space (366) described above, with differences elaborated below.

Illumination assembly (770) in the current example includes a first light source (772) extending annularly within space (766) defined by annular edges (762, 764) and a second light source (774) located on floor (758) of colpotomy cup (750). First light source (772) and/or second light source (774) may use one ore more light pipes, one or more LEDs, or any other suitable illumination features as would be apparent to one skilled in the art in view of the teachings herein. Therefore, first light source (772) and second light source (774) are configured to emit light. A surgeon may control whether either light source (772, 774) is activated, the color either light source (772, 774) emits while activated, and/or the brightness at which either light source (772, 774) emits lights at a surgeon's console (31).

The surgeon may use light sources (772, 774) in order to visualize the location of colpotomy cup (750) during exemplary use via transillumination from visuals provided via a laparoscope or other visualization device that is positioned external to the uterus (U). Therefore, the surgeon may be assisted in manipulating the uterus (U) or performing a colpotomy by viewing the transillumination features provided by light sources (772, 774) during exemplary use in accordance with the description herein. Moreover, light sources (772, 774) may be used to illuminate a field of view for one or more cameras located on a suitable uterine manipulator (300, 400, 500, 800); in addition to, or as an alternative to, providing the transillumination effect through tissue. While in the current example, illumination assembly (770) includes both light sources (772, 774), this is merely optional. Some variations may include only first light source (772), while other variations only include second light sources (774).

VII. Exemplary Robotically Controlled Uterine Manipulator Having Robotically Controlled Tissue Grasping In some instances, as mentioned above, the cervix (C) may migrate while housed within colpotomy cup (350). Therefore, in some instances, it may be desirable to provide a tissue grasping feature on colpotomy cup (350) that may help prevent the cervix (C) from moving relative to colpotomy cup (350).

Figure 35:
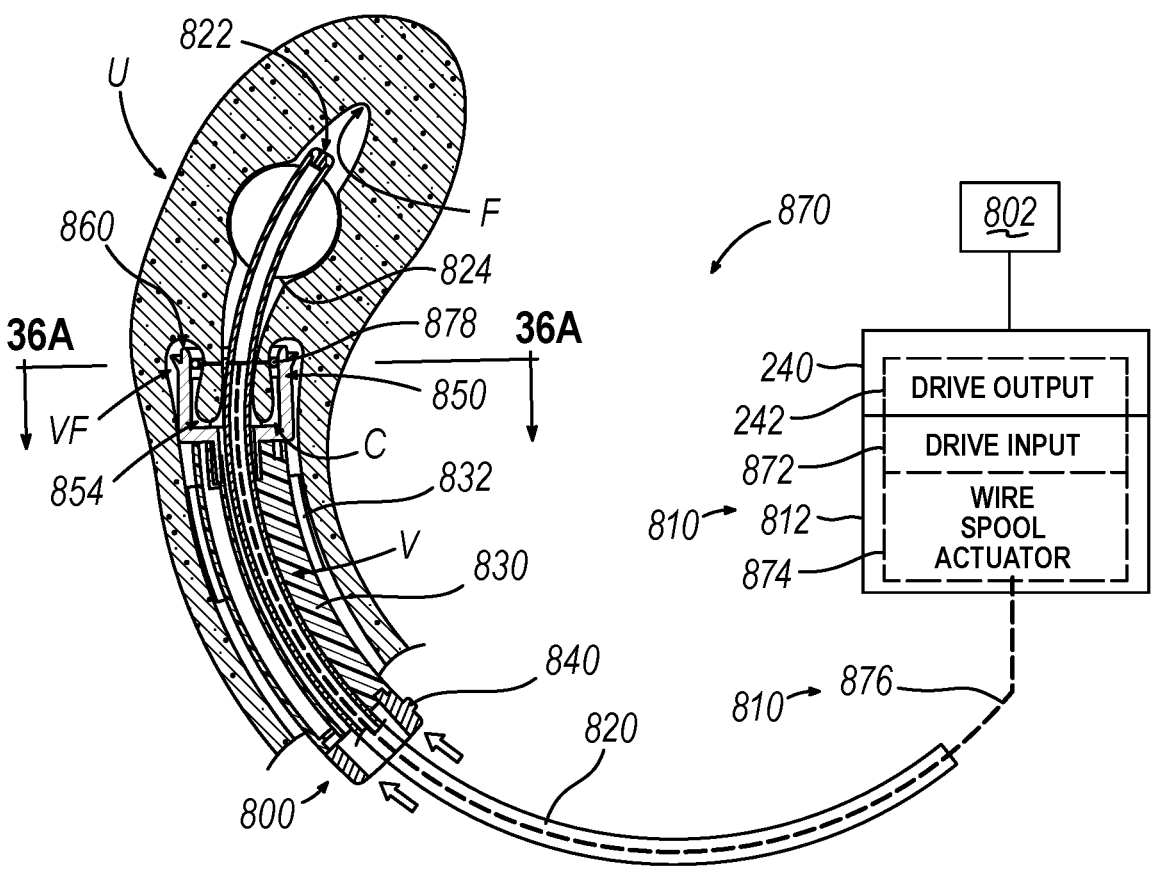
FIG. 35 depicts a mid-sagittal cross-sectional view of a vagina and uterus, with a shaft of a uterine manipulator instrument inserted through the vagina into the uterus, with a balloon of the uterine manipulator instrument in an inflated state, and with a sleeve of the uterine manipulator instrument in a distal position.
Figure 36A:
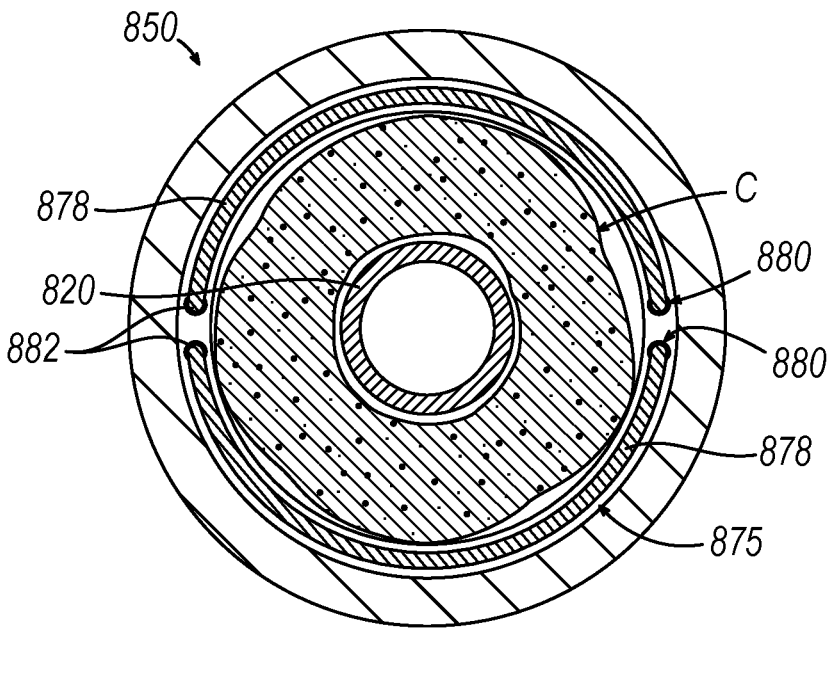
FIG. 36A depicts a top plan view of a colpotomy cup of the uterine manipulator instrument of FIG. 35, with a cervix retention feature in a non-gripping configuration.
Figure 36B:
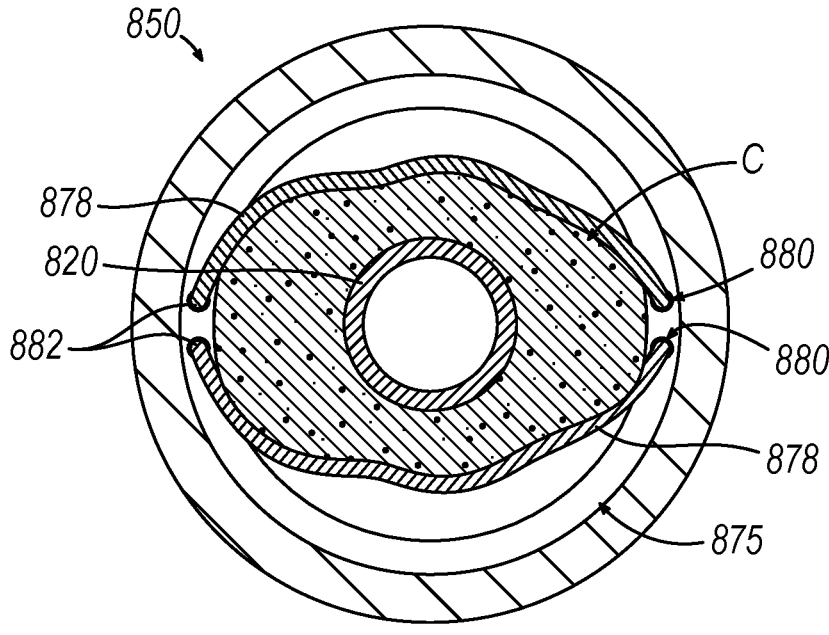
FIG. 36B depicts a top plan view of a colpotomy cup of the uterine manipulator instrument of FIG. 35, with the cervix retention feature in a gripping configuration.

FIGS. 35-36B show an exemplary uterine manipulator (800) having a tissue grasping assembly (870) configured to robotically actuate a pull wire (876) in order to suitably control the position of the cervix (C) housed within a colpotomy cup (850) in accordance with the description herein. Uterine manipulator (800) may be substantially similar to uterine manipulator (300) described above, with differences elaborated below. Uterine manipulator (800) includes a pressurized fluid source (802), a head interface assembly (810) having a base (812), a shaft (820) having a distal end (822) and a balloon (824), a sleeve (830) having a balloon (832), a sleeve locking ring (840), and a colpotomy cup (850) defining an interior space (854); which may be substantially similar to pressurized fluid source (302), head interface assembly (310), base (312), shaft (320), distal end (322), balloon (324), sleeve (330), balloon (332), sleeve locking ring (340), and colpotomy cup (350) defining interior space (354) described above, respectively, with differences elaborated herein.

As mentioned above, uterine manipulator (800) includes a tissue grasping assembly (870). Tissue grasping assembly (870) includes a drive input (872) associated with base (812) of head interface assembly (810), a wire spool actuator (874) operatively coupled to drive input (872), and at least one pull wire (876) operatively coupled to actuating assembly (874) with a pair of resilient arched wire segments (878) housed within an annular recess (875) defined by an interior surface of colpotomy cup (850).

Drive input (872) may be substantially similar to drive input (89) of instrument base (87) or mechanical inputs (174) of instrument handle (170) describe above, with differences elaborated below. Drive input (872) may include any suitable components to operate in accordance with the description herein as would be apparent to one skilled in the art in view of the teachings herein. In some examples, drive input (872) includes receptacles, pulleys, and/or spools.

As best shown in FIGS. 35, when uterine manipulator (800) is operatively coupled to head (240) of robotic arm (200), drive input (872) is configured to operatively couple to a drive output (242) of head (240). Therefore, drive output (242) of head (240) of robotic arm (200) may be configured to transmit rotational motion generated by robotic motors (not shown) to drive input (872) of tissue grasping assembly (870).

Actuating assembly (874) is interposed between drive input (872) and at least one pull wire (876) such that movement of actuating assembly (874) drives movement of pull wire (876). Actuating assembly (874) may include a wire spool actuator. Additionally, pull wire (876) is slidably housed within shaft (820) such pull wire (870) may acuate within shaft (820) to selectively expand and retract resilient arched wire segments (878) in accordance with the description herein. Therefore, actuating assembly (874) is configured to drive movement of pull wire (876) in order to selectively expand and retract arched wire segments (878).

As best shown in FIG. 36A, each arched wire segments (878) is housed within an annular recess (875) defined by colpotomy cup (850). One end of each arched wire segment (878) is fixed to colpotomy cup (850) at a terminating end (882), while another end of each arched wire segment (878) extends through a feed hole (880) defined by colpotomy cup (850). The portion of arched wire segment (878) extending through feed hole (880) is fixed to pull wire (876) such that actuation of pull wire (876) may drive wire segments (878) between the expanded and retracted configuration. Arched wire segments (878) are sufficiently flexible to bend from the expanded position shown in FIG. 36A to the retracted position shown in FIG. 36B in response to proximal actuation of pull wire (876). In particular, as pull wire (876) is actuated proximally, portions of arched wire segments (878) actuate proximally into feed hole (880). Since terminating ends (882) are fixed to colpotomy cup (850), arched wire segments (878) transition into the retracted configuration shown in FIG. 36B in response to proximal retraction of pull wire (876). However, arched segments (878) are sufficiently resilient such that when pull wire (876) is actuated distally or released, the resilient nature of arched segments (878) allows segments (878) to return to the expanded configuration as shown in FIG. 36A.

Once colpotomy cup (850) is suitably positioned to house cervix (C) in accordance with the description herein, an operator may instruct drive output (242) to acuate drive input (872) and actuating assembly (874) in order to drive pull wire (876) to retract resilient arched wire segments (878) as shown between FIGS. 36A-36B. Therefore, a surgeon may control the configuration of arched wire segments (878) from a surgeon's console (31). While in the retracted configuration as shown in FIG. 36B, resilient arched wire segments (878) (878) may help maintain the position of cervix (C) while housed within colpotomy cup (850).

In some instances, the tension provided by arched wire segments (878) grasping cervix (C) in the contracted configuration may be monitored from the surgeon's console (31). If the monitored tension has dropped, a signal can alert the surgeon, indicating that the arched wire segments (878) no longer sufficiently grasp cervix (C), which may indicate that the cervix (C) has moved out of position relative to colpotomy cup (850).

In some instances, arched wire segments (878) may be energized such that arched wire segments (878) may be configured to create the colpotomy while energized and in the contracted configuration.

VIII. Exemplary Colpotomy Cup with Suction Features

Figure 37:
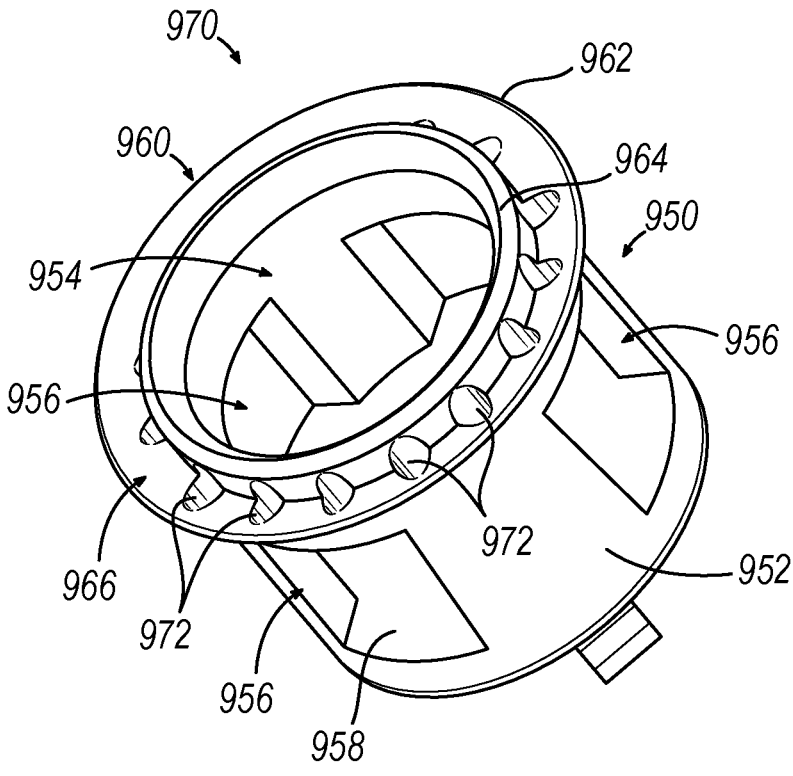
FIG. 37 depicts a perspective view of another exemplary colpotomy cup.
Figure 38A:
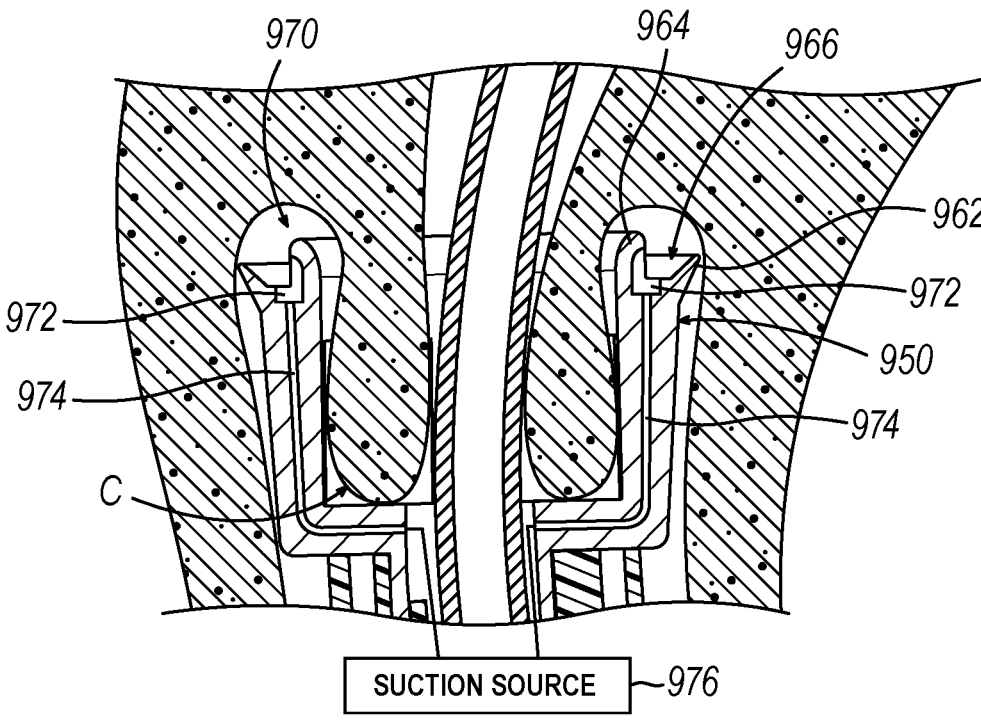
FIG. 38A depicts a mid-sagittal cross-sectional view of a cervix, with the colpotomy cup of FIG. 37 in a distal position, with a suction assembly of the colpotomy cup deactivated.

In some instances, as mentioned above, the cervix (C) may migrate while housed within colpotomy cup (350). Therefore, in some instances, it may be desirable to provide a tissue grasping feature on colpotomy cup (350) that may help prevent the cervix (C) from moving relative to colpotomy cup (350). FIGS. 37-38A shows an exemplary colpotomy cup (950) that may be readily incorporated into uterine manipulator (300, 400, 500, 800) in replacement of colpotomy cup (350, 450, 550, 850). Colpotomy cup (950) is substantially similar to colpotomy cup (350, 450, 550, 650, 850) described above, with differences elaborated below. In particular, colpotomy cup (950) includes suction assembly (970) configured to provide suction to grasp tissue in order to inhibit movement of the cervix (C) while housed within colpotomy cup (950).

Colpotomy cup (950) includes a body (952) having a floor (958), an obliquely presented annular edge (962), and an annular edge (964); which may be substantially similar to body (352), floor (358), obliquely presented annular edge (362), and annular edge (364) described above, respectively, with differences elaborated below. Body (952) defines an interior space (954), lateral openings (956), and open distal end (960); which may be substantially similar to interior space (354), lateral openings (356), and open distal end (360) described above, respectively, with differences elaborated below. Annular edges (962, 964) define a space (766) which may be substantially similar to space (366) described above, with differences elaborated below.

Figure 38B:
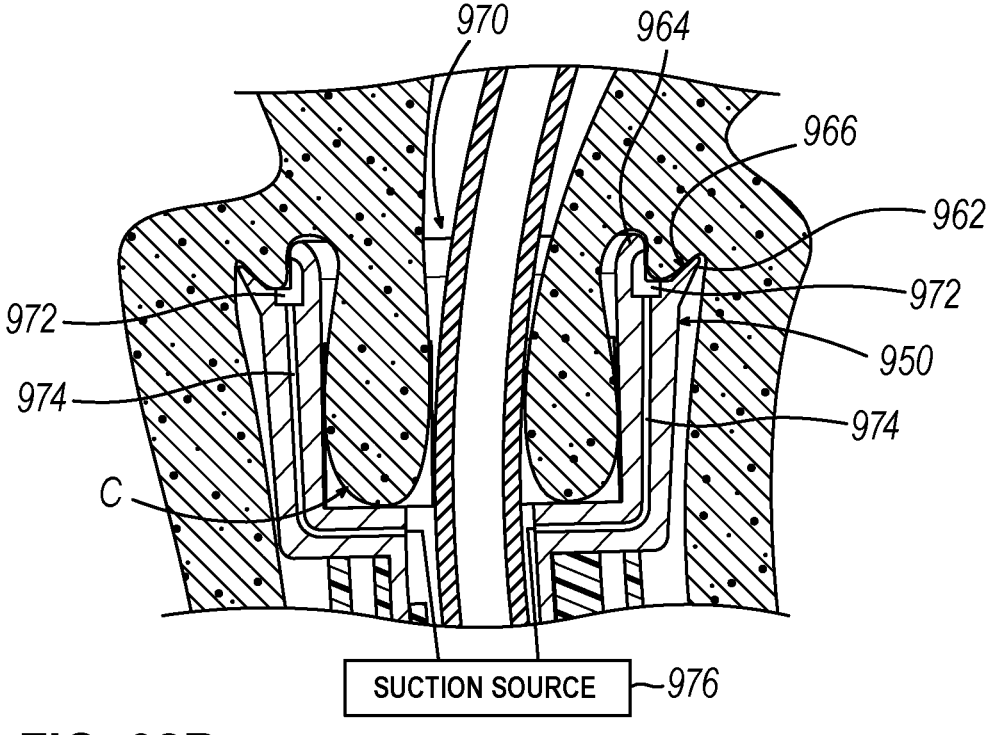
FIG. 38B depicts a mid-sagittal cross-sectional view of the cervix of FIG. 38A, with the colpotomy cup of FIG. 37 in a distal position, with the suction assembly of FIG. 38A activated.

Suction assembly (970) includes an annular array of suction ports (972) placed along a portion of annular edges (962, 964) defining space (966). As best shown in FIGS. 38A-38B, each suction port (972) is in fluid communication with a respective fluid line (974) defined by body (952). Fluid lines (974) provide fluid communication between suction ports (972) and a suitable suction source (976). Suction source (976) may be located at any suitable location, including within uterine manipulator (300, 400, 500, 800), within robotic arm (200), or as a self-standing suction machine located near, yet separated from, robotic arm (200). Suction source (976) may be configured to be activated by an operator at a surgeon's console (31) or local to the surgical operation site at which colpotomy cup (950) is located.

As best shown between FIGS. 38A-38B, once colpotomy cup (950) is suitably placed in order to house cervix (C), the operator may activate suction source (976). Activation of suction source (976) may allow suction to be communicated to suction ports (972) via fluid lines (974). Suction created at suction ports (972) causes draws tissue adjacent to suction ports (972) toward space (966) and into engagement with distal end (960), such that the suction provides grasping of the tissue by colpotomy cup (950). Since ports (972) are located adjacent to space (966), the tissue grasped may be forced to at least partially conform to the geometry defining space (966), which may help for purposes of manipulating the uterus (U) and/or performing a colpotomy. Therefore, suction assembly (970) may assist an operator suitably manipulate uterus (U) in accordance with the teachings herein and/or assist an operator in performing a colpotomy in accordance with the teachings herein.

Figure 39A:
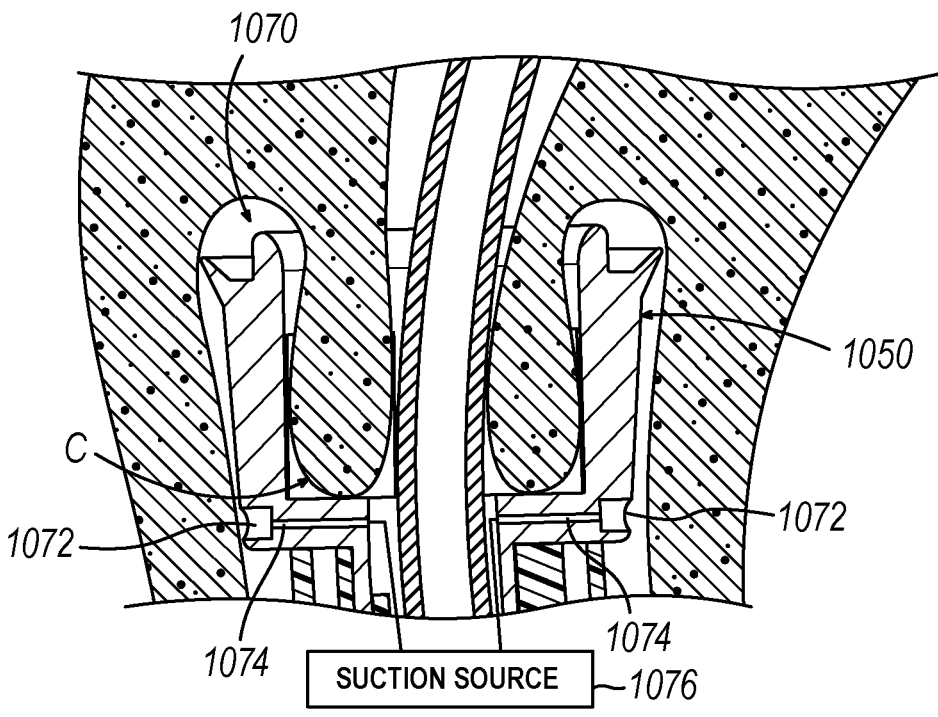
FIG. 39A depicts a mid-sagittal cross-sectional view of a cervix, with another colpotomy cup in a distal position, with a suction assembly of the colpotomy cup deactivated.
Figure 39B:
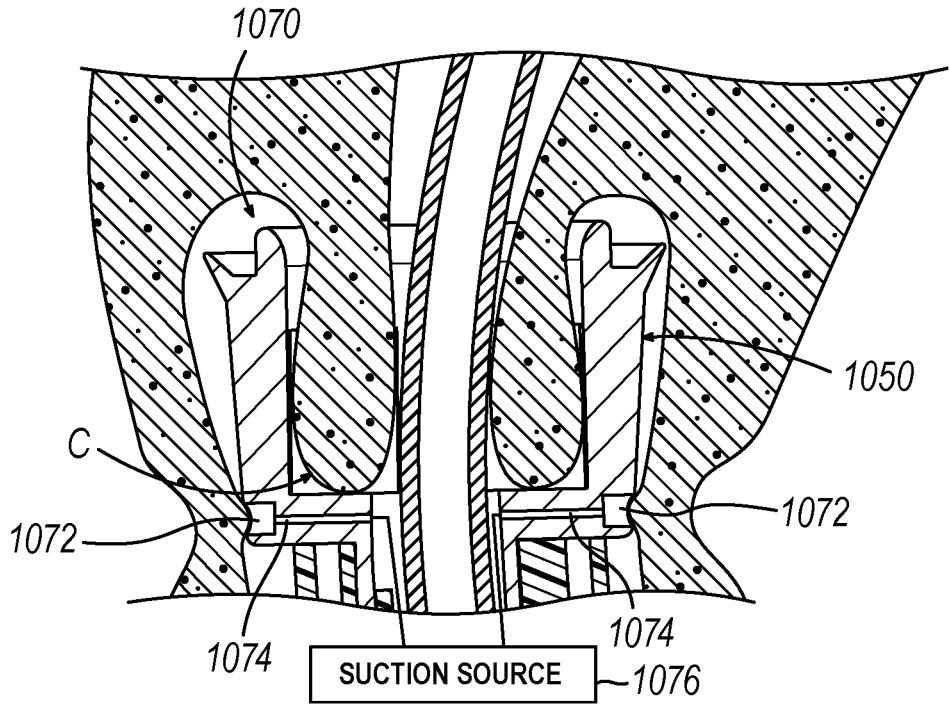
FIG. 39B depicts a mid-sagittal cross-sectional view of the cervix of FIG. 39A, with the colpotomy cup of FIG. 39A in a distal position, with the suction assembly of FIG. 39A activated.
Figure 40:
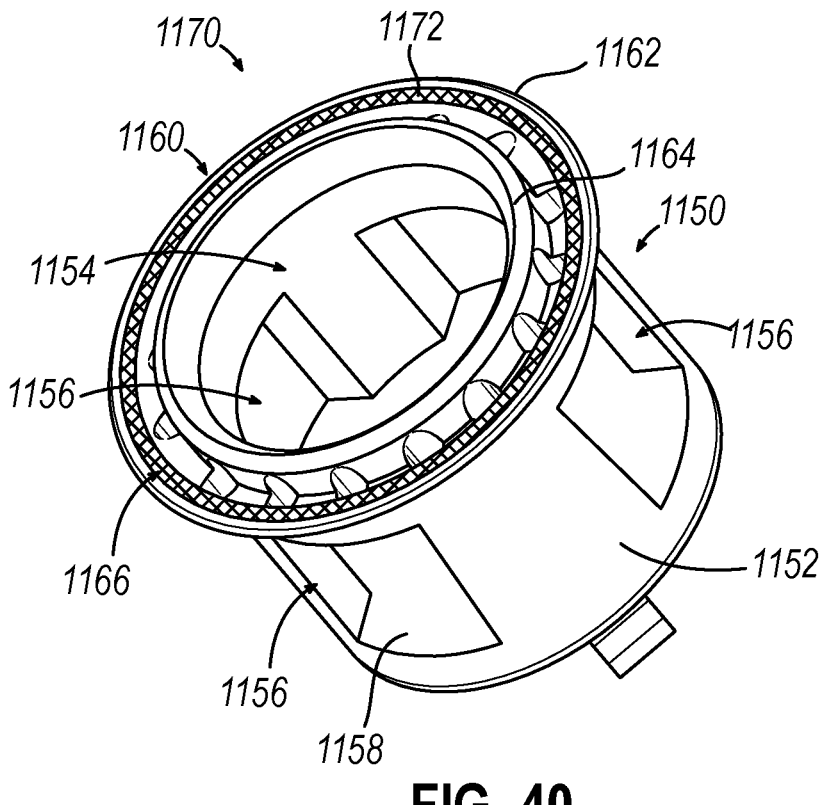
FIG. 40 depicts a perspective view of another exemplary colpotomy cup.

FIGS. 39A-39B show another colpotomy cup (1050) that is substantially similar to colpotomy cup (950) mentioned above, except the current colpotomy cup (1050) has a suction assembly (1070) with suction ports (1072) associated on an exterior surface of body located in a more proximal position. Therefore, suction assembly (1070) includes fluid lines (1074) and suction source (1076) which are substantially similar to fluid lines (974) and suction source (976) described above. As shown in FIG. 39B, when suction source (1076) is activated, the tissue gripped is located proximal to a distal end of colpotomy cup (1050).

Some versions may include a colpotomy cup that is substantially similar to both colpotomy cups (950, 1050) described above, but having both proximal suction ports (1072) and distal suction ports (972).

IX. Exemplary Colpotomy Cup with Suction Features and RF Energy Tissue Cutting Features As mentioned above, in a hysterectomy, one or more cutting instruments are introduced laparoscopically via the patient's abdomen to approach the cervicovaginal junction from outside the uterus (U) and vagina (V) in order to cut the uterus (U) away at the cervicovaginal junction, generally tracing around the circular perimeter defined by distal end (360) of colpotomy cup (350). In some instances, it may be desirable to provide features for promoting the creation of a precise colpotomy cut. For example, in an exemplary hysterectomy, one or more cutting instruments may accidently contact portions of the uterus (U) not within the circular perimeter defined by distal end (360), thereby accidently making incisions at unintended locations. Therefore, it may be desirable to provide a feature configured to inhibit tissue cutting at locations other than the intended colpotomy location.

FIGS. 37-38A shows an exemplary colpotomy cup (1150) that may be readily incorporated into uterine manipulator (300, 400, 500) in replacement of colpotomy cup (350, 450, 550). Colpotomy cup (1150) is substantially similar to colpotomy cup (350, 450, 550, 650) described above, with differences elaborated below. Colpotomy cup (1150) includes a suction assembly (1180) which is substantially similar to suction assembly (970) described above. Additionally, colpotomy cup (1150) includes an energy activated tissue cutting assembly (1070) configured to selectively cut tissue located within a space (1160) of colpotomy cup (1150).

Colpotomy cup (1150) includes a body (1152) having a floor (1158), an obliquely presented annular edge (1162), and an annular edge (1164); which may be substantially similar to body (352), floor (358), obliquely presented annular edge (362), and annular edge (364) described above, respectively, with differences elaborated below. Body (1152) defines an interior space (1154), lateral openings (1156), and open distal end (1160); which may be substantially similar to interior space (354), lateral openings (356), and open distal end (360) described above, respectively, with differences elaborated below. Annular edges (1162, 1164) define a space (1166) which may be substantially similar to space (366) described above, with differences elaborated below.

Figure 41A:
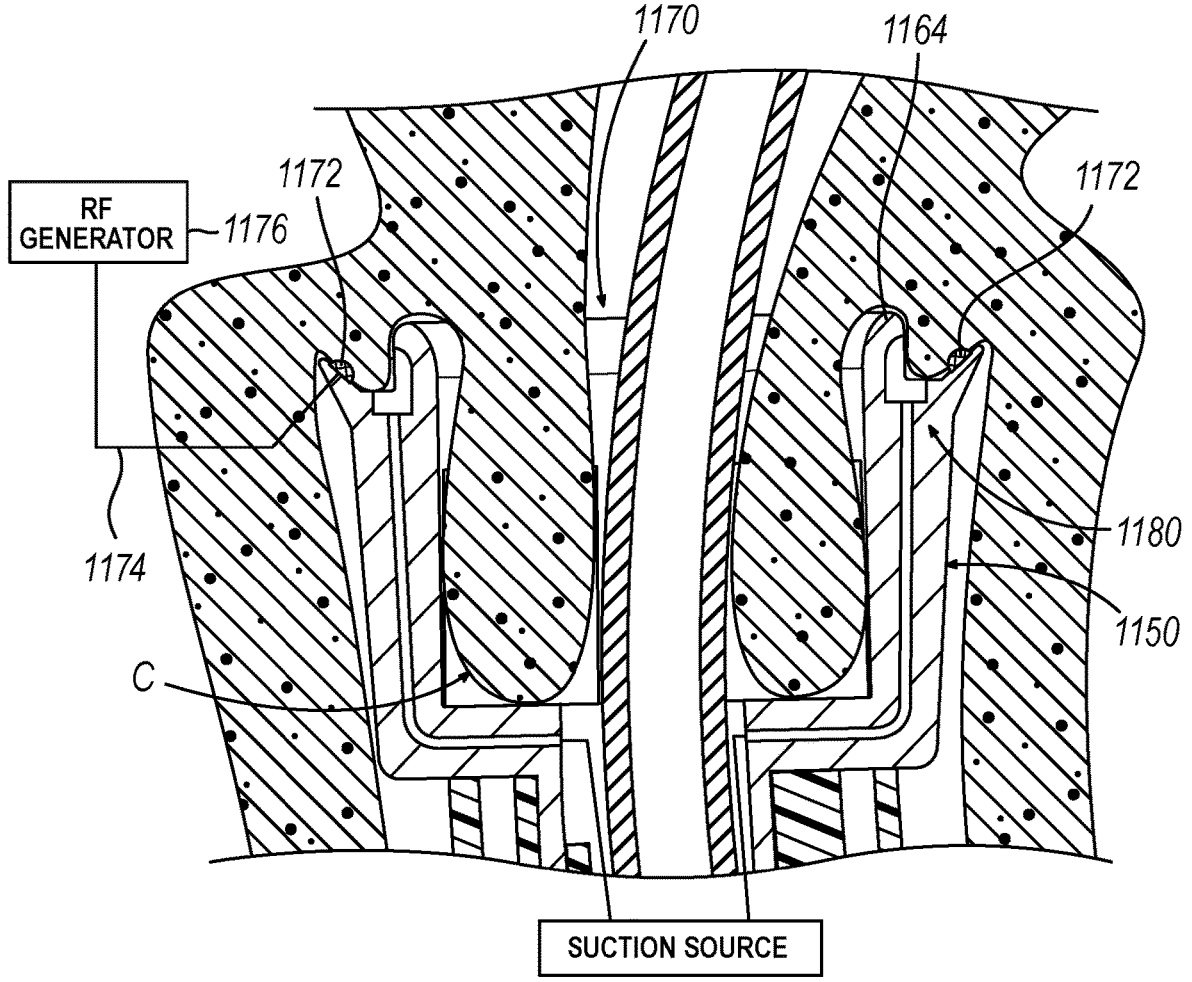
FIG. 41A depicts a mid-sagittal cross-sectional view of a cervix, with the colpotomy cup of FIG. 40 in a distal position, with a suction assembly of the colpotomy cup activated.
Figure 41B:
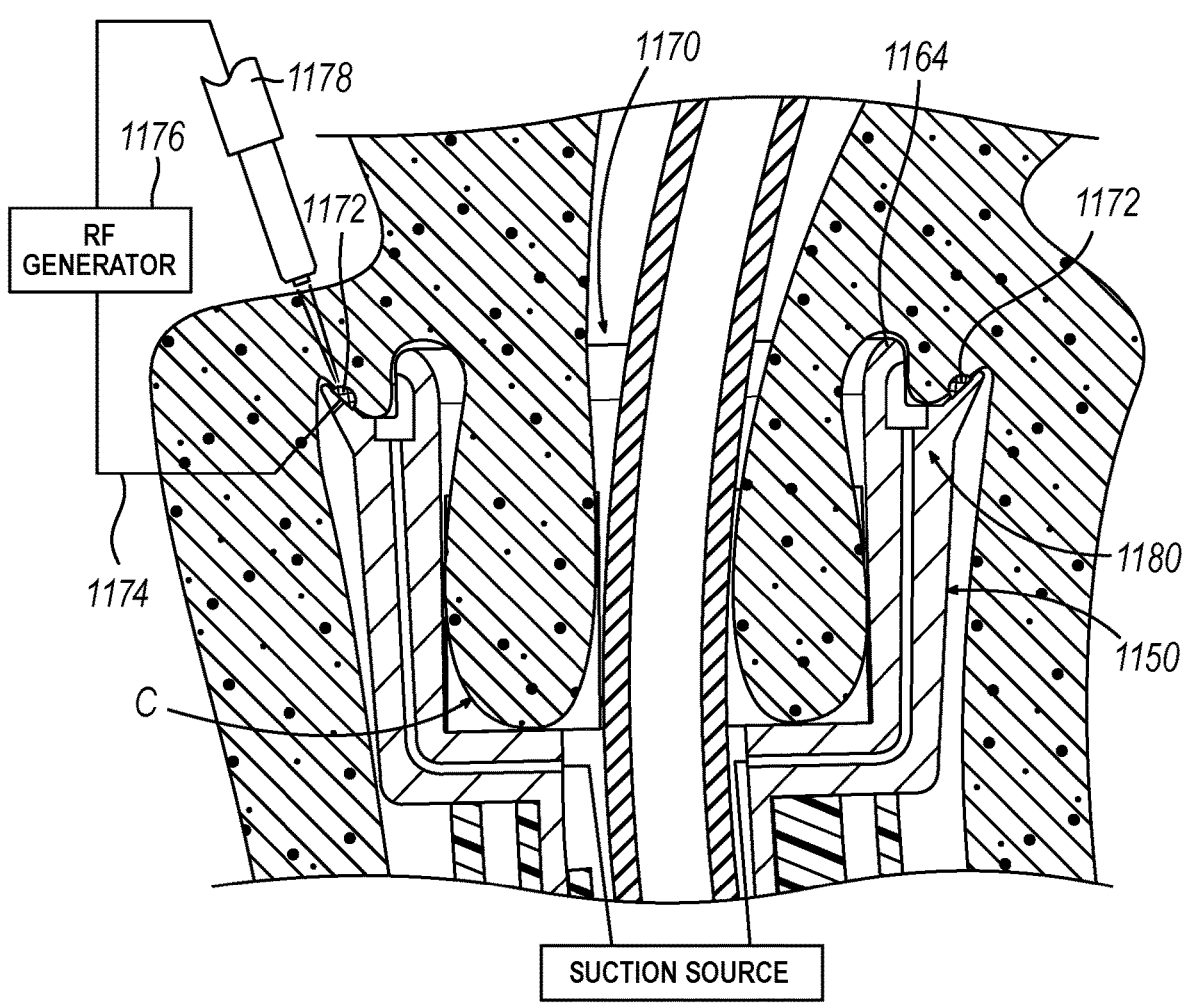
FIG. 41B depicts a mid-sagittal cross-sectional view of the cervix of FIG. 41A, with the colpotomy cup of FIG. 40 in the distal position, with the suction assembly of FIG. 41A activated, with an electrode cutting instrument cutting tissue.

Energy activated tissue cutting assembly (1170) includes an electrode ring (1172) located within space (1166). Electrode ring (1172) is sufficiently located within space (116) such that annular edges (1162, 1164) shield ring (1172) from contact with certain anatomy, such ureters, bladder, and/or colon, etc. As best shown in FIGS. 41A-41B, electrode ring (1172) is coupled to an RF generator (1176) via electrical wiring (1174). RF generator (1176) is also configured to couple to an RF activated separation tool (1178) on the laparoscopic side (i.e., external to the uterus (U), but within the patient's abdomen). Separation tool (1178) of this example includes an active electrode, such that separation tool (1178) may be used as an electrosurgical scalpel. Electrode ring (1172) is configured to act as a return path for the active electrode of separation tool (1178), such that when separation tool (1178) comes into sufficient contact with tissue near ring (1172), the RF energy may pass through the tissue that is between the electrode of separation tool (1178) and ring (1172) and thereby transect the tissue. Utilizing electrode ring (1172) to act as a return path for separation tool (1178) may inhibit separation tool from applying RF energy to unintentional anatomy. This may allow energy activated tissue cutting assembly (1170) act as a guide for separation tool (1178) when performing a colpotomy, which may in turn provide a more precise colpotomy cut. Moreover, the bipolar RF energy applied by the combination of the electrode of separation tool (1178) and ring (1172) may substantially seal the tissue as the tissue is transected, thereby minimizing bleeding. In some instances, separation tool (1178) may also contain a blade or other complementary cutting features that are designed to cooperate with the RF energy provided by generator (1176) to cut tissue.

Figure 41C:
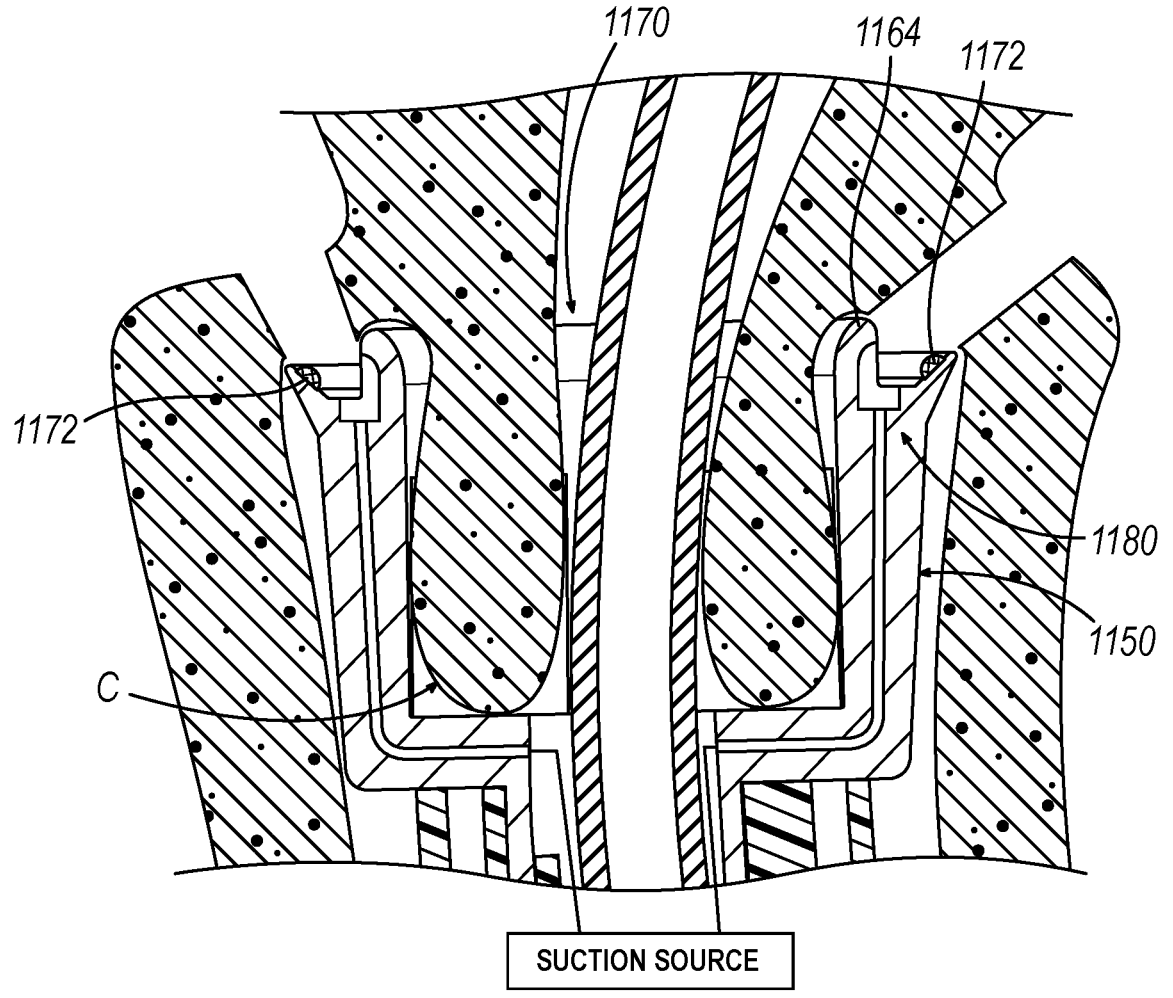
FIG. 41C depicts a mid-sagittal cross-sectional view of the cervix of FIG. 41A after the electrode cutting instrument of FIG. 41B has fully cut the tissue as shown in FIG. 41B.

FIGS. 41A-41C show an exemplary use of colpotomy cup (1150) to perform an exemplary colpotomy in accordance with the description herein. First, as shown in FIG. 41A, colpotomy cup (1150) may be suitably placed to house cervix (C). Next, as also shown in FIG. 41A, suction assembly (1180) may be unitized in accordance with the description herein to suitably grasp tissue within space (1166). Next, as shown in FIG. 41B, separation tool (1178) may be introduced laparoscopically and dragged along the tissue over electrode ring (1172) in order to cut the tissue along the annular path provided by electrode ring (1172) via RF energy until the cutting is completed as indicated in FIG. 41C.

X. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a base portion configured to selectively couple with a robotic arm; (b) a shaft assembly extending distally from the base porting, wherein the shaft assembly comprises: (i) an elongated shaft terminating into a distal end, and (ii) a distal anchoring member coupled to a portion of the elongated shaft; (c) a colpotomy cup slidably attached along a length of the elongated shaft, wherein the colpotomy cup is configured to acuate along the elongated shaft between a proximal position and a distal position; and (d) a colpotomy cup actuation assembly configured to drive the colpotomy cup between the proximal position and the distal position, wherein the colpotomy cup actuation assembly comprises: (i) an actuating assembly configured to operatively couple with a drive output of the robotic arm, and (ii) an elongated member extending distally from the actuating assembly and terminating into a distal end fixed relative to the colpotomy cup, wherein the actuating assembly is configured to drive movement of the elongated member relative to the elongated shaft to thereby drive movement of the colpotomy cup between the proximal position and the distal position.

Example 2

The apparatus of Example 1, further comprising a sleeve fixed to the colpotomy cup and extending proximally from the colpotomy cup.

Example 3

The apparatus of Example 2, wherein the distal end of the elongated member is attached to the sleeve.

Example 4

The apparatus of any of Examples 1 through 3, wherein the elongated member comprises a wire.

Example 5

The apparatus of Example 4, wherein the actuating assembly comprises a drive output and a wire actuating assembly interposed between the drive output and the wire.

Example 6

The apparatus of any of Examples 1 through 5, wherein the colpotomy cup further comprises an illumination assembly.

Example 7

The apparatus of Example 6, wherein the illumination assembly comprises an annular illuminating feature extending along an annular distal end of the colpotomy cup.

Example 8

The apparatus of any of Examples 6 through 7, wherein the illumination assembly comprises an LED fixed to a floor of the colpotomy cup.

Example 9

The apparatus of any of Examples 1 through 8, wherein the colpotomy cup comprises a suction assembly configured to apply suction to tissue.

Example 10

The apparatus of Example 9, wherein the suction assembly comprises an annular array of suction ports defined by the colpotomy cup.

Example 11

The apparatus of Example 10, wherein the annular array of suction ports is located at a proximal portion of the colpotomy cup.

Example 12

The apparatus of any of Examples 1 through 11, wherein the colpotomy cup comprises a lasso wire configured to transition between an expanded configuration and a contracted configuration.

Example 13

The apparatus of Example 12, wherein the base comprise a lasso wire drive assembly configured to mate with the robotic arm in order to drive the lasso wire between the expanded configuration and the contracted configuration.

Example 14

The apparatus of any of Examples 1 through 13, wherein the colpotomy cup comprises a locking ring configured to selectively inhibit movement of the colpotomy up relative to the elongated shaft.

Example 15

The apparatus of any of Examples 1 through 14, wherein the colpotomy cup further comprises a tissue sensor assembly configured to determine if tissue moves within an interior space defined by the colpotomy cup.

Example 16

An apparatus, comprising: (a) a base portion configured to selectively couple with a robotic arm; (b) a shaft assembly extending distally from the base porting, wherein the shaft assembly comprises: (i) an elongated shaft terminating into a distal end, and (ii) a distal anchoring member coupled to a portion of the elongated shaft; (c) a colpotomy cup slidably attached along a length of the elongated shaft, wherein the colpotomy cup is configured to acuate along the elongated shaft between a proximal position and a distal position; and (d) an energy activated assembly configured to apply RF energy to tissue received within the annular space, wherein the energy activated assembly comprises: (i) an electrode associated with the colpotomy cup, (ii) an RF generator in communication with the electrode, and (iii) an energy activated tool in communication with the RF generator such that the electrode associated with the colpotomy cup is configured to cooperate with a corresponding electrode of the energy activate tool to apply RF energy to tissue positioned between the electrodes.

Example 17

The apparatus of Example 16, wherein the electrode comprises a ring shape.

Example 18

The apparatus of any of Examples 16 through 17, wherein the annular space is defined by a distally extending annular edge and an obliquely extending annular edge of the colpotomy cup.

Example 19

The apparatus of any of Examples 16 through 8, wherein the energy activated tool comprises a laparoscopic tool.

Example 20

An apparatus, comprising: (a) a base portion configured to selectively couple with a robotic arm; (b) a shaft assembly extending distally from the base porting, wherein the shaft assembly comprises: (i) an elongated shaft terminating into a distal end, and (ii) a distal anchoring member coupled to a portion of the elongated shaft; (c) a colpotomy cup slidably attached along a length of the elongated shaft, wherein the colpotomy cup is configured to acuate along the elongated shaft between a proximal position and a distal position, wherein the colpotomy cup defines an interior region dimensioned to house a cervix of a patient receive tissue; and (d) a tissue sensing assembly associated with the interior region of the colpotomy cup, wherein the tissue sensing assembly is configured to sense movement of the cervix within the interior region of the colpotomy cup.

Example 21

An apparatus, comprising: (a) a modular colpotomy cup component, comprising: (i) a proximal base configured to couple to a distal end of a head of a robotic arm, wherein the proximal base defines an opening, (ii) an elongated sleeve extending distally from the proximal base, (iii) an expanding member attached to an outer surface of the elongated sleeve, and (iv) a colpotomy cup attached to a distal end of the elongated sleeve; and (b) a modular shaft component, comprising: (i) a coupling body configured to couple to the head of the robotic arm such that the modular shaft component and the modular colpotomy cup component are attached to each other via the head of the robotic arm, and (ii) an elongated shaft extending distally from the coupling body, wherein the elongated shaft is configured to be inserted through the opening of the proximal base such that the coupling body is configured to couple to the head of the robotic arm.

Example 22

The apparatus of Example 21, wherein the elongated sleeve extends along a curved axis.

Example 23

The apparatus of Example 22, wherein the elongated shaft is configured to extend within the elongated sleeve and distally past the colpotomy cup while the modular shaft component and the modular colpotomy cup component are attached to each other via the head of the robotic arm.

Example 24

The apparatus of Example 23, wherein the elongated shaft is configured to conform to the curved profile of the elongated sleeve.

Example 25

The apparatus of any of Examples 21 through 24, wherein the elongated shaft comprises an anchoring member.

Example 26

The apparatus of Example 25, wherein the anchoring member comprises a balloon.

Example 27

The apparatus of Example 26, wherein the balloon is configured to extend distally past the colpotomy cup while the modular shaft component is coupled to the head of the robotic arm.

Example 28

The apparatus of any of Examples 21 through 27, wherein the elongated shaft is configured to actuate distally and proximally relative to the coupling body.

Example 29

The apparatus of Example 28, wherein the coupling body is configured to operatively couple with the head of the robotic arm such that the robotic arm is configured to drive auction of the elongated shaft relative to the coupling body.

Example 30

The apparatus of Example 31, wherein the elongated sleeve is fixed to the proximal base.

Example 31

The apparatus of any of Examples 21 through 30, wherein the colpotomy cup comprises a suction assembly configured to selectively grasp tissue.

Example 32

The apparatus of any of Examples 21 through 31, wherein the colpotomy cup comprises a tissue sensing assembly configured to detect movement of tissue relative to the colpotomy cup.

Example 33

The apparatus of Example 32, wherein the tissue sensing assembly comprises a linear array of tissue sensing elements.

Example 34

The apparatus of Example 33, wherein the linear array of tissue sensing elements comprise impedance sensors.

Example 35

The apparatus of any of Examples 21 through 34, wherein the expandable member comprises a balloon.

Example 36

An apparatus, comprising: (a) a modular colpotomy cup component extending between a proximal end and a distal end, wherein the modular colpotomy cup component comprises: (i) an elongated sleeve configured to attach to a first face of a robotic head, wherein the elongated sleeve comprises a first expandable member, and (ii) a colpotomy cup located at the distal end and attached to the elongated sleeve, wherein the colpotomy cup and the elongated sleeve define a pathway extending between the proximal end and the distal end; and (b) a modular shaft component configured to selectively couple with the modular colpotomy cup component, wherein the modular shaft component comprises: (i) an elongated shaft configured to be inserted through pathway of the modular colpotomy cup component, (ii) a second expandable member attached to the elongated shaft such that the second expandable member extends distally past the colpotomy cup when the modular shaft component is coupled to the modular colpotomy cup component, and (iii)

a coupling body configured to attach to a second face of the robotic head, wherein the coupling body is proximal relative to the modular colpotomy cup component while attached to the second face of the robotic head.

Example 37

The apparatus of Example 36, wherein the elongated shaft is configured to acuate relative to the coupling body while attached to the robotic head.

Example 38

The apparatus of Example 37, wherein the robotic head is configured to drive actuation of the elongated shaft relative to the coupling body.

Example 39

The apparatus of any of Examples 36 through 38, wherein the second expandable member comprises a balloon.

Example 40

An apparatus, comprising: (a) a robotic drive arm comprising a proximally presented face and a distally presented face; (b) a modular colpotomy cup component configured to selectively attach to the distally presented face of the robotic drive arm, the modular colpotomy cup component comprising: (i) a proximal base configured to couple to the distally presented face of the robotic drive arm, wherein the proximal base defines an opening, (ii) an elongated sleeve extending distally from the proximal base, and (iii) a colpotomy cup attached to a distal end of the elongated sleeve; and (c) a modular shaft component, comprising: (i) a coupling body configured to couple to the proximally presented face of the robotic drive arm such that the modular shaft component and the modular colpotomy cup component are attached to each other via the robotic drive arm, and (ii) an elongated shaft extending distally from the coupling body.

XI. Miscellaneous

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those of ordinary skill in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a robotic drive arm comprising a proximally presented face and a distally presented face, wherein the space between the distally presented face and proximally presented face of the robotic drive arm defines a housing;
   (b) a modular colpotomy cup component configured to selectively attach to the distally presented face of the robotic drive arm, the modular colpotomy cup component comprising:
      (i) a proximal base configured to couple to the distally presented face of the robotic drive arm, wherein the proximal base defines an opening,
      (ii) an elongated sleeve extending distally from the proximal base, and
      (iii) a colpotomy cup attached to a distal end of the elongated sleeve; and (iv) a distal end of the colpotomy cup having a first annular edge and a second annular edge; and
      (v) an annular array of suction ports between the first annular edge and second annular edge; and
      (vi) a suction source in fluid communication with the annular array of suction ports by one or more fluid lines; and
   (c) a modular shaft component, comprising:
      (i) a coupling body configured to couple to the proximally presented face of the robotic drive arm such that the modular shaft component and the modular colpotomy cup component are attached to each other via the robotic drive arm, and
      (ii) an elongated shaft extending distally from the coupling body;
   (d) an actuation assembly in the housing, comprising:
      (i) a drive input operatively coupled with a drive output in the proximal base of the modular colpotomy cup.

2. The apparatus of claim 1, wherein the elongated sleeve extends along a curved axis.

3. The apparatus of claim 2, wherein the elongated shaft is configured to extend within the elongated sleeve and distally past the colpotomy cup while the modular shaft component and the modular colpotomy cup component are attached to each other via the robotic drive arm.

4. The apparatus of claim 3, wherein the elongated shaft is configured to conform to the curved axis of the elongated sleeve.

5. The apparatus of claim 1, wherein the elongated shaft comprises an anchoring member.

6. The apparatus of claim 5, wherein the anchoring member comprises a balloon.

7. The apparatus of claim 6, wherein the balloon is configured to extend distally past the colpotomy cup while the modular shaft component is coupled to the robotic drive arm.

8. The apparatus of claim 1, wherein the elongated shaft is configured to actuate distally and proximally relative to the coupling body.

9. The apparatus of claim 8, wherein the coupling body is configured to operatively couple with robotic drive arm such that the robotic drive arm is configured to drive actuation of the elongated shaft relative to the coupling body.

10. The apparatus of claim 1, wherein the elongated sleeve is fixed to the proximal base.

11. The apparatus of claim 1, wherein the colpotomy cup selectively grasps tissue by activation of the suction source.

12. The apparatus of claim 1, wherein the colpotomy cup comprises a tissue sensing assembly configured to detect movement of tissue relative to the colpotomy cup.

13. The apparatus of claim 12, wherein the tissue sensing assembly comprises a linear array of tissue sensing elements.

14. The apparatus of claim 13, wherein the linear array of tissue sensing elements comprise impedance sensors.

15. The apparatus of claim 1, wherein the outer surface of the elongated sleeve comprises an expandable member.

16. The apparatus of claim 15, wherein the expandable member comprises a balloon.

* * * * *